US008273794B2

(12) United States Patent
Gomez-Orellana et al.

(10) Patent No.: US 8,273,794 B2
(45) Date of Patent: Sep. 25, 2012

(54) COMPOUNDS AND COMPOSITIONS FOR DELIVERING ACTIVE AGENTS

(75) Inventors: Maria Isabel Gomez-Orellana, New Rochelle, NY (US); David Gschneidner, Thornwood, NY (US); Andrea Leone-Bay, Ridgefield, CT (US); Destardi Moye-Sherman, Newburgh, NY (US); Stephen V. Pusztay, Sleepy Hollow, NY (US); Parshuram Rath, Yorktown Heights, NY (US); Pingwah Tang, Elmsford, NY (US); John J. Weidner, Wappingers Falls, NY (US); Jianfeng Song, West Windsor, NJ (US)

(73) Assignee: Emisphere Technologies, Inc., Cedar Knolls, NJ (US)

( * ) Notice: Subject to any disclaimer, the term of this patent is extended or adjusted under 35 U.S.C. 154(b) by 1284 days.

(21) Appl. No.: 11/569,004

(22) PCT Filed: May 16, 2005

(86) PCT No.: PCT/US2005/017309
§ 371 (c)(1),
(2), (4) Date: Jun. 18, 2007

(87) PCT Pub. No.: WO2005/112633
PCT Pub. Date: Dec. 1, 2005

(65) Prior Publication Data
US 2008/0255250 A1 Oct. 16, 2008

Related U.S. Application Data

(60) Provisional application No. 60/571,195, filed on May 14, 2004, provisional application No. 60/571,194, filed on May 14, 2004, provisional application No. 60/571,090, filed on May 14, 2004, provisional application No. 60/571,093, filed on May 14, 2004, provisional application No. 60/571,151, filed on May 14, 2004, provisional application No. 60/571,144, filed on May 14, 2004, provisional application No. 60/571,089, filed on May 14, 2004, provisional application No. 60/571,092, filed on May 14, 2004, provisional application No. 60/571,055, filed on May 14, 2004, provisional application No. 60/571,315, filed on May 14, 2004, provisional application No. 60/576,397, filed on Jun. 1, 2004, provisional application No. 60/576,105, filed on Jun. 1, 2004, provisional application No. 60/576,088, filed on Jun. 1, 2004.

(51) Int. Cl.
*A61K 31/19* (2006.01)
*A61K 31/195* (2006.01)
*C07C 229/00* (2006.01)

(52) U.S. Cl. ........ 514/570; 514/557; 514/563; 562/433; 562/442; 562/449; 562/454; 562/455; 562/457

(58) Field of Classification Search .................. 562/449, 562/433, 442, 454, 455, 457; 514/557, 563, 514/570
See application file for complete search history.

(56) References Cited

U.S. PATENT DOCUMENTS

| 3,072,473 | A | 1/1963 | Harris |
| 5,366,519 | A | 11/1994 | Cherpeck |
| 5,773,647 | A | 6/1998 | Leone-Bay et al. |
| 6,166,015 | A | 12/2000 | Rogers et al. |
| 6,348,474 | B1 * | 2/2002 | Kayakiri et al. ............... 514/303 |
| 6,531,474 | B1 * | 3/2003 | Wannamaker et al. ........ 514/248 |
| 2003/0096019 | A1 | 5/2003 | Currie et al. |
| 2004/0014993 | A1 | 1/2004 | Taneja et al. |
| 2004/0048777 | A1 * | 3/2004 | Weidner et al. .................... 514/2 |

FOREIGN PATENT DOCUMENTS

| EP | 0129791 A2 | 1/1985 |
| EP | 0270093 A2 | 6/1988 |
| GB | 842998 * | 8/1960 |
| WO | 96/30036 | 10/1996 |
| WO | 00/22909 | 4/2000 |
| WO | WO-00/59863 | 10/2000 |
| WO | WO-01/32130 | 5/2001 |
| WO | WO-01/44199 | 6/2001 |
| WO | WO-02/02509 | 1/2002 |
| WO | WO-02/06229 | 1/2002 |
| WO | 02/15959 | 2/2002 |
| WO | 02/20466 | 3/2002 |
| WO | WO-02/19969 | 3/2002 |

OTHER PUBLICATIONS

Leon-Bay et al , Synthesis and Evaualtion of compounds taht facilitate the gastrointestinal absorption of Heparin, 1998, J. Med. Chem., 41, p. 1163-1171.*
D. Evans et al , Some Substituted Phneylalkanoic Acids and N-substituted Malonanilic Succinanilic and Anilionalkanoic acids as Potential Antiinflammatory Agents, 1969,J. of Medicinal Chemistry, 12(5), p. 1006-1010.*
Siegel et al , The Reactions of Antiserum Homologous to the p-Azomaleanilate and p-Azofumaranilate Ion Groups,1954, J. of the American Chemical Society, vol. 76, p. 2464-2866.*
Sobotka et al , P-Hydroxyphenoxy Aliphatic Acids,1952, J. of the American Chemical Society,74, p. 3813-3815.*
Evans, D., et al: "Substituted phenylalkanoic acids and N-substituted malonanilic, succinanilic, and anilinoalkanoic acids as potential antiinflammatory agents" Journal of Medicinal Chemistry, 12(5), 1006-10 CODEN: JMCMAR; ISSN: 0022-2623, 1969, XP002426297.
Database CA [Online] Chemical Abstracts Service, Columbus, Ohio, US; Ashwell, Mark Anthony et al: "Preparation of heterocyclic amino alcohol beta-3 adrenergic receptor agonists" XP002426300 retrieved from STN Database accession No. 136:134675.
Gregory, M. J., : "Succinamic acids. II. Anhydrides as intermediates in the aminolysis of N-alkylanilic acids in toluene" Journal of the Chemical Society, Perkin Transactions 2: Physical Organic Chemistry (1972-1999), (10), 1389-93 CODEN: JCPKBH; ISSN: 0300-9580, 1972, XP002426298.

(Continued)

*Primary Examiner* — Taylor Victor Oh
(74) *Attorney, Agent, or Firm* — Blank Rome LLP

(57) ABSTRACT

Compounds and compositions for the delivery of active agents are provided. Methods of administration and preparation are provided as well.

25 Claims, No Drawings

OTHER PUBLICATIONS

Astles, P. C. et al: "Selective endothelin A receptor ligands. 1. Discovery and structure-activity of 2,4-di substituted benzoic acid derivatives" European Journal of Medicinal Chemistry, 32(5), 409-423 CODEN: EJMCA4; ISSN: 0223-5234, 1997, XP004085515.

Sobotka, H. et al: "p-Hydroxyphenoxy aliphatic acids" Journal of the American Chemical Society, 74, 3813-5 CODEN; JACSAT; ISSN: 0002-7863, 1952, XP002320342.

Treibs and Falk: "Synthesen mit Dicarbonsauren VI, Mittel.: Die Fries'sche Verschiebung an Estern von Dicarbon sauren". Chemische Berichte, vol. 87, No. 3, Mar. 1, 1954, pp. 345-349.

Extended European Search Report issued in EP10012221.7-1216/2279732 on Mar. 16, 2012.

* cited by examiner

COMPOUNDS AND COMPOSITIONS FOR DELIVERING ACTIVE AGENTS

This application is a national phase of International Application No. PCT/US2005/017309, filed May 16, 2005, which was published in English and claims the benefit of U.S. Provisional Application No. 60/576,088, filed Jun. 1, 2004, U.S. Provisional Application No. 60/576,397, filed Jun. 1, 2004, U.S. Provisional Application No. 60/576,105, filed Jun. 1, 2004, U.S. Provisional Application No. 60/571,090, filed May 14, 2004, U.S. Provisional Application No. 60/571,092, filed May 14, 2004, U.S. Provisional Application No. 60/571,195, filed May 14, 2004, U.S. Provisional Application No. 60/571,194, filed May 14, 2004, U.S. Provisional Application No. 60/571,093, filed May 14, 2004, U.S. Provisional Application No. 60/571,055, filed May 14, 2004, U.S. Provisional Application No. 60/571,151, filed May 14, 2004, U.S. Provisional Application No. 60/571,315, filed May 14, 2004, U.S. Provisional Application No. 60/571,144, filed May 14, 2004, and U.S. Provisional Application 60/571,089, filed May 14, 2004, all of which are hereby incorporated by reference.

FIELD OF THE INVENTION

The present invention relates to compounds and compositions for delivering active agents, such as biologically or chemically active agents, to a target. These compounds are well suited for forming non-covalent mixtures with active agents for oral and other routes of administration to animals. Methods for the preparation and administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, epithelium, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many active agents would be the route of choice for administration to animals if not for biological, chemical, and physical barriers. Among the numerous agents which are not typically amenable to oral administration are biologically or chemically active peptides, such as calcitonin and insulin; polysaccharides, such as mucopolysaccharides including, but not limited to, heparin; heparinoids; antibiotics; and other organic substances. These agents may be rapidly rendered ineffective or destroyed in the gastro-intestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

Proteinoid microspheres have been used to deliver pharmaceuticals. See, for example, U.S. Pat. Nos. 5,401,516; 5,443,841; and Re. 35,862. In addition, certain modified amino acids have been used to deliver pharmaceuticals. See, for example, U.S. Pat. Nos. 5,629,020; 5,643,957; 5,766,633; 5,776,888; and 5,866,536, and International Patent Publication Nos., WO98/49135; WO00/06534; WO00/07979; WO00/40203; WO00/47188; WO00/50386; WO00/59863; WO01/32130, WO01/32596, WO01/44199, WO01/51454, WO02/02509, WO02/15959, WO02/16309, WO02/20466, WO02/19969, WO02/69937, WO03/45306.".

More recently, a polymer has been conjugated to a modified amino acid or a derivative thereof via a linkage group to provide for polymeric delivery agents. The modified polymer may be any polymer, but preferred polymers include, but are not limited to, polyethylene glycol (PEG), and derivatives thereof. See, for example, International Patent Publication No. WO 00/40203.

However, there is still a need for simple, inexpensive delivery systems which are easily prepared and which can deliver a broad range of active agents by various routes.

SUMMARY OF THE INVENTION

The present invention provides compounds and compositions which facilitate the delivery of active agents. Delivery agent compounds of the present invention include compounds as shown below and pharmaceutically acceptable salts thereof:

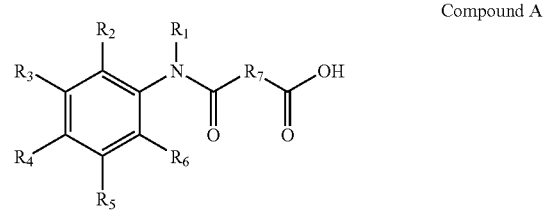

Compound A wherein:

$R_1$ is —$(CH_2)_m$—$R_8$, wherein m=0 or 1;

$R_2$-$R_6$ are independently selected from hydrogen, hydroxyl, halogen, $C_1$-$C_4$ alkyl, $C_2$-$C_4$ alkenyl, $C_2$-$C_4$ alkynyl, $C_1$-$C_4$ alkoxy, and cyano;

$R_7$ is selected from $C_1$-$C_{10}$ alkyl, $C_2$-$C_{10}$ alkenyl, and $C_2$-$C_{10}$ alkynyl;

$R_8$ is selected from cyclopentyl, cyclohexyl and phenyl, wherein when $R_8$ is a phenyl, m=1; and $R_8$ is optionally substituted with $C_1$-$C_4$ alkyl, $C_1$-$C_4$ alkoxy, halogen or hydroxyl, or a combination thereof.

In one embodiment, $R^7$ is $C_1$ alkyl.

In another embodiment, $R^7$ is $C_2$ alkyl.
In another embodiment, $R^7$ is a $C_3$ alkyl.
In another embodiment, $R^7$ is a $C_4$ alkyl.
In another embodiment, $R^7$ is a $C_5$ alkyl.
In another embodiment, $R^7$ is a $C_6$ alkyl.
In another embodiment, $R^7$ is a $C_7$ alkyl.
In another embodiment, $R^7$ is a $C_8$ alkyl.

Preferred compounds include, but are not limited to, the following compounds and pharmaceutically acceptable salts thereof:

(Compound 1)
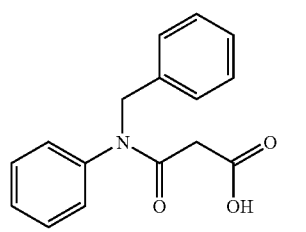

(Compound 2)
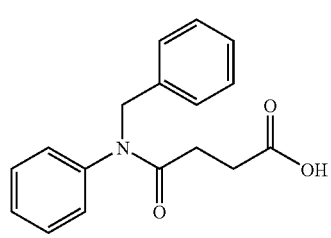

(Compound 3)
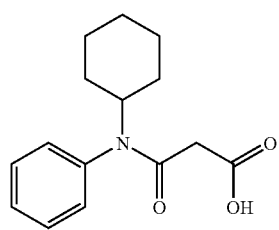

(Compound 4)
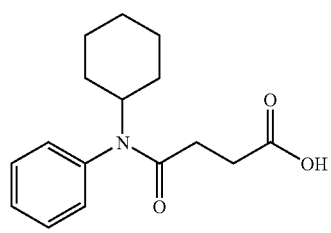

(Compound 5)
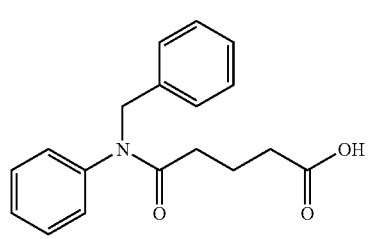

-continued (Compound 6)
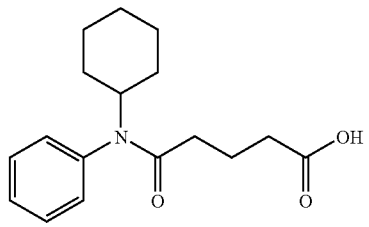

(Compound 7)
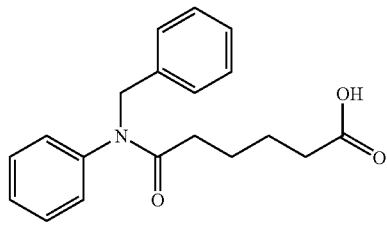

(Compound 8)
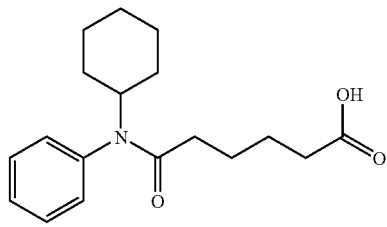

(Compound 9)
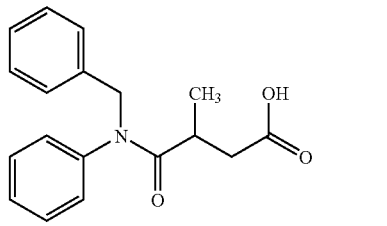

(Compound 10)
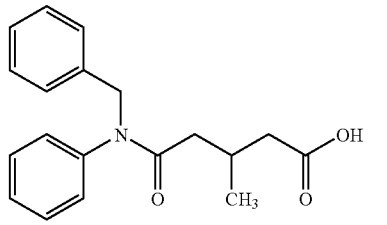

(Compound 11)
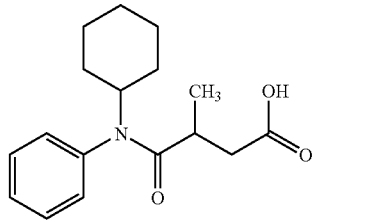

(Compound 12)
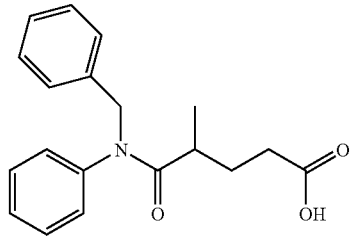

(Compound 13)
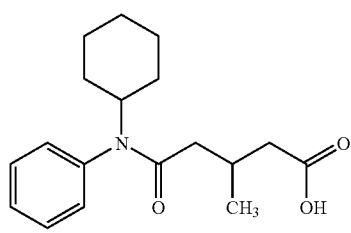

(Compound 14)
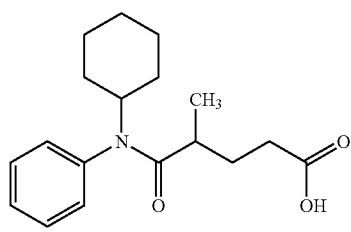

(Compound 15)
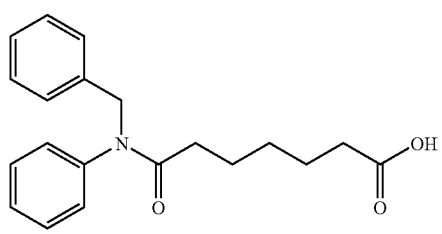

(Compound 16)
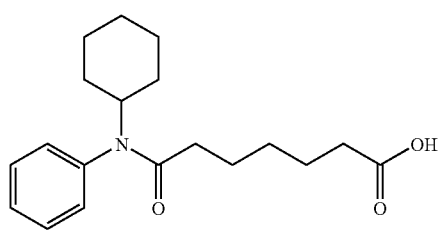

(Compound 17)
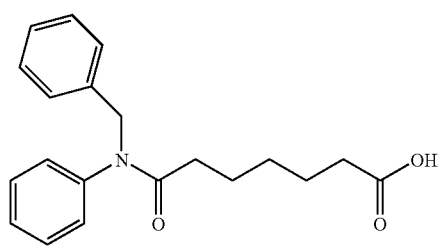

(Compound 18)
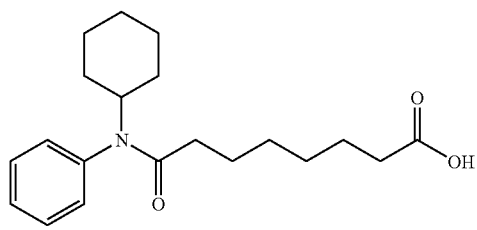

(Compound 19)
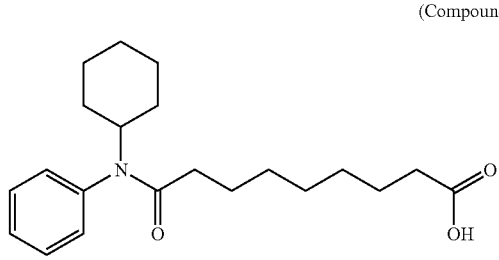

(Compound 20)
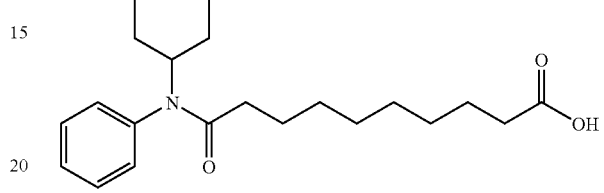

(Compound 21)
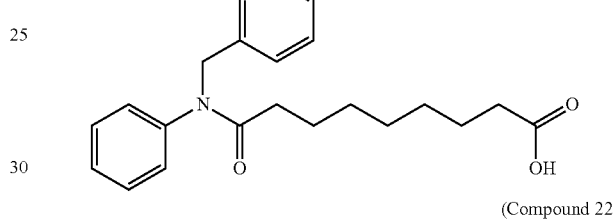

(Compound 22)
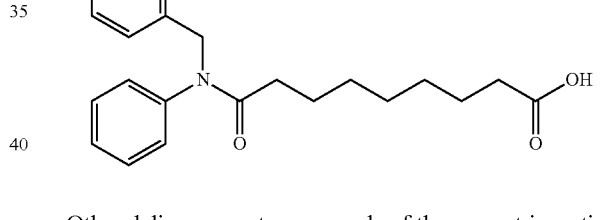

Other delivery agent compounds of the present invention include those of the formula:

(Compound B)
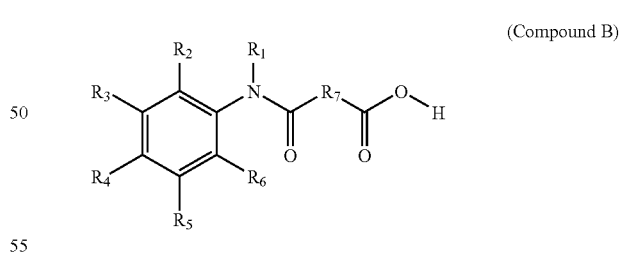

and pharmaceutically acceptable salts thereof, wherein:

$R_1$ is a $C_1$-$C_6$ alkyl, or $C_2$-$C_6$ alkenyl, $R_2$-$R_6$ are independently chosen from the group consisting of hydrogen, hydroxyl, halogen, $C_1$-$C_4$ alkyl, $C_2$-$C_4$ alkynyl, $C_2$-$C_4$ alkynyl, $C_1$-$C_4$ alkoxy, and cyano, and $R_7$ is selected from the group consisting of $C_1$-$C_{10}$ alkyl, $C_2$-$C_{10}$ alkenyl, and $C_2$-$C_{10}$ alkynyl.

In one embodiment, R2-R6 independently are hydrogen, methyl, halogen, methoxy.

In another embodiment, R2-R6 independently are hydrogen, methyl, chlorine, methoxy.

In another embodiment, R2-R6 independently are hydrogen, methyl, flourine, methoxy.

In another embodiment, R2-R6 independently are hydrogen, methyl, iodine, methoxy.

In another embodiment, R2-R6 independently are hydrogen, methyl, bromine, methoxy.

In another embodiment, R1 is $C_1$-$C_3$ alkyl.
In another embodiment, R1 is a methyl.
In another embodiment, R1 is an ethyl.
In another embodiment, R1 is an isopropyl.
In another embodiment, R2 is a methyl.
In another embodiment, R2 is a halogen.
In another embodiment, R2 is a chlorine.
In another embodiment, R2 is a flourine.
In another embodiment, R4 is a methyl.
In another embodiment, R4 is a methoxy.
In another embodiment, R4 is a halogen.
In another embodiment, R4 is a chlorine.
In another embodiment, R4 is a flourine.
In another embodiment, R4 is a cyano.
In another embodiment, R7 is a $C_1$ alkyl.
In another embodiment, R7 is a $C_2$ alkyl.
In another embodiment, R7 is a $C_2$ alkyl branched with a methyl.
In another embodiment, R7 is a $C_3$ alkyl.
In another embodiment, R7 is a $C_3$ alkyl branched with a methyl.
In another embodiment, R7 is a C4 alkyl.
In another embodiment, R7 is a $C_5$ alkyl.
In another embodiment, R7 is a $C_6$ alkyl.
In another embodiment, R7 is a $C_7$ alkyl.
In another embodiment, R7 is a $C_8$ alkyl.

Preferred compounds include, but are not limited to, the following compounds and pharmaceutically acceptable salts thereof

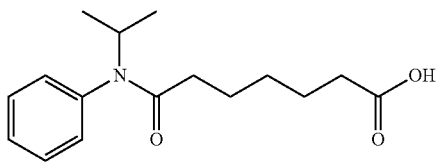

Compound 23

6-(Isopropyl-phenyl-carbamoyl)-hexanoic acid

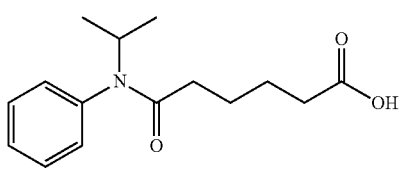

Compound 24

6-[isopropyl(phenyl)amino]-6-oxohexanoic acid

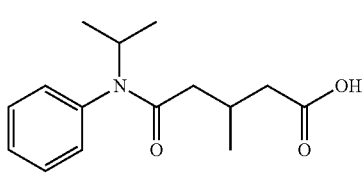

Compound 25

5-[isopropyl(phenyl)amino]-3-methyl-5-oxopentanoic acid

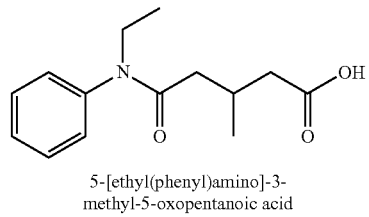

Compound 26

5-[ethyl(phenyl)amino]-3-methyl-5-oxopentanoic acid

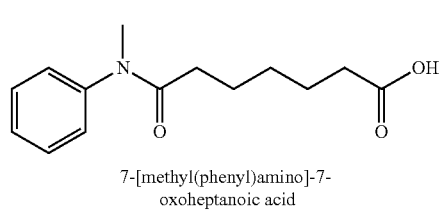

Compound 27

7-[methyl(phenyl)amino]-7-oxoheptanoic acid

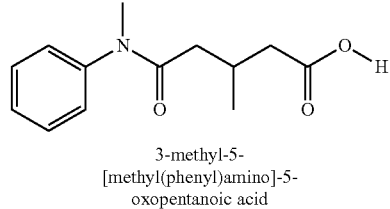

Compound 28

3-methyl-5-[methyl(phenyl)amino]-5-oxopentanoic acid

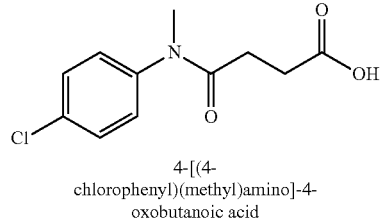

Compound 29

4-[(4-chlorophenyl)(methyl)amino]-4-oxobutanoic acid

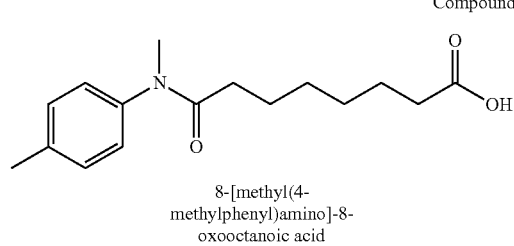

Compound 30

8-[methyl(4-methylphenyl)amino]-8-oxooctanoic acid

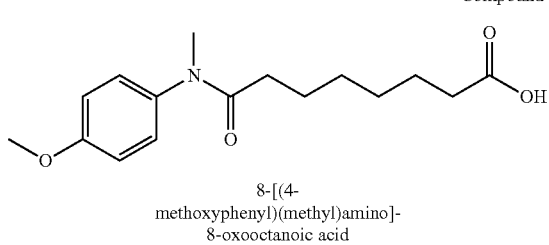

Compound 31

8-[(4-methoxyphenyl)(methyl)amino]-8-oxooctanoic acid

Compound 32

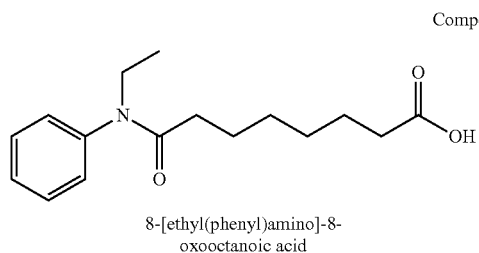

8-[ethyl(phenyl)amino]-8-oxooctanoic acid

Compound 33

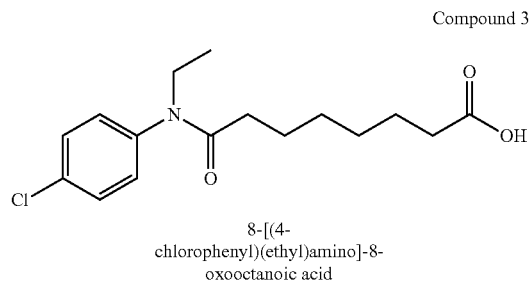

8-[(4-chlorophenyl)(ethyl)amino]-8-oxooctanoic acid

Compound 34

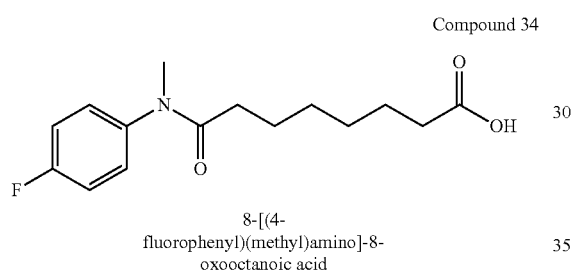

8-[(4-fluorophenyl)(methyl)amino]-8-oxooctanoic acid

Compound 35

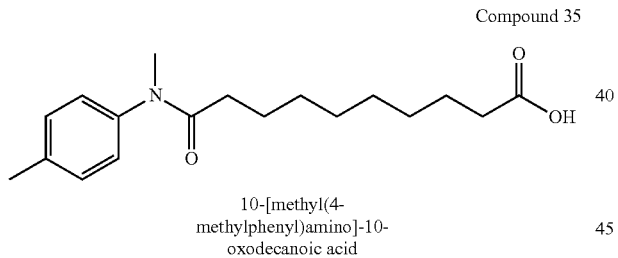

10-[methyl(4-methylphenyl)amino]-10-oxodecanoic acid

Compound 36

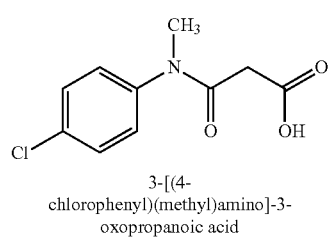

3-[(4-chlorophenyl)(methyl)amino]-3-oxopropanoic acid

Compound 37

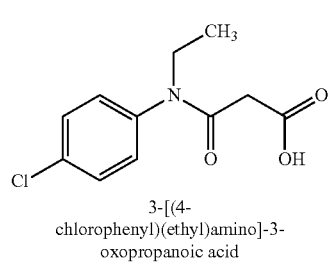

3-[(4-chlorophenyl)(ethyl)amino]-3-oxopropanoic acid

Compound 38

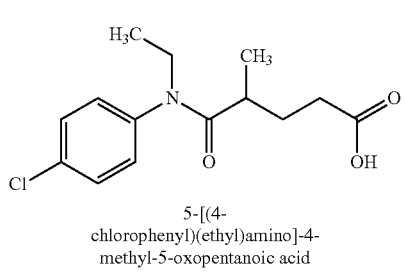

5-[(4-chlorophenyl)(ethyl)amino]-4-methyl-5-oxopentanoic acid

Compound 39

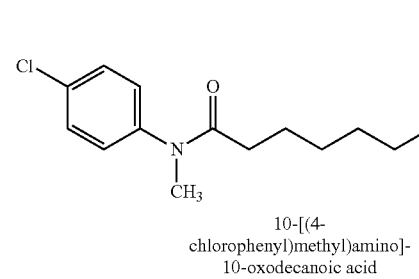

10-[(4-chlorophenyl)methyl)amino]-10-oxodecanoic acid

Compound 40

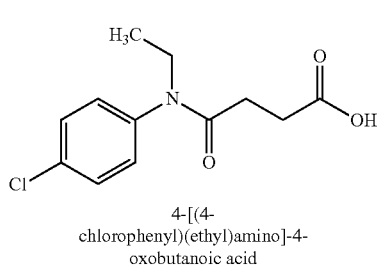

4-[(4-chlorophenyl)(ethyl)amino]-4-oxobutanoic acid

Compound 41

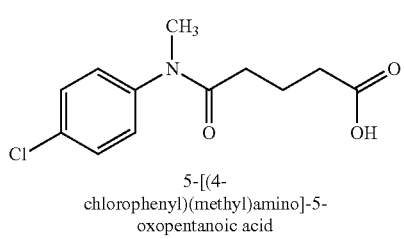

5-[(4-chlorophenyl)(methyl)amino]-5-oxopentanoic acid

Compound 42

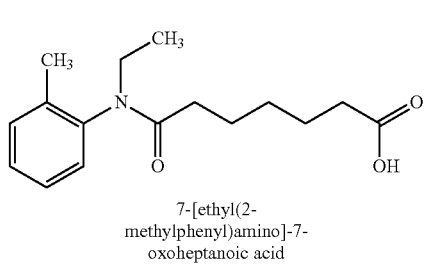

7-[ethyl(2-methylphenyl)amino]-7-oxoheptanoic acid

Compound 43

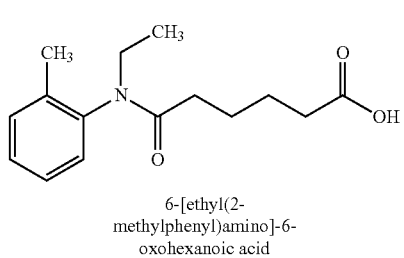

6-[ethyl(2-methylphenyl)amino]-6-oxohexanoic acid

Compound 44

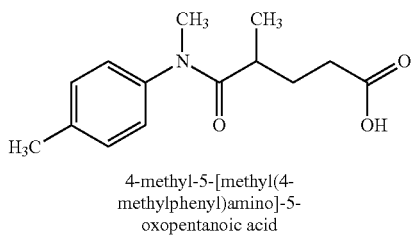

4-methyl-5-[methyl(4-methylphenyl)amino]-5-oxopentanoic acid

Compound 45

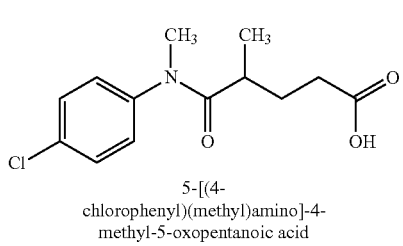

5-[(4-chlorophenyl)(methyl)amino]-4-methyl-5-oxopentanoic acid

Compound 46

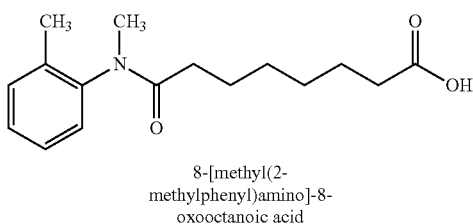

8-[methyl(2-methylphenyl)amino]-8-oxooctanoic acid

Compound 47

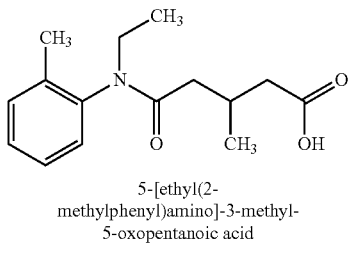

5-[ethyl(2-methylphenyl)amino]-3-methyl-5-oxopentanoic acid

Compound 48

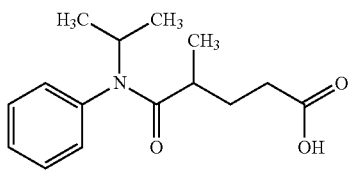

5-[isopropyl(phenyl)amino]-4-methyl-5-oxopentanoic acid

Compound 49

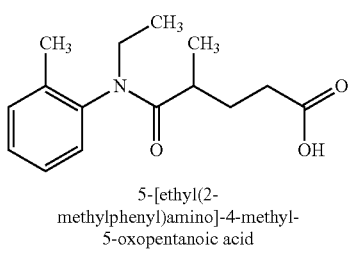

5-[ethyl(2-methylphenyl)amino]-4-methyl-5-oxopentanoic acid

Compound 50

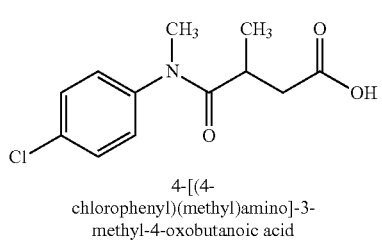

4-[(4-chlorophenyl)(methyl)amino]-3-methyl-4-oxobutanoic acid

Compound 51

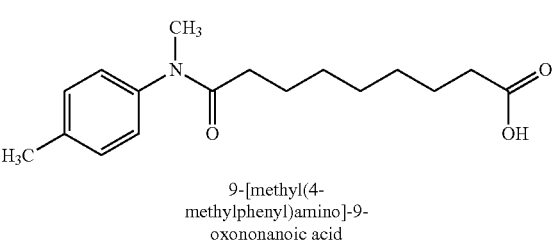

9-[methyl(4-methylphenyl)amino]-9-oxononanoic acid

Compound 52

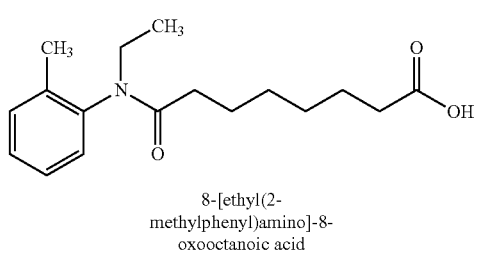

8-[ethyl(2-methylphenyl)amino]-8-oxooctanoic acid

Compound 53

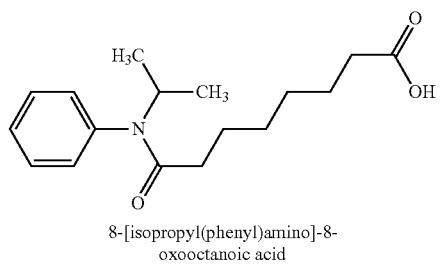

8-[isopropyl(phenyl)amino]-8-oxooctanoic acid

Compound 54

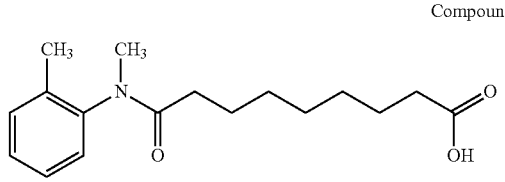

9-[methyl(2-methylphenyl)amino]-9-oxononanoic acid

Compound 55

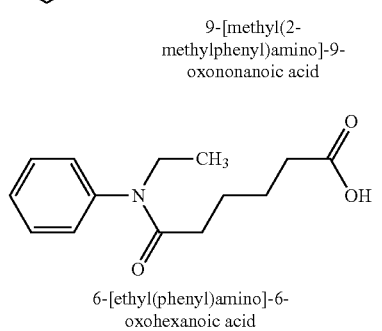

6-[ethyl(phenyl)amino]-6-oxohexanoic acid

Compound 56

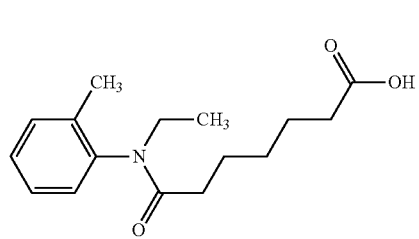

7-[ethyl(2-methylphenyl)amino]-7-oxoheptanoic acid

Compound 57

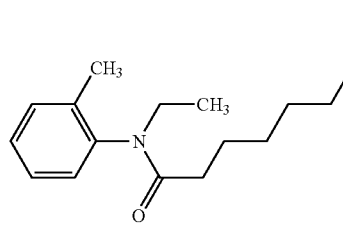

9-[ethyl(2-methylphenyl)amino]-9-oxononanoic acid

Compound 58

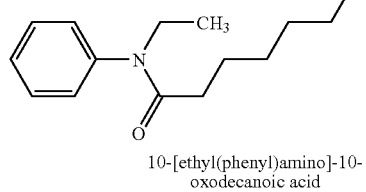

10-[ethyl(phenyl)amino]-10-oxodecanoic acid

Compound 59

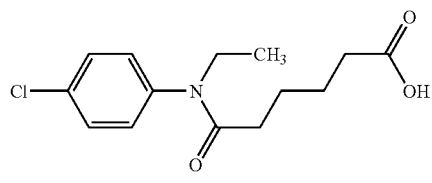

6-[(4-chlorophenyl)(ethyl)amino]-6-oxohexanoic acid

Compound 60

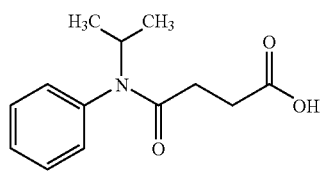

4-[isopropyl(phenyl)amino]-4-oxobutanoic acid

Compound 61

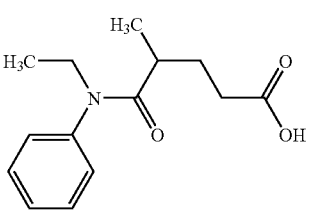

5-[ethyl(phenyl)amino]-4-methyl-5-oxopentanoic acid

Compound 62

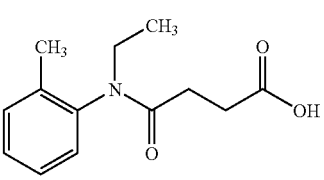

4-[ethyl(2-methylphenyl)amino]-4-oxobutanoic acid

Compound 63

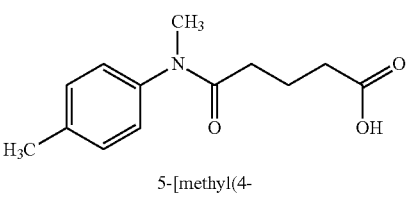

5-[methyl(4-methylphenyl)amino]-5-oxopentanoic acid

Compound 64

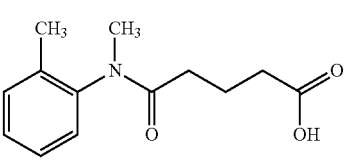

5-[methyl(2-methylphenyl)amino]-5-oxopentanoic acid

Compound 65

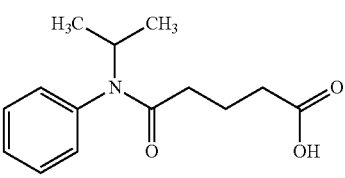

5-[isopropyl(phenyl)amino]-5-oxopentanoic acid

Compound 66

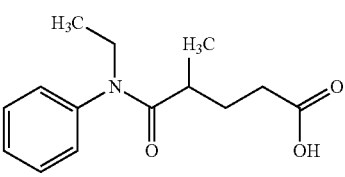

5-[ethyl(phenyl)amino]-4-methyl-5-oxopentanoic acid

Compound 67

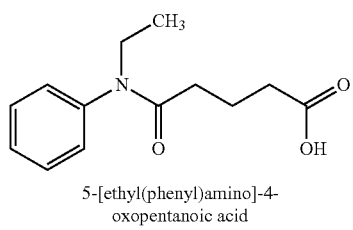

5-[ethyl(phenyl)amino]-4-oxopentanoic acid

Compound 68

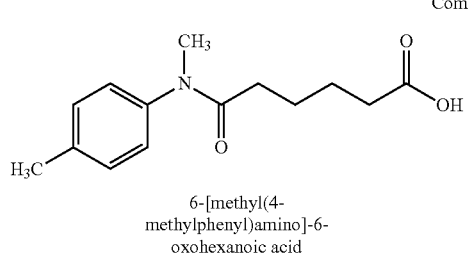

6-[methyl(4-methylphenyl)amino]-6-oxohexanoic acid

Compound 69

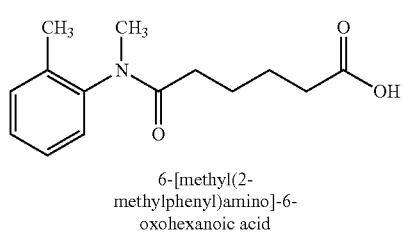

6-[methyl(2-methylphenyl)amino]-6-oxohexanoic acid

Compound 70

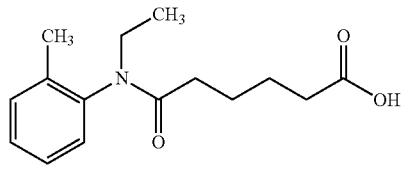

6-[ethyl(2-methylphenyl)amino]-6-oxohexanoic acid

Compound 71

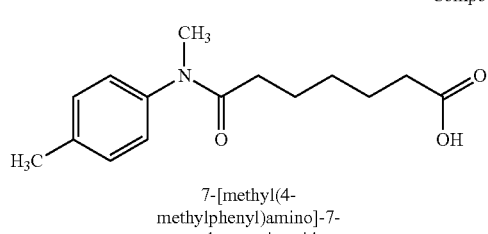

7-[methyl(4-methylphenyl)amino]-7-oxoheptanoic acid

Compound 72

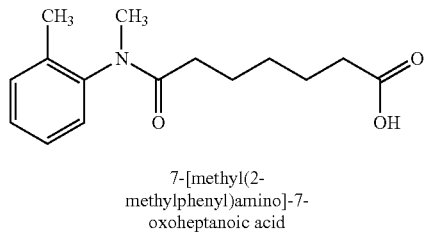

7-[methyl(2-methylphenyl)amino]-7-oxoheptanoic acid

Compound 73

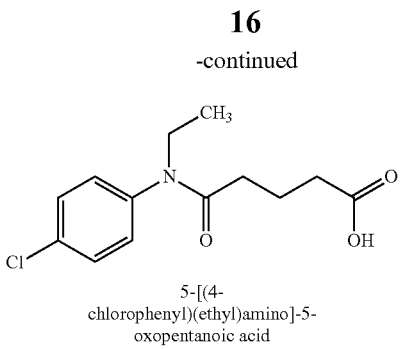

5-[(4-chlorophenyl)(ethyl)amino]-5-oxopentanoic acid

Compound 74

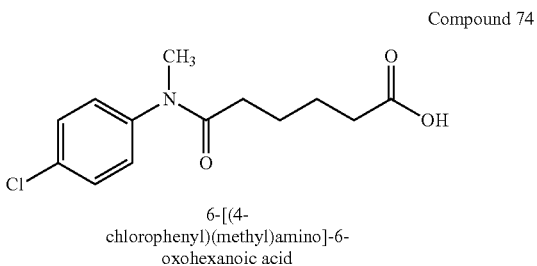

6-[(4-chlorophenyl)(methyl)amino]-6-oxohexanoic acid

Compound 75

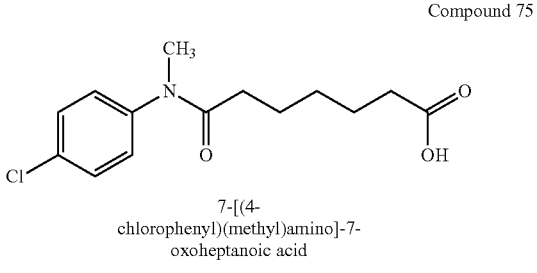

7-[(4-chlorophenyl)(methyl)amino]-7-oxoheptanoic acid

Compound 76

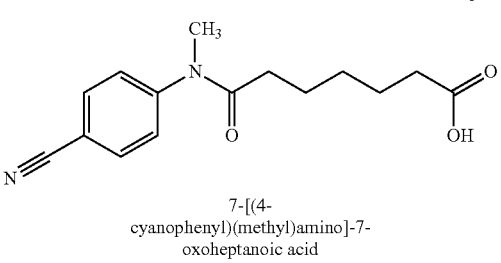

7-[(4-cyanophenyl)(methyl)amino]-7-oxoheptanoic acid

Compound 77

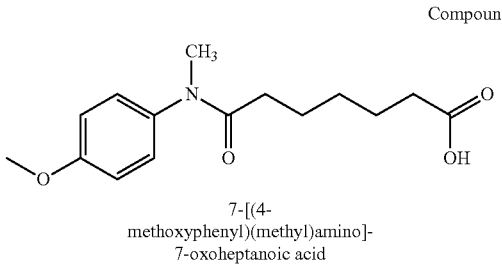

7-[(4-methoxyphenyl)(methyl)amino]-7-oxoheptanoic acid

Compound 78

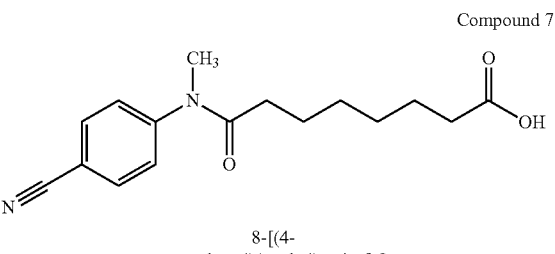

8-[(4-cyanophenyl)(methyl)amino]-8-oxooctanoic acid

Compound 79

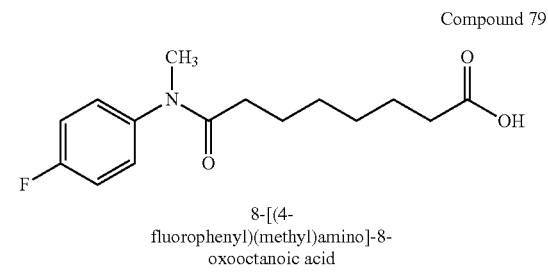

8-[(4-fluorophenyl)(methyl)amino]-8-oxooctanoic acid

Compound 80

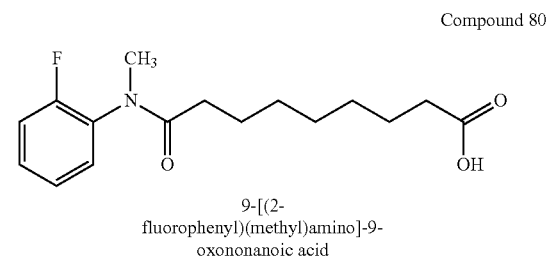

9-[(2-fluorophenyl)(methyl)amino]-9-oxononanoic acid

Compound 81

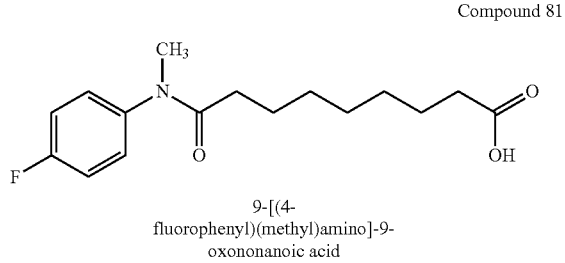

9-[(4-fluorophenyl)(methyl)amino]-9-oxononanoic acid

Compound 82

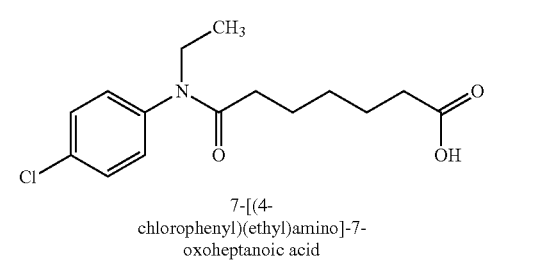

7-[(4-chlorophenyl)(ethyl)amino]-7-oxoheptanoic acid

Compound 82

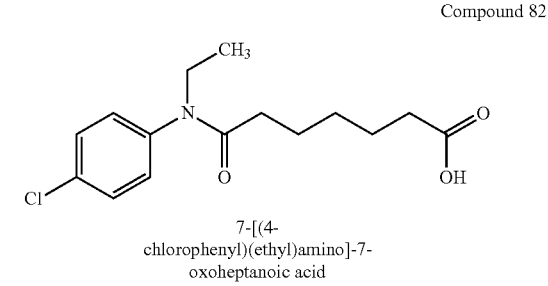

7-[(4-chlorophenyl)(ethyl)amino]-7-oxoheptanoic acid

Compound 83

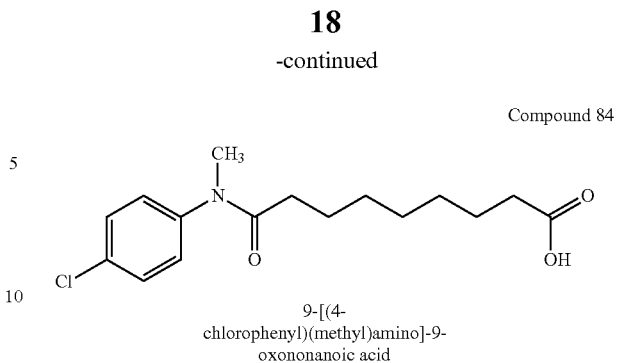

8-[(4-chlorophenyl)(methyl)amino]-8-oxooctanoic acid

Compound 84

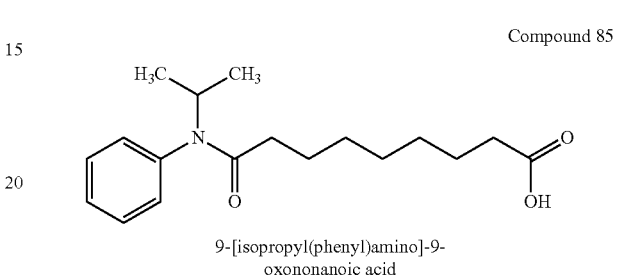

9-[(4-chlorophenyl)(methyl)amino]-9-oxononanoic acid

Compound 85

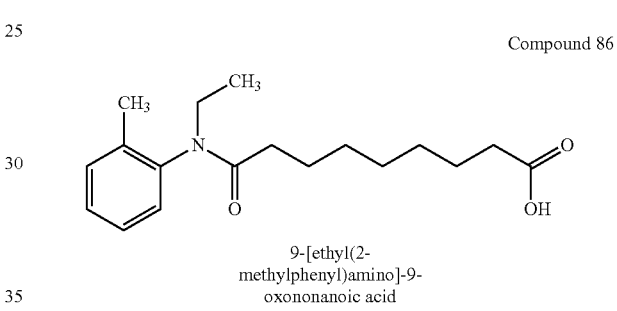

9-[isopropyl(phenyl)amino]-9-oxononanoic acid

Compound 86

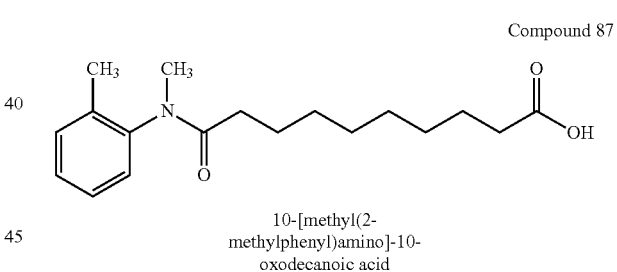

9-[ethyl(2-methylphenyl)amino]-9-oxononanoic acid

Compound 87

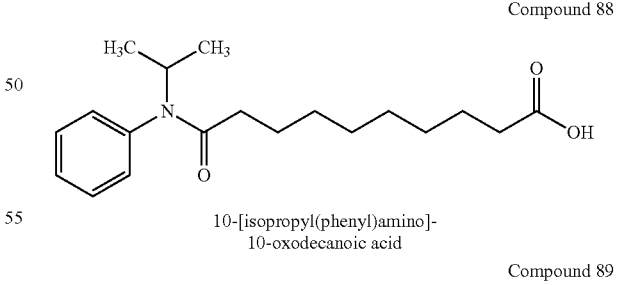

10-[methyl(2-methylphenyl)amino]-10-oxodecanoic acid

Compound 88

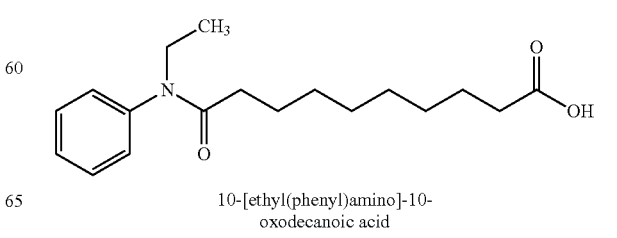

10-[isopropyl(phenyl)amino]-10-oxodecanoic acid

Compound 89

10-[ethyl(phenyl)amino]-10-oxodecanoic acid

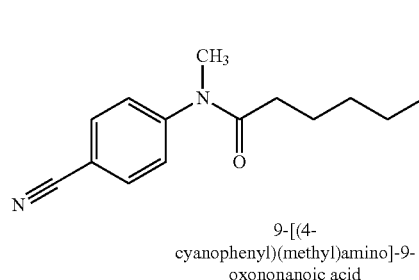

Compound 90

9-[(4-cyanophenyl)(methyl)amino]-9-oxononanoic acid

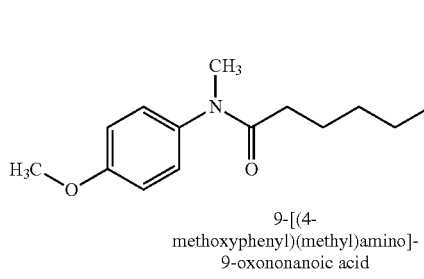

Compound 91

9-[(4-methoxyphenyl)(methyl)amino]-9-oxononanoic acid

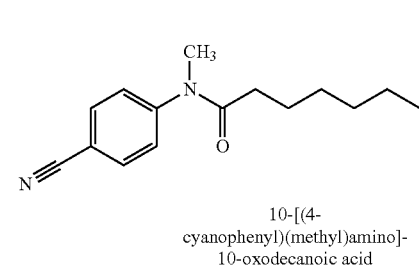

Compound 92

10-[(4-cyanophenyl)(methyl)amino]-10-oxodecanoic acid

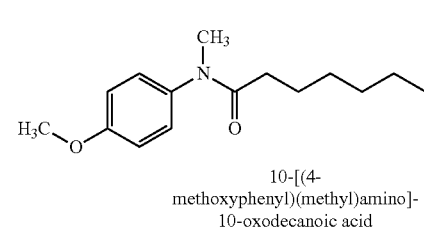

Compound 93

10-[(4-methoxyphenyl)(methyl)amino]-10-oxodecanoic acid

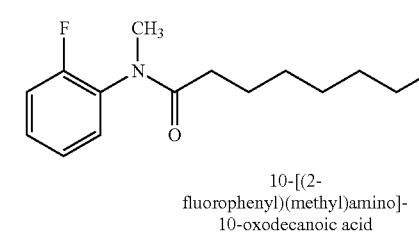

Compound 94

10-[(2-fluorophenyl)(methyl)amino]-10-oxodecanoic acid

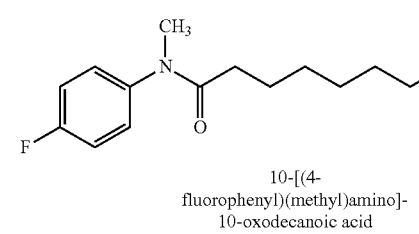

Compound 95

10-[(4-fluorophenyl)(methyl)amino]-10-oxodecanoic acid

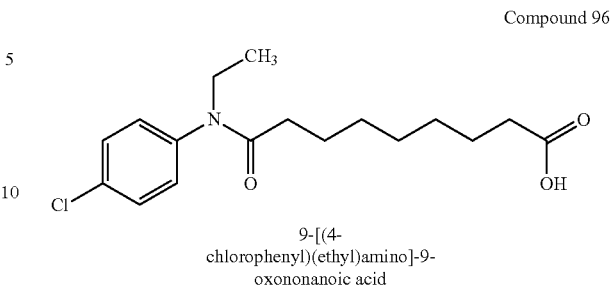

Compound 96

9-[(4-chlorophenyl)(ethyl)amino]-9-oxononanoic acid

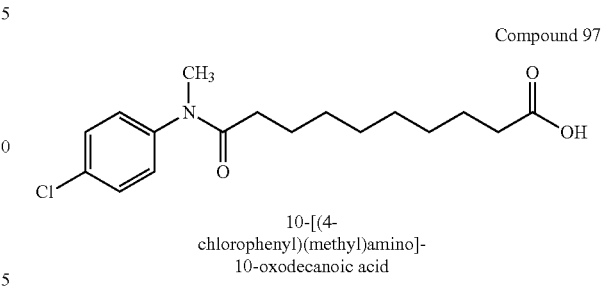

Compound 97

10-[(4-chlorophenyl)(methyl)amino]-10-oxodecanoic acid

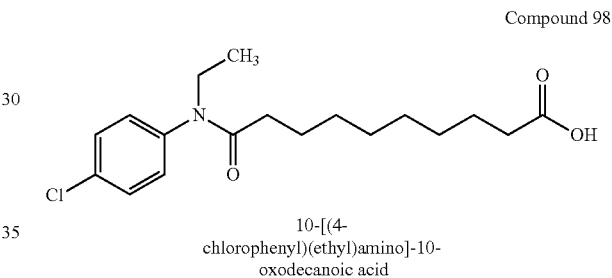

Compound 98

10-[(4-chlorophenyl)(ethyl)amino]-10-oxodecanoic acid

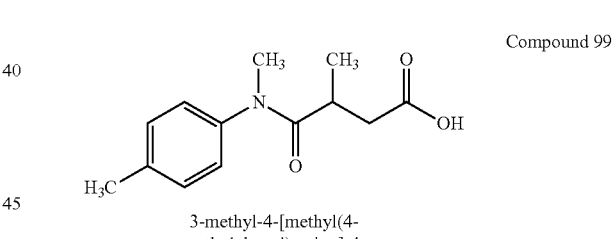

Compound 99

3-methyl-4-[methyl(4-methylphenyl)amino]-4-oxobutanoic acid

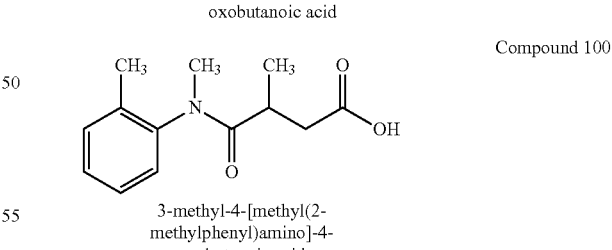

Compound 100

3-methyl-4-[methyl(2-methylphenyl)amino]-4-oxobutanoic acid

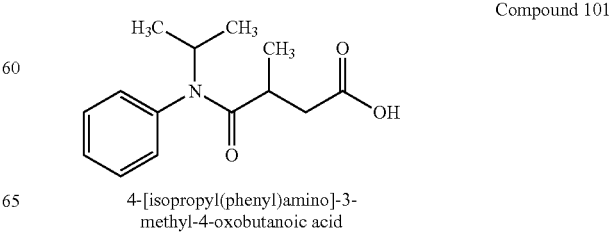

Compound 101

4-[isopropyl(phenyl)amino]-3-methyl-4-oxobutanoic acid

Compound 102

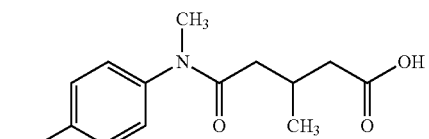

3-methyl-5-[methyl(4-methylphenyl)amino]-5-oxopentanoic acid

Compound 103

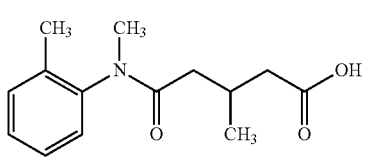

3-methyl-5-[methyl(2-methylphenyl)amino]-5-oxopentanoic acid

Compound 104

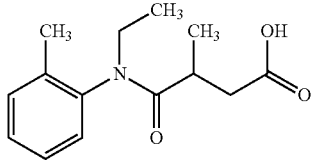

4-[ethyl(2-methylphenyl)amino]-3-methyl 4-oxobutanoic acid

Compound 105

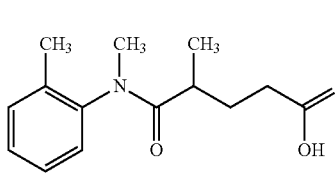

4-methyl-5-[methyl(4-methylphenyl)amino]-5-oxopentanoic acid

Compound 106

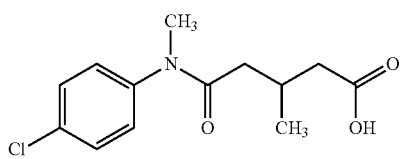

4-methyl-5-[methyl(2-methylphenyl)amino]-5-oxopentanoic acid

Compound 107

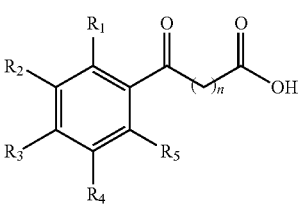

5-[(4-chlorophenyl)(methyl)amino]-3-methyl-5-oxopentanoic acid

Compound 108

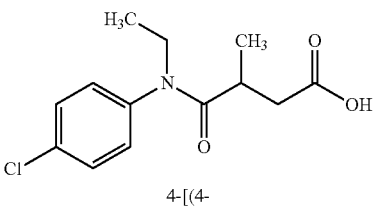

4-[(4-chlorophenyl)(ethyl)amino]-3-methyl-4-

Compound 109

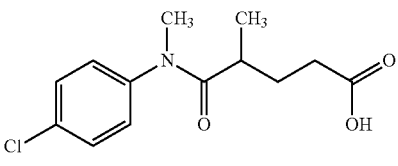

5-[(4-chlorophenyl)(methyl)amino]-4-methyl-5-oxopentanoic acid

Compound 110

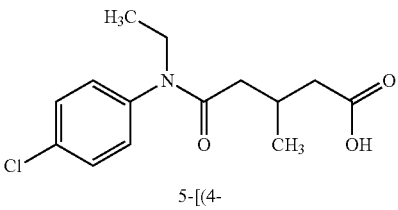

5-[(4-chlorophenyl)(ethyl)amino]-3-methyl-5-oxopentanoic acid

Other delivery agent compounds of the present invention include those of the formula:

(Compound C)

and pharmaceutically acceptable salts thereof, wherein
n=1 to 9, and
$R_1$ to $R_5$ are independently hydrogen, $C_1$ to $C_4$ alkyl, $C_1$ to $C_4$ alkoxy, $C_2$ to $C_4$ alkenyl, halogen, hydroxyl, —NH—C(O)—$CH_3$, or —O—$C_6H_5$.

Preferred delivery agent compounds include, but are not limited to those having the following formulas and salts thereof:

In one embodiment, n=2-8.
In another embodiment, n=8.
In another embodiment, n=7.
In another embodiment, n=6.
In another embodiment, n=5.
In another embodiment, n=4.
In another embodiment, n=3.
In another embodiment, n=2 and the remaining R groups are hydrogen.
In another embodiment, n=8 and the remaining R groups are hydrogen.
In another embodiment, n=7 and the remaining R groups are hydrogen.

In another embodiment, n=6 and the remaining R groups are hydrogen.

In another embodiment, n=5 and the remaining R groups are hydrogen.

In another embodiment, n=4 and the remaining R groups are hydrogen.

In another embodiment, n=3 and the remaining R groups are hydrogen.

In another embodiment, n=2 and the remaining R groups are hydrogen.

In another embodiment, R1 and R5 are hydrogen.
In another embodiment, R1 and R5 are hydrogen and n=2
In another embodiment, R3 is a hydroxyl
In another embodiment, R3 is a hydroxyl and N=8
In another embodiment, R1 is a hydroxyl
In another embodiment, R1 is a hydroxyl and N=8
In another embodiment, R3 is methoxy
In another embodiment, R3 is methoxy and N=2
In another embodiment, R3 is methoxy and N=3
In another embodiment, R2 and R4 are halogens and N=2
In another embodiment R2 and R4 are flourines
In another embodiment R2 and R4 are flourines and N=2
In another embodiment, R1 and R3 are methyl
In another embodiment, R1 and R3 are methyl and N=2
In another embodiment, R2 and R4 are methyl, R3 is a methoxy and N=4
In another embodiment, R3 is an isopropyl
In another embodiment, R3 is an isopropyl and N=3
In another embodiment, R1 is an methoxy
In another embodiment, R1 is an methoxy and N=2
In another embodiment, R3 is a halogen
In another embodiment, R3 is a halogen and N=2
In another embodiment, R3 is an fluorine and N=2
In another embodiment, R3 is a methoxy
In another embodiment, R3 is a methoxy and N=4
In another embodiment, R2 and R4 are methyl
In another embodiment, R2 and R4 are methyl and N=2
In another embodiment, R2 and R4 are methyl and N=4
In another embodiment, R2 and R4 are methyl and N=6
In another embodiment, R2 and R3 are methyl and N=4
In another embodiment, R2 and R3 are methyl and N=2
In another embodiment, R1 and R4 are methyl and N=2
In another embodiment, R1 and R4 are halogens
In another embodiment, R1 and R4 are halogens and N=2
In another embodiment, R1 and R4 are halogens and N=4
In another embodiment, R1 and R4 are chlorines
In another embodiment, R1 and R4 are chlorines and N=2
In another embodiment, R1 and R4 are chlorines and N=4
In another embodiment, R1 and R4 are hydroxyl
In another embodiment, R1 and R4 are hydroxyl and N=8

In one embodiment, compounds 117, 118, 119, 120, 121, 122, 123, 124, 125, 126, 128, 129, 130, 132, 133, 134, 136 and/or 138 or excluded from compound C.

Preferred compounds include, but are not limited to, those shown below.

Compound 111

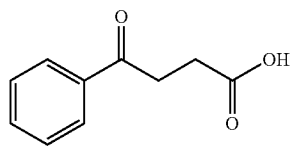

-continued

Compound 112

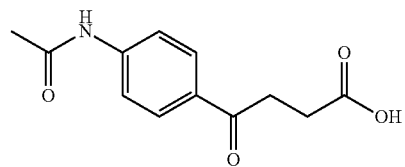

Compound 113

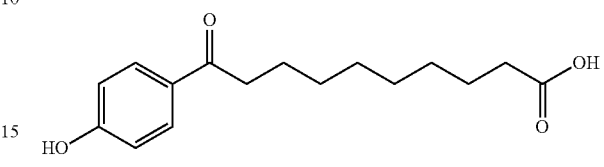

Compound 114

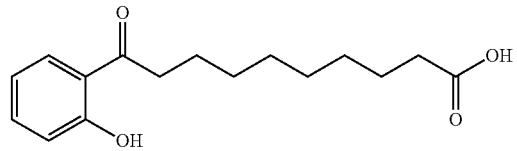

Compound 115

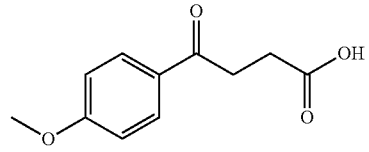

Compound 116

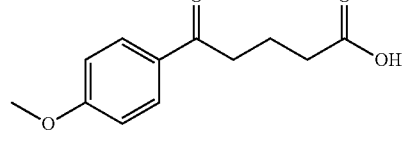

Compound 117

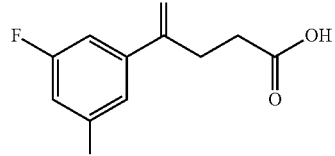

Compound 118

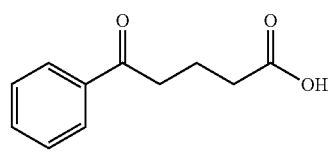

Compound 119

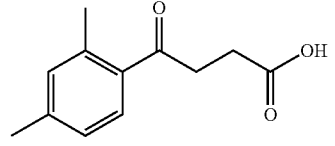

Compound 120

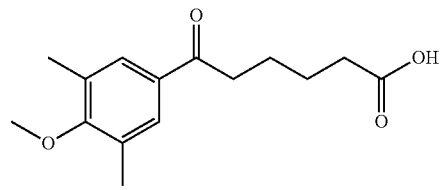

-continued

Compound 121
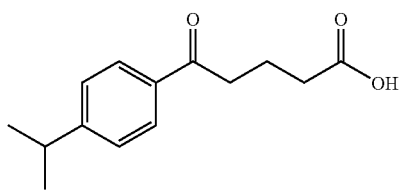

Compound 122
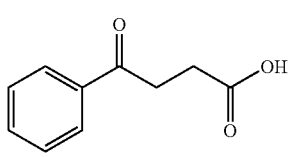

Compound 123
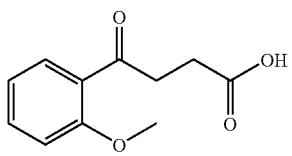

Compound 124
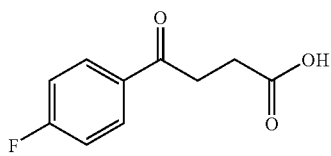

Compound 125
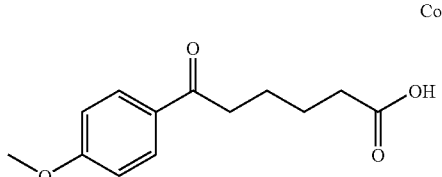

Compound 126
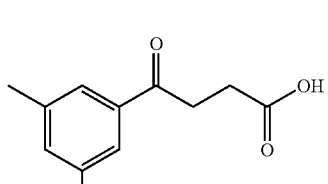

Compound 128
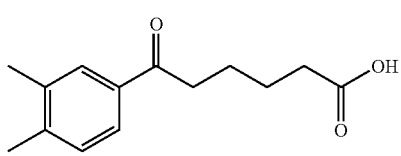

Compound 129
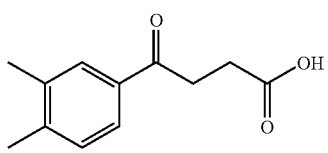

Compound 130
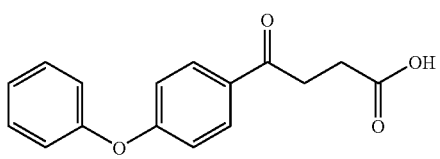

-continued

Compound 132
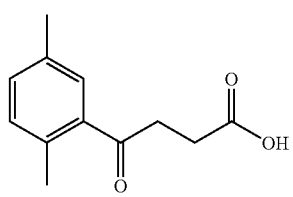

Compound 133
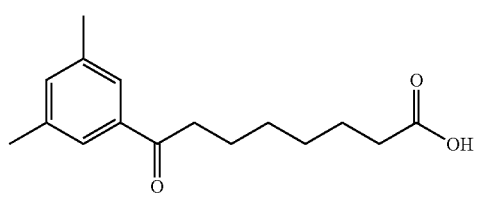

Compound 134
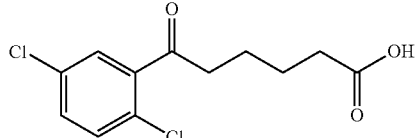

Compound 136
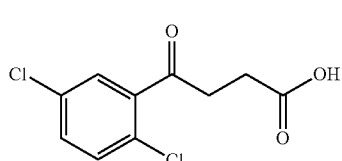

Compound 138
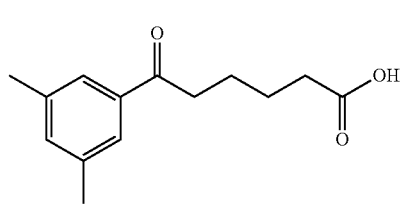

Other delivery agent compounds of the present invention include those of the formula:

(Compound D)
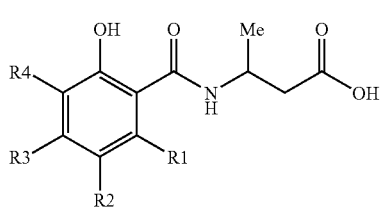

and pharmaceutically acceptable salts thereof, wherein
R1 to R4 are independently hydrogen, $C_1$ to $C_4$ alkyl, $C_2$ to $C_4$ alkenyl, halogen, $C_1$ to $C_4$ alkoxy, or hydroxyl.

In one embodiment, R1 to R4 are independently hydrogen, methyl, methoxy, halogen, or isopropyl.

In one embodiment, R1 to R4 are all hydrogen.

In another embodiment R2 and R4 are halogens, preferably bromine or preferably chlorine, or preferably iodine, or preferably fluorine.

In another embodiment R2 and R4 are halogens, preferably bromine or preferably chlorine, or preferably iodine, and R1 and R3 are hydrogen.

In another preferred embodiment R2 and R4 are isopropyl.

In another preferred embodiment R2 and R4 are isopropyl, and R1 and R3 are hydrogen.

In another preferred embodiment R4 is a methyl.

In another preferred embodiment R4 is a methyl and R1 to R3 are hydrogen.

In another preferred embodiment R3 is a halogen, preferably chlorine.

In another preferred embodiment R3 is a halogen, preferably chlorine and R1, R2 and R4 are hydrogens.

In another preferred embodiment R3 is a methoxy.

In another preferred embodiment R3 is a methoxy, and R1, R2 and R4 are hydrogens.

in another preferred embodiment R2 is a halogen, preferably bromine.

In another preferred embodiment R2 is a halogen, preferably bromine, and R1, R2 and R4 are hydrogens.

In another preferred embodiment R2 is a halogen, preferably chlorine.

In another preferred embodiment R2 is a halogen, preferably chlorine, and R1, R3 and R4 are hydrogens.

In another preferred embodiment R2 is a methoxy.

In another preferred embodiment R2 is a methoxy, and R1, R3 and R4 are hydrogens.

In another preferred embodiment R2 is a methyl.

In another preferred embodiment R2 is a methyl, and R1, R3 and R4 are hydrogens.

Preferred delivery agent compounds include, but are not limited to those having the following formulas and salts thereof:

Compound 140

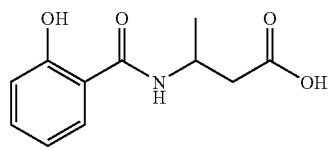

3-(2-Hydroxy-benzoylamino)-butyric acid

Compound 141

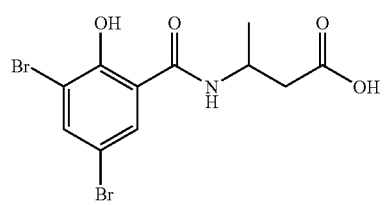

3-(3,5-Dibromo-2-hydroxy-benzoylamino)-butyric acid

Compound 142

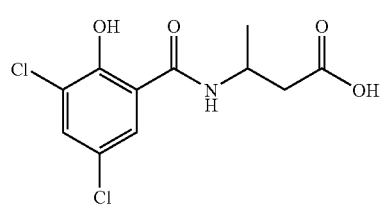

3-(3,5-Dichloro-2-hydroxy-benzoylamino)-butyric acid

Compound 143

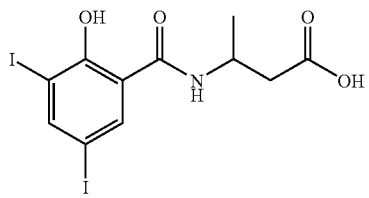

3-(2-Hydroxy-3,5-diiodo-benzoylamino)-butyric acid

Compound 144

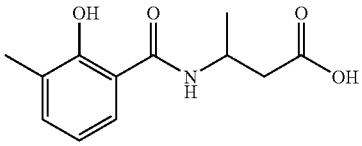

3-(2-Hydroxy-3-methyl-benzoylamino)-butyric acid

Compound 145

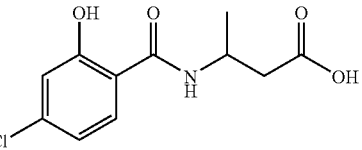

3-(4-Chloro-2-hydroxy-benzoylamino)-butyric acid

Compound 146

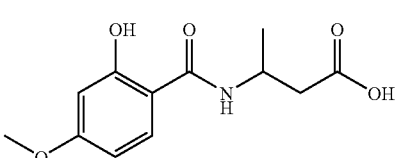

3-(2-Hydroxy-4-methoxy-benzoylamino)-butyric acid

Compound 147

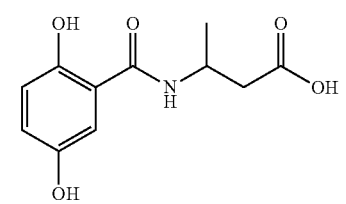

3-(5-Bromo-2-hydroxy-benzoylamino)-butyric acid

Compound 148

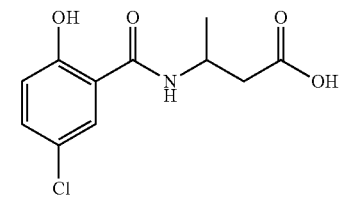

3-(5-Chloro-2-hydroxy-benzoylamino)-butyric acid

Compound 149

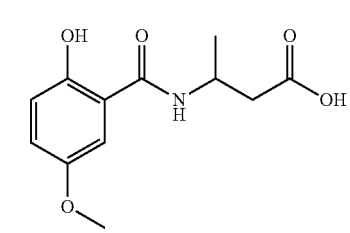

3-(2-Hydroxy-5-methoxy-benzoylamino)-butyric acid

-continued

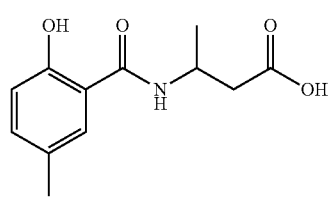

3-(2-Hydroxy-5-methyl-benzoylamino)-butyric acid

Compound 150

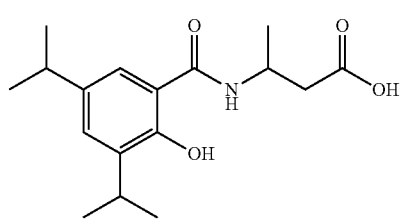

3-(2-hydroxy-3,5-diisopropyl-benzoylamino)-butyric acid

Compound 151

Other delivery agent compounds of the present invention include those of the formula:

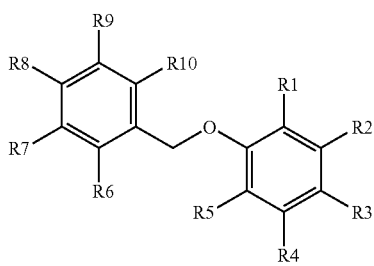

(Compound E)

and pharmaceutically acceptable salts thereof, wherein
one of R1 to R5 has the generic structure

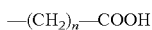
—$(CH_2)_n$—COOH where n=0-6;
the remaining four members of R1 to R5 are independently hydrogen, $C_1$ to $C_4$ alkyl, $C_2$ to $C_4$ alkenyl, halogen, $C_1$ to $C_4$ alkoxy, or hydroxyl; and
R6-R10 are independently hydrogen, $C_1$ to $C_4$ alkyl, $C_2$ to $C_4$ alkenyl, halogen, $C_1$ to $C_4$ alkoxy, or hydroxyl.
In one embodiment, n=0-4.
In another embodiment, n=0.
In another embodiment, n=1.
In another embodiment, R1-R10 are preferably independently hydrogen, halogen, methyl and methoxy.
In another embodiment, R1-R10 are preferably independently chlorine, halogen, methyl and methoxy.
In another embodiment, when the generic structure —$(CH_2)_n$—COOH is attached at R1, rest of the R groups are hydrogen.
In another embodiment, when the generic structure —$(CH_2)_n$—COOH is attached at R1, rest of the R groups are hydrogen and n=0.
In another embodiment, when the generic structure —$(CH_2)_n$—COOH is attached at R1, rest of the R groups are hydrogen and n=1.
In another embodiment, when the generic structure —$(CH_2)_n$—COOH is attached at R3, rest of the R groups are hydrogen.

In another embodiment, when the generic structure —$(CH_2)_n$—COOH is attached at R3, rest of the R groups are hydrogen, and n=0.
In another embodiment, when the generic structure —$(CH_2)_n$—COOH is attached at R3, rest of the R groups are hydrogen.
In another embodiment, when the generic structure —$(CH_2)_n$—COOH is attached at R3, rest of the R groups are hydrogen and n=1.
In another embodiment, R5 is a methoxy when the generic structure —$(CH_2)_n$—COOH is attached at R2.
In another embodiment, R5 is a methoxy when the generic structure —$(CH_2)_n$—COOH is attached at R2, rest of the R groups are hydrogen.
In another embodiment, R5 is a methoxy when the generic structure —$(CH_2)_n$—COOH is attached at R2, and n=0.
In another embodiment, R5 is a methoxy when the generic structure —$(CH_2)_n$—COOH is attached at R2, and n=0, rest of the R groups are hydrogen.
In another embodiment, R1 and R5 are methyl when the generic structure —$(CH_2)_n$—COOH is attached at R3.
In another embodiment, R1 and R5 are methyl when the generic structure —$(CH_2)_n$—COOH is attached at R3, rest of the R groups are hydrogen.
In another embodiment, R1 and R5 are methyl when the generic structure —$(CH_2)_n$—COOH is attached at R3 and n=0.
In another embodiment, R1 and R5 are methyl when the generic structure —$(CH_2)_n$—COOH is attached at R3 and n=0, rest of the R groups are hydrogen.
In another embodiment, R1 or R5 are methoxy when the generic structure —$(CH_2)_n$—COOH is attached at R3 and n=0.
In another embodiment, R1 or R5 are methoxy when the generic structure —$(CH_2)_n$—COOH is attached at R3 and n=0, rest of the R groups are hydrogen.
In another embodiment, R2 or R4 is a halogen, preferably chlorine when the generic structure —$(CH_2)_n$—COOH is attached at R3.
In another embodiment, R2 or R4 is a halogen, preferably chlorine when the generic structure —$(CH_2)_n$—COOH is attached at R3, rest of the R groups are hydrogen.
In another embodiment, R2 or R4 is a halogen, preferably chlorine when the generic structure —$(CH_2)_n$—COOH is attached at R3 and n=0.
In another embodiment, R2 or R4 is a halogen, preferably chlorine when the generic structure —$(CH_2)_n$—COOH is attached at R3 and n=0, rest of the R groups are hydrogen.
In one embodiment, compounds 152, 153, 154, 155, 156, 157, and/or 158 are excluded from compound E.
Preferred compounds include, but are not limited to, the following compounds and pharmaceutically acceptable salts thereof:

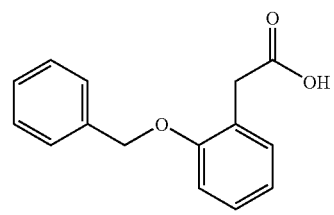

Compound 152

2-Benzyloxyphenyl acetic acid

-continued

Compound 153

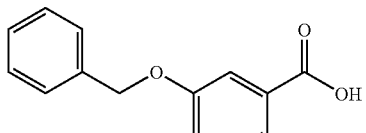

2-Benzyloxy-4-methoxybenzoic acid

Compound 154

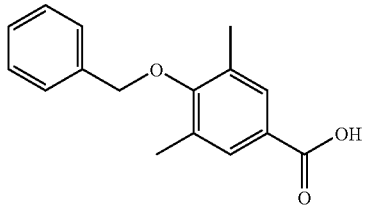

2-Benzyloxy-3,5-dimethylbenzoic acid

Compound 155

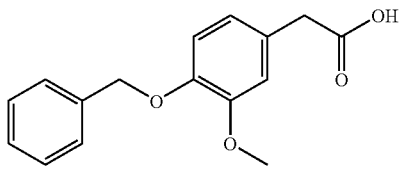

(4-Benzyloxy-3-methoxy-phenyl)-acetic acid

Compound 156

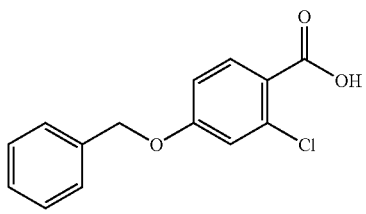

4-(Benzyloxy)-2-chlorobenzoic acid

Compound 157

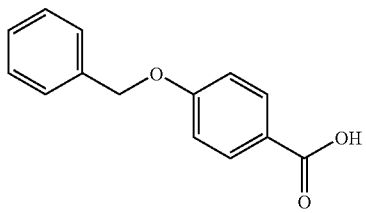

4-Benzyloxy-benzoic acid

Compound 158

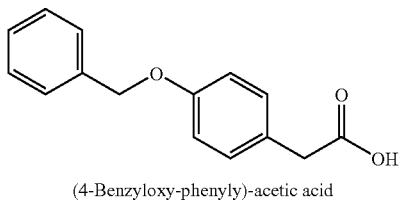

(4-Benzyloxy-phenyly)-acetic acid

Compound 159

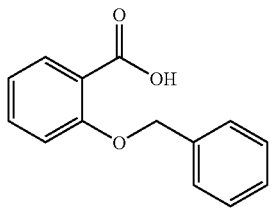

2-Benzyloxybenzoic acid

Other delivery agent compounds of the present invention include those of the formula:

Compound F

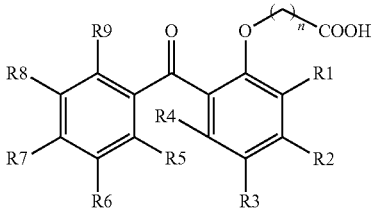

and pharmaceutically acceptable salts thereof, wherein
n=1 to 9; and
$R_1$ to $R_9$ are independently hydrogen, $C_1$ to $C_4$ alkyl, $C_2$ to $C_4$ alkenyl, halogen, $C_1$ to $C_4$ alkoxy, or hydroxyl.

According to one preferred embodiment, n=3-7, preferably, in one preferred embodiment, n=3, preferably, in another preferred embodiment, n=4; preferably, in another preferred embodiment, n=5; preferably, in another preferred embodiment, n=6; preferably, in another preferred embodiment, n=7.

According to another preferred embodiment, $R_1$-$R_8$ is a hydrogen.

According to another preferred embodiment, $R_3$ is a halogen, preferably, in one embodiment, $R_3$ is a chlorine, preferably, in another embodiment, $R_3$ is a bromine.

According to another preferred embodiment, $R_2$ is a methoxy.

According to another preferred embodiment, $R_2$ is a methyl.

According to another preferred embodiment, $R_3$ is a methoxy.

According to another preferred embodiment, $R_3$ is a methyl.

According to another preferred embodiment, $R_6$ is a methoxy.

According to another preferred embodiment, $R_9$ is a hydrogen.

According to another preferred embodiment, $R_9$ is a hydroxyl.

According to another preferred embodiment, $R_9$ is a halogen, preferably, in one embodiment chlorine.

According to another preferred embodiment, $R_3$ and $R_6$ are both a methoxy.

According to another preferred embodiment, $R_3$ and $R_6$ are both a methoxy and the remaining R groups are hydrogen.

According to another preferred embodiment, $R_2$ is a methyl and $R_3$ is a chlorine.

According to another preferred embodiment, $R_2$ is a methyl and $R_3$ is a chlorine and the remaining R groups are hydrogen.

According to another preferred embodiment, $R_2$ is a methyl and $R_9$ is a chlorine.

According to another preferred embodiment, $R_2$ is a methyl and $R_9$ is a chlorine and the remaining R groups are hydrogen.

According to another preferred embodiment, $R_3$ is a methyl and $R_9$ is a chlorine.

According to another preferred embodiment, $R_3$ is a methyl and $R_9$ is a chlorine and the remaining R groups are hydrogen.

Preferred delivery agent compounds include, but are not limited to those having the following formulas and salts thereof:

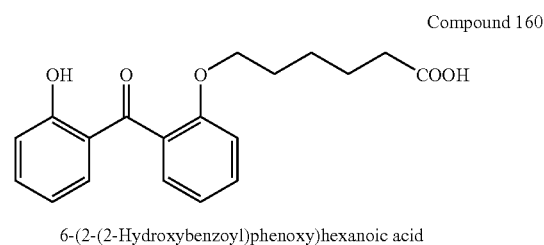

Compound 160

6-(2-(2-Hydroxybenzoyl)phenoxy)hexanoic acid

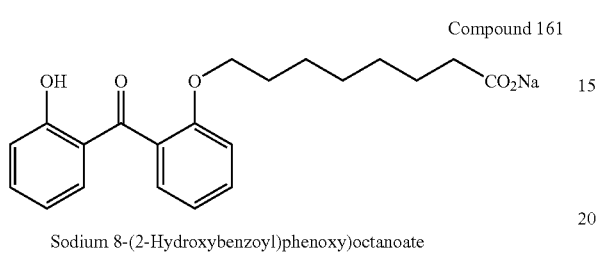

Compound 161

Sodium 8-(2-Hydroxybenzoyl)phenoxy)octanoate

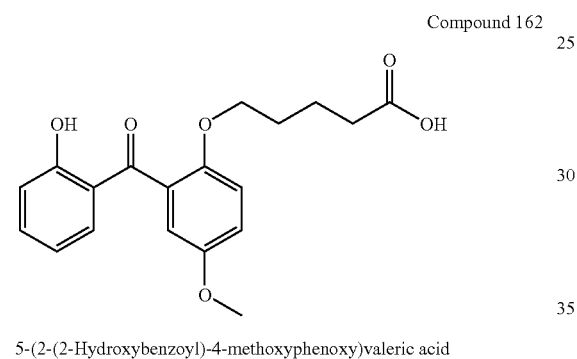

Compound 162

5-(2-(2-Hydroxybenzoyl)-4-methoxyphenoxy)valeric acid

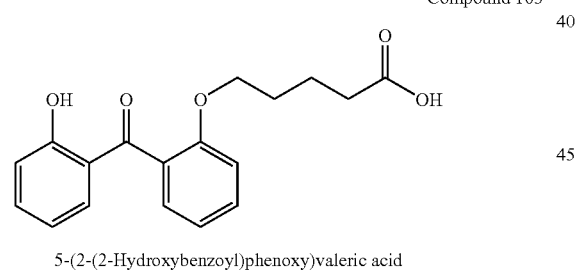

Compound 163

5-(2-(2-Hydroxybenzoyl)phenoxy)valeric acid

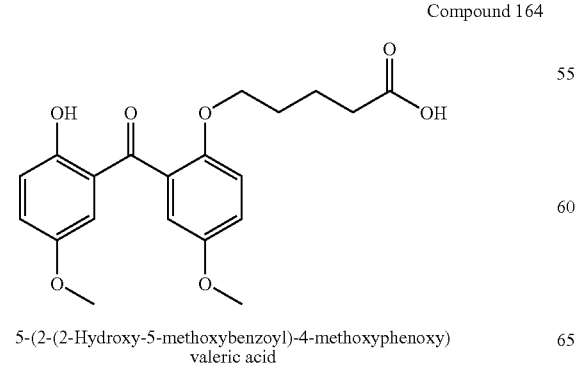

Compound 164

5-(2-(2-Hydroxy-5-methoxybenzoyl)-4-methoxyphenoxy) valeric acid

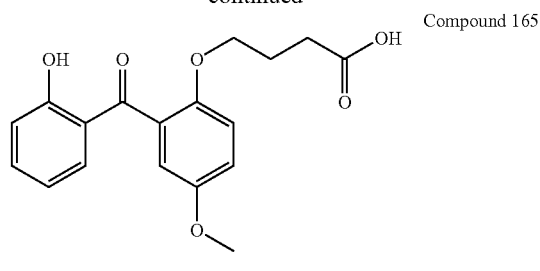

Compound 165

4-(2-(2-Hydroxybenzoyl)-5-methoxyphenoxy) butyric acid

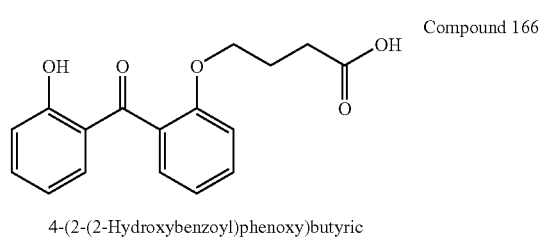

Compound 166

4-(2-(2-Hydroxybenzoyl)phenoxy)butyric

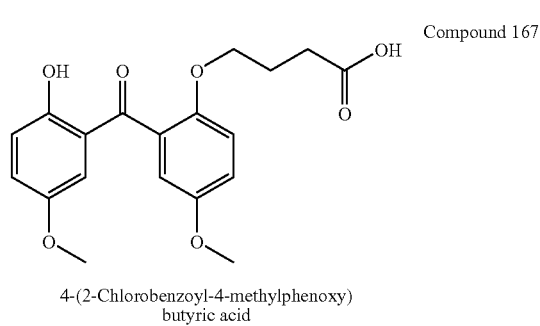

Compound 167

4-(2-Chlorobenzoyl-4-methylphenoxy) butyric acid

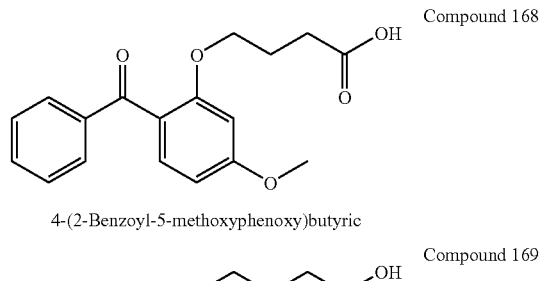

Compound 168

4-(2-Benzoyl-5-methoxyphenoxy)butyric

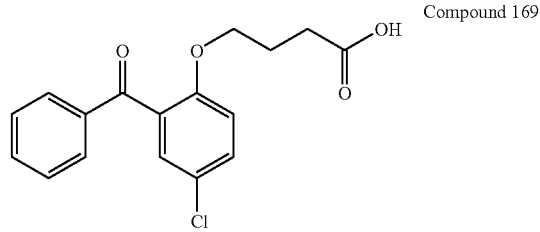

Compound 169

4-(2-Benzoyl-4-chlorophenoxy)butyric acid

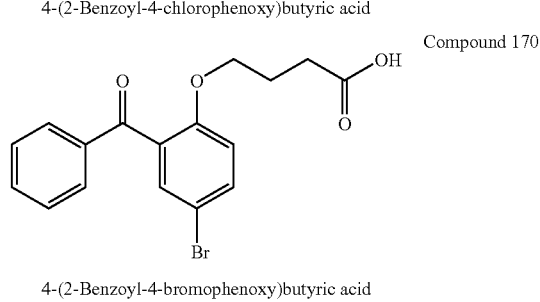

Compound 170

4-(2-Benzoyl-4-bromophenoxy)butyric acid

Compound 171

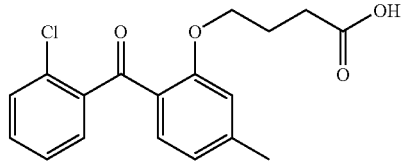

4-(2-(2-Chlorobenzoyl-5-methylphenoxy)butyric acid

Compound 172

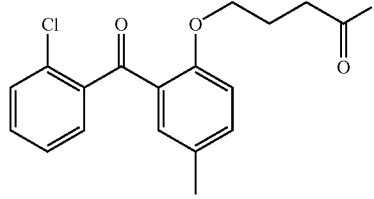

4-(2-(2-Chlorobenzoyl-4-methylphenoxy)
butyric acid

Compound 173

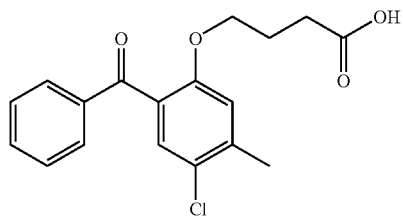

4-(2-Benzoyl-4-chloro-5-methylphenoxy)
butyric acid

Compound 174

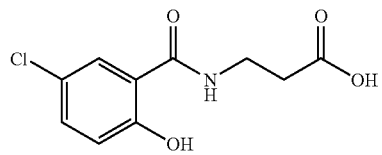

Other delivery agent compounds of the present invention include those of the formula:

(Compound G)

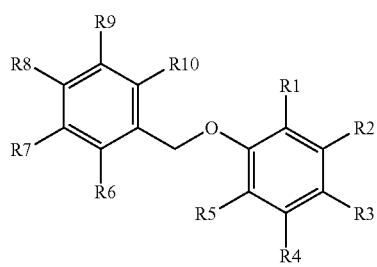

and pharmaceutically acceptable salts thereof, wherein

R1-R5 are independently hydrogen, $C_1$ to $C_4$ alkyl, $C_2$ to $C_4$ alkenyl, halogen, $C_1$ to $C_4$ alkoxy, hydroxyl, or —O—$(CH_2)_n$—COOH (where n is 1 to 12);

at least one of $R_1$ to $R_5$ has the generic structure

—O—$(CH_2)_n$—COOH where n=1-12; and

R6-R10 are independently hydrogen, $C_1$ to $C_4$ alkyl, $C_2$ to $C_4$ alkenyl, halogen, $C_1$ to $C_4$ alkoxy, or hydroxyl.

Preferably, only one of R1 to R5 has the formula —O—$(CH_2)_n$—COOH. In other words, four members of R1 to R5 are independently hydrogen, $C_1$ to $C_4$ alkyl, $C_2$ to $C_4$ alkenyl, halogen, $C_1$ to $C_4$ alkoxy, or hydroxyl, and the remaining member of R1 to R5 is —O—$(CH_2)_n$—COOH (where n is 1-12).

In one preferred embodiment n=1-12.

In another preferred embodiment n=1-10.

In another preferred embodiment n=1-6.

In another preferred embodiment n=1-4.

In another preferred embodiment n=10.

In another preferred embodiment n=4.

In another preferred embodiment n=1.

When the generic structure —$(CH_2)_n$—COOH is attached at R1, all other R groups are hydrogen.

When the generic structure —$(CH_2)_n$—COOH is attached at R1, all other R groups are hydrogen and n=3.

When the generic structure —$(CH_2)_n$—COOH is attached at R3, all other R groups are hydrogen.

When the generic structure —$(CH_2)_n$—COOH is attached at R3, all other R groups are hydrogen and n=1.

When the generic structure —$(CH_2)_n$—COOH is attached at R3, all other R groups are hydrogen and n=4.

When the generic structure —$(CH_2)_n$—COOH is attached at R3, all other R groups are hydrogen and n=10.

Preferred compounds include, but are not limited to, the following compounds and pharmaceutically acceptable salts thereof:

Compound 175

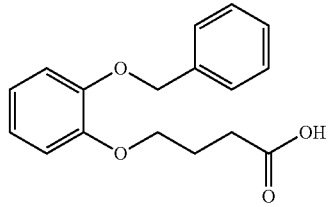

4-(2-Benzyloxy-phenyl)-butyric acid

Compound 176

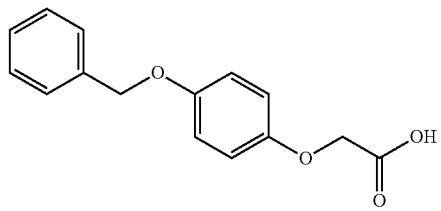

(4-Benzyloxy-phenoxy)-acetic acid

Compound 177

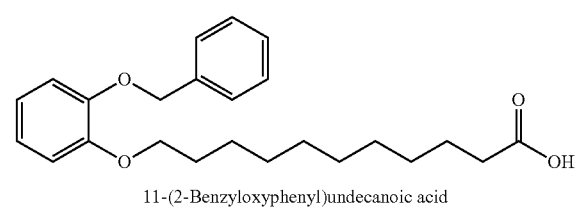

11-(2-Benzyloxyphenyl)undecanoic acid

Compound 178

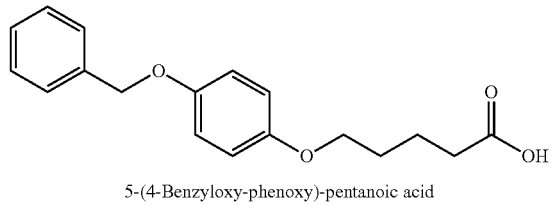

5-(4-Benzyloxy-phenoxy)-pentanoic acid

Mixtures of these delivery agent compounds may also be used.

The invention also provides a composition comprising the delivery agent compound of the present invention, and at least one active agent. These compositions deliver active agents to selected biological systems in increased or improved bioavailability of the active agent compared to administration of the active agent without the delivery agent compound.

Also provided are dosage unit forms comprising the compositions. The dosage unit may be in the form of a liquid or a solid, such as a tablet, capsule or particle, including a powder or sachet.

Another embodiment is a method for administering an active agent to an animal, by administering a composition comprising at least one of the delivery agent compounds of the present invention and the active agent to the animal. Routes of administration include the oral, intracolonic and pulmonary routes.

Yet another embodiment is a method of treating a disease or for achieving a desired physiological effect in an animal by administering the composition of the present invention.

Yet another embodiment is administering the composition of the present invention to an animal that would benefit from the composition and/or to an animal in need of the active agent.

Yet another embodiment is a method of preparing a composition of the present invention by mixing at least one delivery agent compound of the present invention, and at least one active agent.

DETAILED DESCRIPTION OF THE INVENTION

Definitions

As used herein and in the appended claims, the singular forms "a," "an," and "the," include plural referents unless the context clearly indicates otherwise. Thus, for example, reference to "a molecule" includes one or more of such molecules, "a reagent" includes one or more of such different reagents, and reference to "the method" includes reference to equivalent steps and methods known to those of ordinary skill in the art that could be modified or substituted for the methods described herein.

The term "polymorph" refers to a crystallographically distinct form of a substance.

The term "hydrate" as used herein includes, but is not limited to, (i) a substance containing water combined in the molecular form and (ii) a crystalline substance containing one or more molecules of water of crystallization or a crystalline material containing free water.

The term "solvate" as used herein includes, but is not limited to, a molecular or ionic complex of molecules or ions of a solvent with molecules or ions of delivery agent.

The term "delivery agent" refers to any of the delivery agent compounds disclosed or incorporated by reference herein, including their pharmaceutically acceptable salts.

An "effective amount of the pharmaceutical composition" is an amount of the pharmaceutical composition described which is effective to treat or prevent a condition in a subject to whom it is administered over some period of time, e.g., provides a therapeutic effect during a desired dosing interval.

The term "treat", "treating", or "treated" refers to prophylactically preventing, curing, healing, alleviating, relieving, altering, remedying, ameliorating, improving, or affecting a condition (e.g., a disease), the symptoms of the condition, or the predisposition toward the condition.

An "effective amount of delivery agent" is an amount of the delivery agent which promotes the absorption of a desired amount of the active agent.

The term "subject" includes mammals, such as rodents, cows, pigs, dogs, cats, primates, and particularly humans.

The term "AUC" as used herein, means area under the plasma concentration-time curve, as calculated by the trapezoidal rule over the complete dosing interval, e.g., 24-hour interval.

The term "mean", when preceding a pharmacokinetic value (e.g., mean Peak), represents the arithmetic mean value of the pharmacokinetic value unless otherwise specified.

As used herein, the term "about" means within 10% of a given value, preferably within 5%, and more preferably within 1% of a given value. Alternatively, the term "about" means that a value can fall within a scientifically acceptable error range for that type of value, which will depend on how qualitative a measurement can be given by the available tools.

"Indication" means the use for which the drug is administered either to prevent or to treat a condition, and may be used interchangeably with "treat", "treated" or "treating".

The term "substituted" as used herein includes, but is not limited to, substitution with any one or any combination of the following substituents: halogens, hydroxide, $C_1$-$C_4$ alkyl, and $C_1$-$C_4$ alkoxy.

The terms "alkyl", "alkoxy", "alkylene", "alkenylene", "alkyl(arylene)", and "aryl(alkylene)" include, but are not limited to, linear and branched alkyl, alkoxy, alkylene, alkenylene, alkyl(arylene), and aryl(alkylene) groups, respectively.

By "peptide YY" or "PYY" is meant a Peptide YY polypeptide obtained or derived from any species. Thus, the term "PYY" includes both the human full length, 36 amino acid peptide as set forth in SEQ ID NO: 2 of International Publication No. WO 02/47712 (which is the PCT counterpart to U.S. Patent Publication No. 2002/0141985, which is hereby incorporated by reference) and Tatemoto, Proc Natl Acad Sci U.S.A. 79:2514-8, 1982, and species variations of PYY, including e.g., murine, hamster, chicken, bovine, rat, and dog PYY, for example. By "PYY agonist" is meant any compound which elicits an effect of PYY to reduce nutrient availability, for example a compound (1) having activity in the food intake, gastric emptying, pancreatic secretion, or weight loss assays described in Examples 1, 2, 5, or 6 of WO 02/47712 and U.S. Patent Publication No. 2002/0141985, and (2) which binds specifically in a Y receptor assay (Example 10 of WO 02/47712 and U.S. Patent Publication No. 2002/0141985) or in a competitive binding assay with labeled PYY or PYY [3-36] from certain tissues having an abundance of Y receptors, including e.g., area postrema (Example 9 of WO 02/47712 and U.S. Patent Publication No. 2002/0141985), wherein the PYY agonist is not pancreatic polypeptide. Preferably, PYY agonists would bind in such assays with an affinity of greater than about 1 µM, and more preferably with an affinity of greater than about 1 to about 5 nM.

Such agonists can comprise a polypeptide having a functional PYY domain, an active fragment of PYY, or a chemical or small molecule. PYY agonists may be peptide or nonpeptide compounds, and include "PYY agonist analogs," which refer to any compound structurally similar to a PYY that have PYY activity typically by virtue of binding to or otherwise directly or indirectly interacting with a PYY receptor or other receptor or receptors with which PYY itself may interact to elicit a biological response. Such compounds include derivatives of PYY, fragments of PYY, extended PYY molecules having more than 36 amino acids, truncated PYY molecules having less than 36 amino acids, and substituted PYY molecules having one or more different amino acids, or any combination of the above. Such compounds may also be modified by processes such as pegylation, amidation, glycosylation, acylation, sulfation, phosphorylation, acetylation and cyclization.

One such PYY agonist analog is PYY [3-36], identified as SEQ ID NO 3 of WO 02/47712 and U.S. Patent Publication No. 2002/0141985; Eberlein, Eysselein et al., *Peptides* 10:797-803 (1989); and Grandy, Schimiczek et al., *Regul Pept* 51:151-9 (1994). Polypeptides with numbers in brackets refer to truncated polypeptides having the sequence of the full length peptide over the amino acid positions in the brackets. Thus, PYY [3-36] has a sequence identical to PYY over amino acids 3 to 36. PYY[3-36] contains approximately 40% of total peptide YY-like immunoreactivity in human and canine intestinal extracts and about 36% of total plasma peptide YY immunoreactivity in a fasting state to slightly over 50% following a meal. It is apparently a dipeptidyl peptidase-IV (DPP4) cleavage product of peptide YY. Peptide YY[3-36] is reportedly a selective ligand at the Y2 and Y5 receptors, which appear pharmacologically unique in preferring N-terminally truncated (i.e. C terminal fragments of) neuropeptide Y analogs. A PYY agonist may bind to a PYY receptor with higher or lower affinity, demonstrate a longer or shorter half-life in vivo or in vitro, or be more or less effective than native PYY.

Other suitable PYY agonists include those described in International Publication No. WO 98/20885, which is hereby incorporated by reference.

The term "heparin" as used herein refers to all forms of heparin, including, but not limited to, unfractionated heparin, heparinoids, dermatans, chondroitins, low molecular weight heparin (e.g., tinzaparin (including tinzaparin sodium)), very low molecular weight heparin, and ultra low molecular weight heparin. Non-limiting examples include unfractionated heparin, such as heparin sodium (e.g., heparin sodium USP, available from Scientific Protein Labs of Waunakee, Wis.). Heparin generally has a molecular weight of from about 1,000 or 5,000 to about 30,000 Daltons. The term "low molecular weight heparin" generally refers to heparin in which at least about 80% (by weight) of the heparin and has a molecular weight of between about 3000 and about 9000 daltons. Non-limiting examples of low molecular weight heparin include tinzaparin, enoxaprin, and daltiparin. Tinzaparin has been approved by the U.S. Food & Drug Administration for the treatment of acute symptomatic deep vein thrombosis with or without pulmonary embolism when administered in conjunction with warfarin sodium. The sodium salt of from Pharmion Corporation™tinazaparin is available under the trademark Innohep of Boulder, Colo. The term "very low molecular weight heparin" generally refers to heparin in which at least about 80% (by weight) of the heparin has a molecular weight of between about 1500 and about 5000 daltons. A non-limiting example of very low molecular weight heparin is bemiparin. The term "ultra low molecular weight heparin" generally refers to heparin in which at least about 80% (by weight) of the heparin has a molecular weight of between about 1000 and about 2000 daltons. A non-limiting examples of ultra low molecular weight heparin is fondiparinux.

Delivery Agents

The delivery agents of the present invention may be in the free acid or a pharmaceutically acceptable salt form. Suitable pharmaceutically acceptable salts include, but are not limited to, organic and inorganic salts, for example alkali-metal salts, such as sodium, potassium and lithium; alkaline-earth metal salts, such as magnesium, calcium or barium; ammonium salts; basic amino acids, such as lysine or arginine; and organic amines, such as dimethylamine or pyridine. In one embodiment, the salts are sodium salts. The salts may be mono- or multi-valent salts, such as monosodium salts and di-sodium salts. The salts may also be solvates, including ethanol solvates, and hydrates. Non-limiting examples of pharmaceutically acceptable salts include sodium, hydrochloric acid, sulfuric acid, phosphoric acid, citric acid, acetic acid, sulfate, phosphate, chloride, bromide, iodide, acetate, propionate, hydrobromic acid, sodium hydroxide, potassium hydroxide, ammonium hydroxide, and potassium carbonate. These salts can be prepared by methods known in the art. For example, sodium salts may be prepared by dissolving the delivery agent in ethanol and adding aqueous sodium hydroxide. The delivery agent may be purified by recrystallization or by fractionation on one or more solid chromatographic supports, alone or linked in tandem. Suitable recrystallization solvent systems include, but are not limited to, acetonitrile, methanol, and tetrahydrofuran. Fractionation may be performed (i) on a suitable chromatographic support such as alumina, using methanol/n-propanol mixtures as the mobile phase, (ii) by reverse phase chromatography using trifluoroacetic acid/acetonitrile mixtures as the mobile phase, or (iii) by ion exchange chromatography using water or an appropriate buffer as the mobile phase. When anion exchange chromatography is performed, preferably a 0-500 mM sodium chloride gradient is employed.

The delivery agent may contain a polymer conjugated to it by a linkage group selected from the group consisting of —NHC(O)NH—, —C(O)NH—, —NHC(O), —OOC—, —COO—, —NHC(O)O—, —OC(O)NH—, —CH$_2$NH—NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond, with the proviso that the polymeric delivery agent is not a polypeptide or polyamino acid. The polymer may be any polymer including, but not limited to, alternating copolymers, block copolymers and random copolymers, which are safe for use in mammals. Preferred polymers include, but are not limited to, polyethylene; polyacrylates; polymethacrylates; poly(oxyethylene); poly(propylene); polypropylene glycol; polyethylene glycol (PEG); and derivatives thereof and combinations thereof. The molecular weight of the polymer typically ranges from about 100 to about 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons. U.S. Pat. No. 6,627,228 is hereby incorporated by reference in its entirety.

The amount of delivery agent in the solid pharmaceutical composition is a delivery agent effective amount and can be determined for the particular composition by methods known to those skilled in the art. Generally, the weight ratio of delivery agent to active agent ranges from about 0.1:1 to about 1000:1 and preferably from about 1:1 to about 300:1. The weight ratio will vary according to the active agent and the particular indication for which the active agent is administered.

Other suitable delivery agents for the present invention are described in U.S. Pat. Nos. 6,846,844, 6,699,467, 6,693,208, 6,693,208, 6,693,073, 6,663,898, 6,663,887, 6,646,162, 6,642,411, 6,627,228, 6,623,731, 6,610,329, 6,558,706, 6,525,020, 6,461,643, 6,461,545, 6,440,929, 6,428,780, 6,413,550, 6,399,798, 6,395,774, 6,391,303, 6,384,278, 6,375,983, 6,358,504, 6,346,242, 6,344,213, 6,331,318, 6,313,088, 6,245,359, 6,242,495, 6,221,367, 6,180,140, 5,541,155, 5,693,338, 5,976,569, 5,643,957, 5,955,503, 6,100,298, 5,650,386, 5,866,536, 5,965,121, 5,989,539, 6,001,347, 6,071,510, and 5,820,881. Delivery agents of the present invention are also described in U.S. Patent Application Publication Nos. 20050009748, 20040110839, 20040106825, 20040068013, 20040062773, 20040022856, 20030235612, 20030232085, 20030225300, 20030198658, 20030133953, 20030078302, 20030072740, 20030045579, 20030012817, 20030008900, 20020155993, 20020127202, 20020120009, 20020119910, 20020102286, 20020065255, 20020052422, 20020040061, 20020028250, 20020013497, 20020001591, 20010039258, and 20010003001. Delivery agents of the present invention are also described in International Publication Nos. WO 2005/020925, WO 2004/104018, WO 2004/080401, WO 2004/062587, WO 2003/057650, WO 2003/057170, WO 2003/045331, WO 2003/045306, WO 2003/026582, WO 2002/100338, WO 2002/070438, WO 2002/069937, WO 02/20466, WO 02/19969, WO 02/16309, WO 02/15959, WO 02/02509, WO 01/92206, WO 01/70219, WO 01/51454, WO 01/44199, WO 01/34114, WO 01/32596, WO 01/32130, WO 00/07979, WO 00/59863, WO 00/50386, WO 00/47188, WO 00/40203, and WO 96/30036. Each of the above listed U.S. patents and U.S. and International published applications are herein incorporated by reference. These delivery agents may be prepared by methods known in the art, such as those described in the aforementioned patents and published patent applications. For example, SNAC may be prepared by methods known in the art, such as those described in U.S. Pat. Nos. 5,650,386 and 5,866,536, and U.S. Patent Application Publication No. 2002/0065255.

Active Agents

Active agents suitable for use in the present invention include biologically active agents and chemically active agents, including, but not limited to, pesticides, pharmacological agents, and therapeutic agents. Suitable active agents include those that are rendered less effective, ineffective or are destroyed in the gastro-intestinal tract including by acid hydrolysis, enzymes and the like. Also included as suitable active agents are those macromolecular agents whose physiochemical characteristics, including, size, structure or charge, prohibit or impede absorption when dosed orally.

For example, an agent that is to enter the body, or that can benefit from improved pharmacokinetics including delivery, for example when oral bioavailability is limited or nonexistent. These agents are biologically or chemically active agents suitable for use in the present invention include, but are not limited to, macromolecules, such as peptides, including proteins and polypeptides, including dipeptides; hormones; and saccharides, including monosaccharides, polysaccharides, including disaccharides, mixtures of muco-polysaccharides; carbohydrates; lipids; and small polar organic molecules (i.e. polar organic molecules having a molecular weight of 500 daltons or less); nucleosides, other organic compounds; and particularly compounds without oral bioavailability or with limited oral bioavailability, including those compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof:

Amylin and Amylin Agonists;
Adrenocorticotropin;
Antigens;
Antimicrobials, including Antibiotics, Anti-Bacterials and Anti-Fungal Agents; non-limiting examples of Antibiotics include Gram-Positive Acting, Bacteriocidal, Lipopeptidal and Cyclic Peptidal Antibiotics, such as Daptomycin And Analogs thereof;
Anti-Migraine Agents such as BIBM-4096BS And Other Calcitonin Gene-Related Proteins Antagonists, Sumatriptan Succinate;
Antivirals including Acyclovir, Valacyclovir;
Atrial Naturetic Factor;
Bisphosphonates, including Alendronate, Clodronate, Etidronate, Ibandronate, Incadronate, Minodronate, Neridronate, Olpadronate, Pamidronate, Risedronate, Tiludronate, Zoledronate, EB1053, and YH529;
Calcitonin, including Salmon, Eel, Porcine And Human;
Cholecystokinin (CCK) And CCK Agonists Including CCK-8;
Cromolyn Sodium (Sodium Or Disodium Chromoglycate);
Cyclosporine;
Desferrioxamine (DFO);
Erythropoietin;
Exedin and Exedin Agonists, including Exendin-3, Exendin-4;
Filgrastim
Follicle Stimulating Hormone (recombinant and natural);
Glucagon-Like Peptide 1 (GLP-1), Glucagon, and Glucagon-Like Peptide 2 (GLP-2);
Glucocerebrosidase;
Gonadotropin Releasing Hormone;
Growth Hormone Releasing Factor;
Growth Hormone Releasing Hormones;
Growth Hormones, Including Human Growth Hormones (hGH), Recombinant Human Growth Hormones (rhGH), Bovine Growth Hormones, And Porcine Growth Hormones;
Heparin, Including Unfractionated Heparin, Heparinoids, Dermatans, Chondroitins, Low Molecular Weight Heparin, Very Low Molecular Weight Heparin Ultra Low Molecular Weight Heparin and synthetic heparins including Fondiparinux;
Insulin, Including Porcine, Bovine, Human, And Human Recombinant, Optionally Having Counter Ions Including Zinc, Sodium, Calcium And Ammonium;
Insulin-Like Growth Factor, Including IGF-1;
Interferons, Including α (E.G., Interferon Alfacon-1 (Available As Infergen ® From Intermune, Inc. Of Brisbane, Ca)), β, OMEGA and γ;
Interleukin-1; Interleukin-2; Interleukin-11; Interleukin-21;
Leutinizing Hormone and Leutinizing Hormone Releasing Hormone;
Leptin (OB Protein);
Monoclonal Antibodies including Retuxin, TNF-alpha soluble receptors;
Oxytocin;
Parathyroid Hormone (PTH), Including Its Fragments, including PTH 1-34 and PTH 1-38;
Peptide YY (PYY) Including PYY Agonists, Fragment 3-36;
Prostaglandins;
Protease Inhibitors;
Somatostatin;
Thrombopoietin;
Vancomycin;
Vasopressin;
Vitamins;
Vaccines Including Those Against Anthrax Or *Y. Pestis*, Influenza, and Herpes;

Including secretagogues, analogs, fragments, mimetics or polyethylene glycol (PEG)-modified derivatives of these compounds; or any combination thereof.

Delivery Systems

The composition of the present invention comprises one or more delivery agent compounds of the present invention, and one or more active agents. In one embodiment, one or more of the delivery agent compounds, or salts of these compounds, or poly amino acids or peptides of which these compounds or salts form one or more of the units thereof, may be used as a delivery agent by mixing with the active agent prior to administration to form an administration composition.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycol. Dosing solutions may be prepared by mixing a solution of the delivery agent compound with a solution of the active agent, just prior to administration. Alternately, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the active agent. Alternately, a solid may be obtained from a solution of compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects.

The presently disclosed delivery agent compounds facilitate the delivery of biologically and chemically active agents, particularly in oral, intranasal, sublingual, gastric, intestinal, including intraduodenal, jejunal and ileul delivery, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful for orally administering active agents, especially those that are not ordinarily orally deliverable, or those for which improved delivery is desired.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering the active agent in a particular time period (such as to effect quicker or delayed delivery), or in delivering the active agent at a specific time, or over a period of time (such as sustained delivery).

Another embodiment of the present invention is a method for the treatment or prevention of a disease or for achieving a desired physiological effect, such as those listed in the table below, in an animal by administering the composition of the present invention. Preferably, an effective amount of the composition for the treatment or prevention of the desired disease or for achieving the desired physiological effect is administered. Specific indications for active agents can be found in (1) the Physicians' Desk Reference (58th Ed., 2004, Medical Economics Company, Inc., Montvale, N.J.), and (2) Fauci, A S, et. al., Harrison's Principles of Internal Medicine (14th Ed., 1998, McGraw-Hill Health Professions Division, New York), both of which are herein incorporated by reference. The active agents in the table below include their analogs, fragments, mimetics, and polyethylene glycol-modified derivatives.

| Active Agent | Disease and Physiological Effect |
|---|---|
| Amylin and Amylin Agonists; Adrenocorticotropin; | Obesity High Cholesterol (To Lower Cholesterol) |
| Antigens; | Infection |
| Antivirals including Acyclovir, Valacyclovir; | Viral Infections, including Herpes simplex type I and type II |
| Growth hormones (including human recombinant growth hormone and growth-hormone releasing factors and its analogs) | Growth disorders |

-continued

| Active Agent | Disease and Physiological Effect |
| --- | --- |
| Interferons, including α, β and γ | Viral infection, including chronic cancer, hepatitis, and multiple sclerosis |
| Interleukins (e.g. Interleukin-1; interleukin-2, interleukin-11, and interleukin-21) | Viral infection; cancer; cell mediated immunity; and transplant rejection; |
| Insulin; Insulin-like growth factor IGF-1 | Diabetes |
| Heparin | Treatment and Prevention of Thrombosis, including (Deep Vein Thrombosis); prevention of blood coagulation |
| Calcitonin including Salmon, Eel, Porcine And Human Calcitonin; | Osteoporosis; diseases of the bone; bone pain; analgesic (including pain associated with osteoporosis or cancer) |
| Cholecystokinin (CCK) And CCK Agonists Including CCK-8; | Obesity |
| Erythropoietin | Anemia; HIV/HIV-therapy Associated Anemia; Chemotherapeutically-Induced Anemia |
| Atrial naturetic factor | Vasodilation |
| Antigens | Infection |
| CPHPC | Reduction of amyloid deposits and systemic amyloidoisis often (but not always) in connection with Alzheimer's disease, Type II diabetes, and other amyloid-based diseases |
| Monoclonal antibodies (Antibodies including Retuxin, TNF-alpha soluble receptors;) | To prevent graft rejection; cancer; used in assays to detect diseases |
| Leptin (OB Protein) | Obesity |
| Somatostatin/octreotide | Bleeding ulcer; erosive gastritis; variceal bleeding; diarrhea; acromegaly; TSH-secreting pituitary adenomas; secretory pancreatic tumors; carcinoid syndrome; reduce proptosis/thyroid-associated ophthalmopathy; reduce macular edema/retinopathy |
| Protease inhibitors | HIV Infection/AIDS |
| Adrenocorticotropin | High cholesterol (to lower cholesterol) |
| Gonadotropin releasing hormone | Ovulatory disfunction (to stimulate ovulation) |
| Oxytocin | Labor disfunction (to stimulate contractions) |
| Leutinizing-hormone-releasing-hormone; follicle stimulating hormone | Regulate reproductive function |
| Glucocerebrosidase | Gaucher disease (to metabolize lipoprotein) |
| Thrombopoietin | Thrombocytopenia |
| Filgrastim (Granulocyte Colony Stimulating Factor); GM-CSF, (sargramostim) | shorten the duration of chemotherapy-induced neutropenia and thus treat or prevent infection in chemotherapy patients; Inhibit the growth of or to kill *Mycobacterium* Intracellular *Avium* Infection (MAC) |
| Prostaglandins | Hypertension |
| Cyclosporin | Transplant rejection |
| Vasopressin | Nocturnal Enuresis; antidiuretic |
| Cromolyn sodium; | Asthma; allergies |
| Vancomycin | Treat or prevent antimicrobial-induced infections including, but not limitted to methacillin-resistant *Staphalococcus aureus* and *Staph. epidermiditis* |
| gallium nitrate | Osteoporosis; Paget's disease; Inhibits osteoclasts; Promotes osteoblastic activity, hypercalcemia, including cancer related hypercalcemia, urethral (urinary tract) malignancies; anti-tumors, cancers, including urethral and bladder cancers; lymphoma; malignancies (including bladder cancer); leukemia; management of bone metastases (and associated pain); muliple myeloma, attenuate immune response, including allogenic transplant rejections; disrupt iron metabolism; promote cell migration; wound repair; to attenuate or treat infectious processes of *mycobacterium* species, including but not limited to *mycobacterium tubercolosis*, and *mycobacterium avium* complex |
| Desferrioxamine (DFO) | Iron overload |
| Parathyroid hormone (PTH), including its fragments. | Osteoporosis; Diseases of the bone |
| Antimicrobials | Infection including but not limited to gram-positive bacterial infection |
| Vitamins | Treat and prevent Vitamin deficiencies |
| Bisphosphonates including Alendronate, Clodronate, Etidronate, Ibandronate, Incadronate, Minodronate, Neridronate, Olpadronate, Pamidronate, Risedronate, Tiludronate, Zoledronate, EB1053, and YH529; | Osteoporosis; Paget's disease; bone tumors and metastases (and associated pain); Breast cancer; including as adjuvant therapy for early stage breast cancer; management of bone metastases (and associated pain), including bone metastases associate with breast cancer, prostate cancer, and lung cancer; Inhibits osteoclasts; Promotes osteoblastic activity; treat and/or prevent bone mineral density (bmd) loss; multiple myeloma; prevention of bone complications related to malignant osteolysis; fibrous dysplasia; pediatric osteogenesis imperfecta; hypercalcemia, urethral (urinary tract) malignancies; reflex sympathetic dystropy synodrome, acute back pain after vertebral crush fracture, chronic inflammatory joint disease, renal bone disease, extrosseous calcifications, analgesic, vitamin D intoxication, periarticular ossifications |
| Anti-Migraine Agents such as BIBM-4096BS BIBN4096BS - (1-Piperidinecarboxamide. N-[2-[[5-amino-1-[[4-(4-pyridinyl)-1-piper-azinyl)carbonyl]pentyl]amino]-1-[(3,5-dibromo-4-hydroxy-phenyl)methyl]-2-oxoethyl]-4(1,4-dihydro-2-oxo-3(2H0-quinazolinyl)-.[R—(R*,S*)]—) And Other Calcitonin Gene-Related Proteins Antagonists, Sumatriptan Succinate; | Anti-migraine; calcitonin gene-related peptide antagonist |
| Glucagon | improving glycemic control (e.g. treating hypoglycemia and controlling hypoglycemic reactions), obesity; a diagnostic aid in the radigocial examination of the stomach, duodenum, small bowel and colon; Treat acute poisoning With Cardiovascular Agents including, but not limited to, calcium channel blockers, beta blockers |
| GLP-1, Exendin-3, Exendin-4 | Diabetes; improving glycemic control (e.g. treating hypoglycemia and controlling hypoglycemic reactions), obesity |
| dipeptidyl peptidase IV (DPP-4) inhibitors | Diabetes; improving glycemic control (e.g. treating hypoglycemia), obesity |
| Vaccines Including Those Against Anthrax Or *Y. Pestis*, Influenza, and Herpes; | Prevent or Minimize Disease or Infection |
| Peptide YY (PYY) and PYY-like Peptides | Obesity, Diabetes, Eating Disorders, Insulin-Resistance Syndromes |

For example, one embodiment of the present invention is a method for treating a patient having or susceptible to diabetes by administering insulin in a pharmaceutical formulation of the present invention. Other active agents, including those set forth in the above table, can be used in conjunction with the pharmaceutical formulations of the present invention.

Following administration, the active agent present in the composition or dosage unit form is taken up into the circulation. The bioavailability of the agent can be readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

Additives

The solid pharmaceutical composition and unit dosage form of the present invention may include other active agents and pharmaceutically acceptable additives, such as excipients, carriers, diluents, stabilizers, plasticizers, binders, glidants, disintegrants, bulking agents, lubricants, plasticizers, colorants, film formers, flavoring agents, taste-masking agents, sugars, sweeteners, preservatives, dosing vehicles, surfactants, and any combination of any of the foregoing. Preferably, these additives are pharmaceutically acceptable additives, such as those described in *Remington's, The Science and Practice of Pharmacy*, (Gennaro, A. R., ed., 20$^{th}$ edition, 2003, Mack Pub. Co.), which is herein incorporated by reference.

Suitable binders include, but are not limited to, starch, gelatin, sugars (such as sucrose, molasses and lactose), dibasic calcium phosphate dihydrate, natural and synthetic gums (such as acacia, sodium alginate, carboxymethyl cellulose, methyl cellulose, polyvinylpyrrolidone, polyethylene glycol, ethylcellulose, and waxes.

Suitable glidants include, but are not limited to, talc and silicon dioxide (silica) (e.g., fumed silica and colloidal silicon dioxide).

Suitable disintegrants include, but are not limited to, starches, sodium starch glycolate, croscarmellose sodium, crospovidone, clays, celluloses (such as purified cellulose, methylcellulose, and sodium carboxymethyl cellulose), alginates, pregelatinized corn starches, and gums (such as agar, guar, locust bean, karaya, pectin and tragacanth gums). A preferred disintegrant is sodium starch glycolate.

Suitable bulking agents include, but are not limited to, starches (such as rice starch), microcrystalline cellulose, lactose (e.g., lactose monohydrate), sucrose, dextrose, mannitol, calcium sulfate, dicalcium sulfate, and tricalcium sulfate.

Suitable lubricants include, but are not limited to, stearic acid, stearates (such as calcium stearate and magnesium stearate), talc, boric acid, sodium benzoate, sodium acetate, sodium fumarate, sodium chloride, polyethylene glycol, hydrogenated cottonseed, and castor oils.

Suitable surfactants include, but are not limited to, sodium lauryl sulfate, hydroxylated soy lecithin, polysorbates, and block copolymers of propylene oxide and ethylene oxide.

Dosage Forms

The solid pharmaceutical composition of the present invention, which includes an active agent and a delivery agent, can be formulated as a solid unit dosage form. The dosage form can be, for example, a tablet, a sachet, or a capsule, such as a hard or soft gelatin capsule. The dosage form can provide immediate, sustained, or controlled release of the delivery agent, heparin, and optionally, additional active agents.

The solid pharmaceutical composition and solid unit dosage form of the present invention can be prepared as follows. A delivery agent in solid form is processed (such as by milling through a 35-mesh screen) to provide a powder having a relatively small and preferably uniform particle size. The delivery agent is then blended with a delivery agent, and optionally a filler and/or wetting agent with, for example, a V-blender or similar device, to provide a powder blend.

Separately, a wetting agent mixture is prepared by mixing a wetting agent, heparin and a delivery agent. The mixture may also, for example, include water. The formulation of the wetting mixture is selected so as to wet the heparin when mixed with the aforementioned powder blend. According to one preferred embodiment, the wetting agent mixture is also formulated so as to partially solubilize the delivery agent when mixed with the powder blend.

The powder blend is added to the wetting agent mixture in small increments under continuous mixing. Mixing is continued for a sufficient time (e.g., 15 minutes) after all of the powder blend has been added to obtain a uniform composition. The resulting composition is typically a semi-solid, gel, or liquid.

The composition may then be formulated into a dosage form, such as a capsule, by methods known in the art. According to one preferred embodiment, the resulting composition is packed into a soft gelatin capsule or hard gelatin capsule (e.g., Size 0 Licap Capsugel Hard Gelatin capsules). Other suitable methods are described in U.S. Pat. Nos. 6,605,298, 6,458, 383, 6,261,601, 5,714,477, and 3,510,561; U.S. Patent Application Publication Nos. 2003/0077303 and 2001/0024658; and International Publication No. WO 88/10117, all of which are incorporated by reference.

EXAMPLES

The following examples illustrate the present invention without limitation. All percentages are by weight unless otherwise specified.

Proton nuclear magnetic resonance (1H NMR) analyses for the compounds listed below were conducted on a 300 MHz Bruker® spectrometer (Bruker-Physik AG, Silberstreifen, GERMANY) or a 400 MHz JEOL spectrometer (JEOL USA, Inc., Peabody, Mass.) using dimethyl sulfoxide (DMSO-d6) as the solvent unless otherwise indicated.

Liquid chromatograph/mass spectrometry (LC-MS) analyses were performed with an Agilent Technologies (Palo Alto, Calif.), LC/MSD 1100 (single quad) having the following parameters:

Mobile Phase A: 50:950:5 acetonitrile:water:acetic acid (v/v/v).

Mobile Phase B: 950:50:5 acetonitrile:water:acetic acid (v/v/v).

Gradient Elution: 4 minute linear gradient 0-100% B; total time per injection is 11 minutes.

Injection volume: 5 μL.

Column: ZORBAX Rapid Resolution Cartridge, SB-C18, 2.1×30 mm, 3.5 um.

Particle size, catalog #873700-902.

Column temp: 40° C.

UV detection at 244 nm.

MSD parameters:

Source: API-ES, positive polarity

| Scan parameters: | |
| --- | --- |
| Mass Range: | 125.00-600.00 |
| Fragmentor: | 60 V |
| Gain: | 1.0 EMV |
| Threshold: | 150 |

-continued

| Spray Chamber: | |
|---|---|
| Gas Temp. | 350 deg. D |
| Drying Gas: | 12.0 l/min |
| Neb. Pressure; | 40 psig |
| VCap | 4000 V positive/negative. |

Example 1

Preparation of Compounds 1-22

Compounds 1-22 were made according to the method of U.S. Pat. No. 6,384,278, which is hereby incorporated by reference in its entirety.

An appropriate N-substituted aniline was mixed with an appropriate dicarboxylic acid mono ester and heated in the presence of a boric acid catalyst in xylene. The intermediate carbamide was hydrolyzed to obtain the final product.

Example 2

Preparation of Compounds 23-34 and 59

A dried, 200 mL, 3-necked, round-bottomed flask was equipped with a Teflon-coated magnetic bar and a vacuum jacketed Dean-Stark trap which was topped with a reflux condenser fitted with a Nitrogen inlet. The reaction vessel was charged with N-isopropyl-N-phenylamine (8.11 g, 60 mmol), boric acid (0.93 g, 15 mmol,), and xylene (88 mL). To the stirred reaction mixture was added 7-ethoxy-7-oxoheptanoic acid (11.29 g, 60 mmol) in one portion. The reaction was heated to reflux using a heating mantle. The azeotroped water began to separate and was collected in the Dean-Stark trap. After 16 hours of reflux, water was collected, and the reaction was allowed to cool to ambient temperature reaction. The reaction mixture was diluted with ethyl acetate (100 mL), and was washed with an aqueous 2N solution of HCl (50 mL), and followed with a saturated solution of sodium bicarbonate (60 mL). The majority of the organic solvent was removed in vacuum. To residue was added a 2 N aqueous solution of sodium hydroxide (60 mL). The mixture was heated at 60° C. for 4 hours. Upon cooling to room temperature, the mixture was washed 60 mL of ethyl acetate. After being carefully separated from the organic layer, the aqueous phase was subjected to evaporation to remove any residual ethyl acetate. Ice was added to the aqueous solution, followed by an aqueous solution of HCl (2N, 60 mL) leading to the precipitation of a white solid. Stirring was continued for an additional 30 minutes before the precipitate was collected with a sintered funnel. The collected white solid was successfully washed with water and hexane before it was in vacuo at room temperature for 12 h to afford 7.49 g (45%) of 7-[isopropyl(phenyl)amino]-7-oxoheptanoic acid as a white solid. HPLC: single peak at 4.83 min.; Mp: 62-63° C. $^1$H NMR (DMSO-d6,) δ: 0.95-0.97 (d, 6H), 1.08-1.10 (m, 2H), 1.34-1.40 (m, 4H), 1.76-1.79 (m, 2H), 2.09-2.13 (m, 2H), 4.81-4.85 (m, 1H), 7.18-7.20 (m, 2H), 7.44-7.46 (m, 3H). Mass (M+1): 278. Anal. Calc'd for $C_{16}H_{23}NO_3$: C, 69.29; H, 8.36; N5.05. Found: C, 69.06; H, 8.45; N, 4.99.

Compounds 24-34 and 59 were prepared from the appropriate starting materials using the same procedure.

Compound (24)

HPLC: single peak at 4.43 min. Mass (M+1): 264. $^1$H NMR (400 MHz, DMSO-$d_6$) δ: 0.95 (d, 6H), 1.30 (m, 2H), 1.40 (m, 2H), 1.80 (m, 2H), 2.00 (m, 2H), 4.80 (m, 1H), 7.15 (m, 2H), 7.40 (m, 3H). $^{13}$C NMR (100 MHz, DMSO-$d_6$) δ: 21.0, 24.0, 24.5, 33.0, 34.0, 45.0, 128.0, 129.0, 130.0, 138.5, 170.5, 174.0.

Compound (25)

HPLC: single peak at 4.62 min. Mass (M+1): 264. $^1$H NMR (400 MHz, DMSO-$d_6$) δ: 0.78 (d, 3H), 0.94-0.95 (d, 6H), 1.70-1.72 (m, 1H), 1.80-1.92 (m, 2H), 2.08-2.15 (m, 1H), 2.20-2.30 (m, 1H), 4.75-4.90 (m, 1H), 7.10-7.20 (m, 2H), 7.35-7.50 (m, 3H). $^{13}$C NMR (100 MHz, DMSO-$d_6$) δ: 19.5, 21.0, 27.0, 40.5, 41.0, 45.0, 128.0, 129.0, 130.5, 138.5, 170.0, 174.0.

Compound (26)

HPLC: single peak at 4.19 min. Mass (M+1): 250. $^1$H NMR (400 MHz, DMSO-$d_6$) δ: 0.65 (d, 3H), 0.84-0.86 (t, 3H), 1.80-1.90 (m, 3H), 2.01-2.12 (m, 2H), 3.49-3.53 (q, 2H), 7.09-7.11 (d, 2H), 7.20-7.25 (m, 1H), 7.30-7.32 (m, 2H). $^{13}$C NMR (100 MHz, DMSO-$d_6$) δ: 9.18, 15.87, 17.30, 23.35, 39.50, 123.98, 124.72, 125.92, 138.39, 166.17, 168.27, 169.80.

Compound (27)

HPLC: single peak at 3.92 min. Mass (M+1): 250. $^1$H NMR (400 MHz, DMSO-$d_6$) δ: 1.13 (m, 2H), 1.37-1.46 (m, 4H), 1.99 (m, 2H), 2.10-2.15 (t, 2H), 3.15 (s, 3H), 7.29-7.37 (m, 3H), 7.42-7.47 (m, 2H).

Compound (28)

HPLC: single peak at 3.72 min. Mass (M+1): 236. $^1$H NMR (400 MHz, DMSO-$d_6$) δ: 0.79-0.81 (d, 3H), 1.93-2.02 (m, 3H), 2.16-2.30 (m, 2H), 3.15 (s, 3H), 7.27-7.37 (m, 3H), 7.43-7.48 (m, 2H).

Compound (29)

HPLC: single peak at 3.88 min. Mass (M+1): 242. $^1$H NMR (400 MHz, DMSO-$d_6$) δ: 2.21 (m, 2H), 2.49 (m, 2H), 3.13 (s, 3H), 7.37 (m, 2H), 7.58 (m, 2H), 12.10 (br., 1H). $^{13}$C NMR (100 MHz, DMSO-$d_6$) δ: 28.81, 29.0, 36.5, 129.32, 129.58, 132.0, 142.66, 170.58, 173.63.

Compound (30)

HPLC: single peak at 4.82 min. Mass (M+1): 278. $^1$H NMR (400 MHz, DMSO-$d_6$) δ: 1.02 (m, 4H), 1.32 (m, 4H), 1.86 (m, 2H), 2.05 (m, 2H), 2.21 (s, 3H), 3.00 (s. 3H), 7.00 (m, 2H), 7.12 (m, 2H), 11.85 (br., 1H).

Compound (31)

HPLC: single peak at 4.44 min. Mass (M+1): 294. $^1$H NMR (400 MHz, DMSO-$d_6$) δ: 1.10 (m, 4H), 1.39 (m, 4H), 1.93 (m, 2H), 2.11 (m, 2H), 3.07 (s. 3H), 3.75 (s 3H), 6.96 (m, 2H), 7.20 (m, 2H), 11.93 (br., 1H).

Compound (32)

HPLC: single peak at 4.81 min. Mass (M+1): 278. $^1$H NMR (400 MHz, DMSO-$d_6$) δ: 0.97 (t, 3H), 1.10 (m, 4H), 1.39 (m, 4H), 1.90 (m, 2H), 2.13 (m, 2H), 3.58-3.63 (q, 2H), 7.09-7.24 (d, 2H), 7.34 (m, 1H), 7.41-7.45 (m, 2H).

Compound (33)

HPLC: single peak at 5.48 min. Mass (M+1): 312. $^1$H NMR (400 MHz, DMSO-$d_6$) δ: 0.96 (t, 3H), 1.10 (m, 4H), 1.40 (m, 4H), 1.91 (m, 2H), 2.12 (m, 2H), 3.60 (q, 2H), 7.27 (d, 2H), 7.46 (m, 2H), 11.93 (br., 1H).

Compound (34)

HPLC: single peak at 4.52 min. Mass (M+1): 282. $^1$H NMR (400 MHz, DMSO-$d_6$) δ: 1.09 (m, 4H), 1.39 (m, 4H), 1.93 (m, 2H), 2.10-2.14 (m, 2H), 3.09 (s. 3H), 3.75 (s 3H), 7.19 (m, 2H), 7.30 (m, 2H), 11.91 (br., 1H).

Compound (59)

HPLC: single peak at 4.71 min. Mass (M+1): 284. $^1$H NMR (400 MHz, DMSO-$d_6$) δ: 0.90 (t, 3H), 1.35-1.37 (m, 4H), 1.87 (t, 2H), 2.04 (t, 2H), 3.52-3.57 (q, 2H), 7.25 (m, 2H), 7.43 (m, 2H), 11.94 (s, 1H).

Example 3

Preparation of Compounds 111-139

Compound 111

4-Oxo-4-phenyl-butyric acid 10 g (56 mmol) of 3-benzoylpropionic acid (available from Sigma-Aldrich Co., St. Louis, Mo.) was added to 10 mL water. The mixture was stirred and 28 mL of 2N sodium hydroxide (aqueous) was added. The resulting solution was stirred for 2 hours and the solid product was collected after the solution was by lyophilized. 1H NMR (d6-DMSO): δ 7.9, d, 2H, (aryl H's); δ 7.6, t, 1H, (aryl H's); δ 7.5, t, 2H, (aryl H's); δ 3.1, t, 2H (CH$_2$ α to carbonyl); δ 2.2, t, 2H (CH$_2$ α to COOH); COOH peak not observed due to water present in sample.

Compound 113

10-(4-Hydroxy-phenyl)-10-oxo-decanoic acid

A 500 mL flask, equipped with a reflux condenser and under inert atmosphere, was charged with decanedioic acid (20 g, 296 mmol) and acetic anhydride (280 mL, 2.96 mol). The mixture was heated to reflux for 5 hours. Acetic acid and excess acetic anhydride was removed under reduced pressure. The product was used without further purification.

To a 500 mL flask, equipped with mechanical stirrer and under inert atmosphere, was added Oxacycloundecane-2,11-dione (20 g, 108.5 mmol), phenol (10.22 g, 108.5 mmol), and 200 mL carbon disulfide. Aluminum (III) trichloride (72.34 g, 542 mmol) was added and the reaction was stirred for 72 hours. Carbon disulfide was decanted away, and ice was carefully added until most of mixture was dissolved. The insoluble material was collect by suction filtration and washed with 2×100 mL of water. The solid was then dissolved in 100 mL of 1 M aqueous sodium hydroxide and then carefully acidified with 1 M aqueous hydrochloric acid until pH=7.5 The solids that formed were removed by filtration and the parent solution was continued to be acidified until pH 2.5. The crude product precipitate was collected by filtration and was washed with 1×100 mL water. The crude product was dissolved in 100 mL of 1 M aqueous sodium hydroxide and then carefully acidified with 1 M aqueous hydrochloric acid until pH=7.5 and the impurities that precipitated were filtered off. The parent solution was further acidified until pH 2. The crude product was collected by filtration and washed with 2×50 mL water. The product was recrystallized form acetone. The isolated product (1.2 g, 4%) was collected by filtration. Found: C, 69.00; H, 7.81%; C$_{16}$H$_{22}$O$_4$ requires C, 69.04; H, 7.97%; 1H NMR (d6-DMSO): δ 12.0, bs, 1H (COOH); δ 10.3, bs, 1H (aryl-hydroxyl); δ 7.8 d, 2H (aryl H's); δ 6.8, d, 2H, (aryl H's); δ 2.9, t, 2H (CH$_2$ α to carbonyl); δ 2.2, t, 2H (CH$_2$ α to COOH); δ 1.5, multiplet, 4H (CH$_2$'s β to carbonyl & β to COOH), δ 1.3, multiplet, 8H (rest of CH$_2$'s).

Compound 114

10-(2-Hydroxy-phenyl)-10-oxo-decanoic acid

To a 100 mL flask was added methylene chloride (50 mL), 9-bromononanol (7.63 g, 34.2 mmol) and trimethylsilyl chloride (4.5 mL, 35.5 mmol) and allowed to stir under nitrogen for 20 minutes. Triethyl amine (5.0 mL, 35.9 mmol) was then added and the resulting reaction mixture was stirred for 2 hours at room temperature. The reaction mixture was then diluted with 80 mL of hexane, filtered, and then concentrated under reduced pressure. The resulting residue was again diluted with 80 mL of hexane, filtered, and then concentrated under reduced pressure to yield 9.7 g (96%) of a yellow liquid which was used without further purification.

5.69 g (19.3 mmol) of (9-Bromo-nonyloxy)-trimethyl-silane was added drop-wise to a 50 mL flask under an inert atmosphere containing magnesium metal (0.59 g, 24.3 mmol), 20 mL tetrahydrofuran and a small crystal of iodine was used to initiate the Grignard reaction. In a 100 mL flask under inert atmosphere a solution of salicylylaldehyde (2.1 mL, 19.7 mmol) in 20 mL of tetrahydrofuran was cooled with an external ice bath. The cooled aldehyde solution was then treated with 1.0 M lithium bis(trimethylsilyl)amide (20.0 mL, 20 mmol). The Grignard reaction was cooled with an external ice bath after stirring for 1 hour. The cooled Grignard was then added drop-wise via cannula to the aldehyde solution over a 5 minute period with constant stirring. The resulting reaction mixture was allowed to warm to room temperature and continue to stir overnight. The reaction was poured into 40 mL of ethyl acetate and quenched with 15 mL of saturated aqueous sodium bicarbonate solution. The organic layer was separated and washed with 2×25 mL portions of 4% aqueous hydrochloric acid followed by 1×20 mL portion of brine. The organic layer was dried over sodium sulfate, filtered, and the solvent removed under reduced pressure. Residual salicylaldehyde was removed by Kugelrohr distillation and the resulting residue was used without further purification.

A 100 mL flask was charged with 1-(2-Hydroxy-phenyl)-undecane-1,11-diol (5.0 g, 18.9 mmol) and 50 mL of dimethyl formamide. To this was added pyridinium dichromate (32.9 g, 87.5 mmol). (The addition was mildly exothermic.) The reaction mixture was stirred at room temperature overnight. The reaction mixture was poured into 50 mL of ethyl acetate and washed with 200 mL of water, 30 mL of 4% aqueous hydrochloric acid, 30 mL water, and finally with 30 mL of brine. The organic layer was then stirred with 10 g of silica gel for 15 minutes, dried with sodium sulfate, filtered, and solvent removed under reduced pressure. The off-white crude product was recrystallized from ethanol/water. The product (0.5 g, 10%) was isolated as an off-white solid, mp 85-87° C. Combustion analysis: Found: C, 69.01, H, 8.36%; C$_{16}$H$_{22}$O$_4$ requires C, 69.54; H, 8.02%; 1H NMR (d6-DMSO): δ 12.0, s, 1H (COOH); δ 7.9 dd, 1H (aryl H); δ 7.5, dt, 1H, (aryl H); δ 6.9, complex multiplet, 2H (aryl H's), 3.1, t, 2H (CH$_2$ α to carbonyl); δ 2.2, t, 2H(CH$_2$ α to COOH); δ 1.6, multiplet, 2H (CH$_2$ β to carbonyl), δ 1.5, multiplet, 2H (CH$_2$ β to COOH), δ 1.3, multiplet, 8H (rest of CH$_2$'s).

Compound 115

4-(4-Methoxy-phenyl)-4-oxo-butyric acid

A 500 mL round bottom flask equipped with a magnetic stirrer bar and an inert atmosphere (nitrogen gas) was charged with 5.25 mL (48.3 mmol) of anisole, 4.83 g (48.3 mmol) of succinic anhydride, 125 mL 1,1,2,2-tetrachloroethane and 125 mL of nitrobenzene. The reaction vessel was cooled with an external ice bath and stirred for 30 minutes. Aluminum trichloride (14.2 g, 106.4 mmol) was added to the pale yellow solution, which then turned to a dark reddish brown color. The ice bath was removed, and the reaction was allowed to stir at room temperature for 36 hours. Reaction was again cooled with an external ice bath. Prepared acidic solution by pouring 1N hydrogen chloride solution into a 100 mL beaker filled with ice. This solution was added to the reaction mixture carefully, drop-wise at first until reaction became clear with white precipitate. After that point a 10 mL portion was carefully added to test for reactivity, and then the remained of the ice/acid mixture was added. A second 100 mL of ice/acid mixture was added, the external ice bath removed and the pale emulsion was stirred for 2 hours. A white precipitate was collected form the emulsion by suction filtration. This solid was dissolved in 300 mL of 0.3 M sodium hydroxide, washed with 100 mL of ethyl acetate, and acidified to ~pH 1 with 1 M hydrochloric acid. The white precipitate that was collected upon vacuum filtration was washed with 3×100 mL de-ionized water and dried. The product (4.7 g, 47%) was isolated as a white solid, mp 149-150° C. Combustion analysis: Found: C, 63.52; H, 5.78%; $C_{11}H_{12}O_4$ requires C, 63.45; H, 5.81%; 1H NMR (d6-DMSO): δ 12.2, s, 1H (COOH); δ 7.9 d, 2H (aryl H's); δ 7.0, d, 2H, (aryl H's); δ 3.8, s, 3H (OMe H's); δ 3.2, t, 2H ($CH_2$ α to carbonyl); δ 2.5, t, 2H ($CH_2$ α to COOH).

Compound 116

5-(4-Methoxy-phenyl)-5-oxo-pentanoic acid

Compound 116 was prepared similarly to compound 15, except utilizing glutaric anhydride instead of succinic anhydride, mp 141-142° C. Found: C, 64.65; H, 6.34%; $C_{12}H_{14}O_4$ requires C, 64.85; H, 6.35%; 1H NMR (d6-DMSO): δ 12.2, s, 1H (COOH); δ 7.9 d, 2H (aryl H's); δ 7.0, d, 2H, (aryl H's); δ 3.8, s, 3H (OMe H's); δ 3.0, t, 2H ($CH_2$ α to carbonyl); δ 2.3, t, 2H ($CH_2$ α to COOH)); δ 1.8 quintuplet, 2H($CH_2$ between the other two).

Compound 117 was purchased from Aldrich (St. Louis, Mo.), catalog number 514683.

Compound 118 was purchased from Aldrich (St. Louis, Mo.), catalog number B12687.

Compound 119 was purchased from Aldrich (St. Louis, Mo.), catalog number S346810.

Compound 120 was purchased from Reike, Aldrich (St. Louis, Mo.), catalog number 7013D.

Compound 121 was purchased from Reike, Aldrich (St. Louis, Mo.), catalog number 7148C and Compound 121

5-(4-Isopropyl-phenyl)-5-oxo-pentanoic acid sodium salt 5-(4-Isopropyl-phenyl)-5-oxo-pentanoic acid (5 g, 21.3 mmol) was dissolved in 75 mL ethanol in a 250 mL flask. Sodium hydroxide (0.85 g, 21.3 mmol) was added and the reaction was stirred overnight under reduced pressure on a rotary evaporator. The solid was dried under vacuum and used without further purification. Found: C, 60.24; H, 6.66; Na, 9.21%; $C_{14}H_{17}O_3Na$ requires C, 61.28; H, 6.98; Na, 8.38%; 1H NMR (D2O): δ 7.7, d, 2H (aryl-H's); δ 7.2 d, 2H (aryl H's); δ 2.9, t, 2H ($CH_2$ α to carbonyl); δ 2.8, multiplet, 1H, (CH of isopropyl group); δ 2.1, t, 2H ($CH_2$ α to COOH); δ 1.8, q, 2H ($CH_2$ β to both carbonyl & COOH), δ 1.1, d, 6H($CH_3$'s of isopropyl group).

Compound 122 was purchased from Aldrich (St. Louis, Mo.), catalog number B13802.

Compound 123 was purchased from Reike, Aldrich (St. Louis, Mo.), catalog number 7060B.

Compound 124 was purchased from Fischer-Scientific (Hampton, N.H.), Acros, catalog number 17.522.62

Compound 125 was purchased from Reike, Aldrich (St. Louis, Mo.), catalog number 7011D.

Compound 126 was purchased from Reike, Aldrich (St. Louis, Mo.), catalog number 7036B.

Compound 128 was purchased from Reike, Aldrich (St. Louis, Mo.), catalog number 7012D.

Compound 129 was purchased from Reike, Aldrich (St. Louis, Mo.), catalog number 7012B.

Compound 130 was purchased from Reike, Aldrich (St. Louis, Mo.), catalog number 7055B Compound 132 was purchased from Reike, Aldrich (St. Louis, Mo.), catalog number 7005b.

Compound 133 was purchased from Reike, Aldrich (St. Louis, Mo.), catalog number 7036F.

Compound 134 was purchased from Reike, Aldrich (St. Louis, Mo.), catalog number 7144D Compound 136 was purchased from Reike, Aldrich (St. Louis, Mo.), catalog number 7144B.

Compound 138 was purchased from Reike, Aldrich (St. Louis, Mo.), catalog number 7036D.

Compound 139

10-(2,5-Dihydroxy-phenyl)-10-oxo-decanoic acid

A 500 mL flask, equipped with a reflux condenser and under inert atmosphere, was charged with decanedioic acid (20 g, 296 mmol) and acetic anhydride (280 mL, 2.96 mol). The mixture was heated to reflux for 5 hours. Acetic acid and excess acetic anhydride was removed under reduced pressure. The product was used without further purification.

To a 500 mL flask, equipped with mechanical stirrer and under inert atmosphere, was added the previously made Oxacycloundecane-2,11-dione (37.95 g, 206 mmol), 1,4-diacetoxy-benzene (20 g, 103 mmol), and 200 mL carbon disulfide. Aluminum (III) trichloride (68.7 g, 515 mmol) was added and the reaction stirred for 72 hours. Carbon disulfide was decanted away, and ice was carefully added until most of mixture was dissolved. The insoluble material was collected by suction filtration and washed with 2×100 mL of water. The solid was then dissolved in 50 mL of 1 M aqueous sodium hydroxide and stirred for 1 hour. The solution was acidified with 1 M aqueous hydrochloric acid until pH=2. The crude product precipitate was collected by filtration and was re dissolved in acetonitrile (50 mL) and methylene chloride (15 mL) and allowed to precipitate slowly over a week. The resulting brown powder was collected by filtration and recrystallized from 10:3 acetic acid:water. The product (0.8 g, 3%) was isolated by filtration. Found: C, 65.55; H, 7.69%; $C_{16}H_{22}O_5$ requires C, 65.29; H, 7.53%; 1H NMR (d6-DMSO): δ 12.0, s, 1H (COOH); δ 11.4, s, 1H (aryl-hydroxyl); δ 9.2, s, 1H (aryl-hydroxyl); δ 7.2 d, 1H (aryl H); δ 7.0, dd, 1H, (aryl H); δ 6.8, d, 1H (aryl H's), 3.0, t, 2H ($CH_2$ α to carbonyl); δ 2.2, t, 2H ($CH_2$ α to COOH); δ 1.6, multiplet, 2H ($CH_2$ β to carbonyl), δ 1.5, multiplet, 2H ($CH_2$ β to COOH), δ 1.3, multiplet, 8H (rest of $CH_2$'s).

Example 4

Preparation of Compounds 140-151

Generally, the compounds were prepared in a four step process. First, the appropriate substituted salicylic acid and 3-amino butyric acid ethyl ester were mixed with ethylene dichloride (EDC)/hydroxybenzotriazole (HOBt)/Dichloromethane (DCM). Second, the basic ion exchange resin A-15/A-21 (available from Rohm and Haas, Philadelphia, Pa.) was added. Third, after partial workup, the product was reacted with potassium trimethylsilanolate (KOTMS)/tetrahydrofuran (THF). Forth, IRC-50 resin (Rhohm & Haas, Philadelphia, Pa.) was added.

To each scintillation vial was added a salicylic acid (4.57 mmol), DCM (10 mL), EDC (1.05 g, 5.48 mmol), HOBt (838 mgs, 5.48 mmol), DMF (2 mL), and ethyl-3-aminobutyrate (600 mgs, 4.57 mmol). All vials were capped tightly, placed on a J-Kem reaction block (J-Kem Scientific Inc., St. Lois, Mo.), and shaken and heated (150 rpm, 35° C.) overnight. Based on TLC, all reactions have one predominant spot. To each vial was added Amberlyst-21 and Amberlyst-15 resins (approximately 2.5 g, 11 mmol) and shaking at ambient temperature was continued overnight. The reactions were filtered, the resins washed with DCM (2×5 mL), and the combined filtrates of each reaction collected in a fresh scintillation vial. The filtrates were blown down under a stream of nitrogen to a volume of about 2 mL.

To each vial was added a 1.2 M solution of potassium trimethylsilanolate (KOTMS) in THF (10 mL, 12 mmol). More THF was added to some reactions as necessary to obtain shakable slurries. All vials were capped tightly, placed on a J-Kem reaction block, and shaken and heated (150 rpm, 60° C., 6 h). The reaction block was cooled, and IRC-50 resin (3 g, 30 mmol) was added to each vial to quench the potassium salt. DCM was added as necessary to suspend the resin and facilitate shaking. The reactions were shaken overnight. The reactions were filtered, the resins washed with DCM (2×5 mL), when necessary washed with DMF to dissolve solids, and the combined filtrates of each reaction collected in a fresh, tared scintillation vial. At this point small aliquots of the filtrates were taken and diluted with 1:1 ACN/H$_2$O for LC-MS. The filtrates were blown down under a stream of nitrogen. To remove traces of DMF, the vials were placed in a 50° C. vacuum oven.

Based on LC-MS analysis, some reaction mixtures still contained considerable amounts of ester. These library members were retreated with KOTMS. To each vial was added a 1.2 M solution of KOTMS in THF (8 mL, 9.6 mmol). All vials were capped tightly, put in a Pierce reaction block, stirred and heated (60° C., 5 h). The reaction block was cooled, and IRC-50 resin (2 g, 20 mmol) was added to each vial to quench the potassium salt. DCM was added as necessary to suspend the resin and facilitate stirring. The reactions were stirred over the weekend. The reactions were filtered through a plug of silica, the resins and silica washed with DCM (1×5 mL), then 2:5 MeOH/DCM (3×7 mL) and the combined filtrates of each reaction collected in a fresh, tared scintillation vial. At this point small aliquots of the filtrates were taken and diluted with 1:1 ACN/H$_2$O for LC-MS. The filtrates were blown down under a stream of nitrogen.

All other reaction mixtures from the first KOTMS treatment were taken up in 10:1 DCM/MeOH and filtered through a plug of silica, eluting with more 10:1 DCM/MeOH. At this point small aliquots of the filtrates were taken and diluted with 1:1 ACN/H$_2$O for LC-MS. The filtrates were blown down under a stream of nitrogen.

Alternative Preparation of Compound 140-151

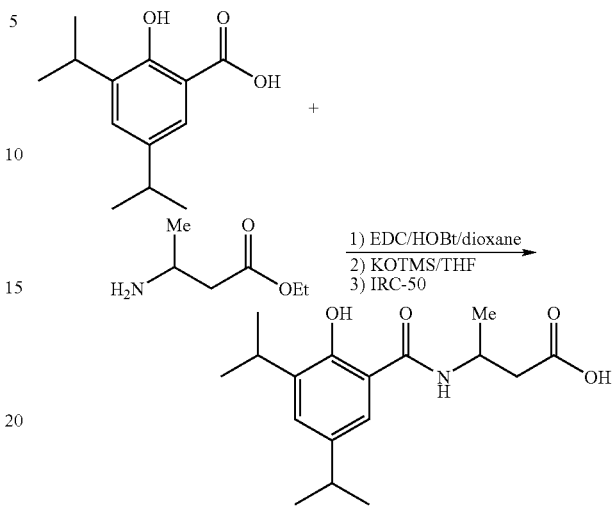

To a 1 L round-bottomed flask was added 3,5-diisopropylsalicylic acid (25.0 g, 112.5 mmol), HOBt (20.6 g, 135.0 mmol), ethyl-3-aminobutyrate (18.0 g, 123.7 mmol) and dioxane (400 mL). The resulting mixture was stirred at ambient temperature. EDC (25.9 g, 135.0 mmol) was added in portions and stirring continued overnight. An HPLC of the reaction mixture at this point showed HOBt, perhaps a trace of starting salicylic acid, and one new predominant product. Another portion of EDC (5 g, 26.0 mmol) was added and stirring continued overnight. Another HPLC showed essentially no change. The reaction was quenched with water (400 mL) and the dioxane stripped off by rotary evaporator. The resulting oil/water mixture was poured into a 1 L separatory funnel and DCM (400 mL) was added. Lots of white solid formed. EtOAc was added in an attempt to get separation of layers, with no success. The separatory funnel was drained and the mixture stripped of organics on the rotary evaporator. The water/oil mixture was extracted with EtOAc (500 mL, then 200 mL). The combined EtOAc layers were washed with aqueous HCl (10%, 2×200 mL), aqueous NaOH (10%, 2×200 mL) and brine (50 mL, then 200 mL). The organics were dried over Na$_2$SO$_4$ and stripped down on the rotary evaporator to a brown oil that contained small amounts of white solid. HPLC analysis indicates the white solid is residual HOBt, and the brown oil is desired product. The brown oil was pipetted out of the flask, avoiding as much of the white solid as possible. The brown oil was taken up in EtOAc (500 mL), washed with NaOH (10%, 2×200 mL) and dried over Na$_2$SO$_4$. The EtOAc was stripped off on the rotary evaporator to obtain the brown oil. HPLC at this point indicates one predominant peak and no HOBt.

The viscous oil was dissolved in THF (200 mL) and KOTMS (31.7 g, 247.4 mmol) was added. The resulting viscous mixture was stirred overnight. HPLC indicated reaction completion to one peak. Added IRC-50 resin (37 g, 370 mmol, 1.5 eq.) and 100 mL DCM to suspend the resin, then stirred several hours. Filtered, washed the resin with DCM (3×50 mL) and concentrated on the rotary evaporator to a brown oil. An attempt to recrystallize from ACN/acetone was unsuccessful. It was determined based on solubility at this point that the material was predominantly the potassium salt. The oil was taken up in H$_2$O/ACN, heated until clear, filtered while hot, and cooled to ambient temperature. The filtrate was treated with aqueous HCl and the resulting solid precipitate was isolated and ground into a powder to obtain E1528: 9.13 grams, HPLC rt 6.7 min 100%, KF 0.47, NMR consistent with structure, Elemental analysis theoretical C, 66.11; H, 8.21; N, 4.54. found C, 65.62; H, 8.19; N, 4.46.

| Compound Number and Name | MW | MS (M + H) | Approximate percent purity based on LC-MS |
|---|---|---|---|
| Compound 140 3-(2-Hydroxy-benzoylamino)-butyric acid | 223.2306 | 224 | 83 |
| Compound 141 3-(3,5-Dibromo-2-hydroxy-benzoylamino)-butyric acid | 381.0326 | 382 | 71 |
| Compound 142 3-(3,5-Dichloro-2-hydroxy-benzoylamino)-butyric acid | 292.1206 | 292 | 77 |
| Compound 143 3-(2-Hydroxy-3,5-diiodo-benzoylamino)-butyric acid | 475.0234 | 476 | 82 |
| Compound 144 3-(2-Hydroxy-3-methyl-benzoylamino)-butyric acid | 237.2577 | 238 | 75 |
| Compound 145 3-(4-Chloro-2-hydroxy-benzoylamino)-butyric acid | 257.6756 | 258 | 82 |
| Compound 146 3-(2-Hydroxy-4-methoxy-benzoylamino)-butyric acid | 253.2571 | 254 | 75 |
| Compound 147 3-(5-Bromo-2-hydroxy-benzoylamino)-butyric acid | 302.1316 | 303 | 82 |
| Compound 148 3-(5-Chloro-2-hydroxy-benzoylamino)-butyric acid | 257.6756 | 258 | 78 |
| Compound 149 3-(2-Hydroxy-5-methoxy-benzoylamino)-butyric acid | 253.2571 | 254 | 77 |
| Compound 150 3-(2-Hydroxy-5-methyl-benzoylamino)-butyric acid | 237.2577 | 238 | 82 |
| Compound 151 3-(2-hydroxy-3,5-diisopropyl-benzoylamino)-butyric acid | 307.3931 | 308 | 89 |

Example 5

Obtaining Compounds 152-160

Compound 152—was purchased from Transworld Chemical (South Melborne, AUSTRALIA).
Compound 153—was purchased from Lancaster (Windham, N.H.).
Compound 154—was purchased from Avocado (Heysham, Lancashire, ENGLAND).
Compound 155—was purchased from Aldrich under catalog number 42919 (St. Louis, Mo.).
Compound 156—was purchased from Sigma-Aldrich (St. Louis, Mo.).
Compound 157—was purchased from Sigma (St. Louis, Mo.).
Compound 158—was purchased from Matrix Scientific (Columbia, S.C.).

| Compound | HPLC Retention Time | HPLC Protocol | KF Value | Melting Point Range Value | CHNC C | CHNC H | CHNF C | CHNF H |
|---|---|---|---|---|---|---|---|---|
| 152 | 5.41 | | 0 | | | | | |
| 153 | 5.1 min | 0.1% TFA | 0 | | 69.76 | 5.46 | | |
| 154 | 6.2 min | 0.1% TFA | 0 | | 74.98 | 6.29 | | |
| 155 | 5.21 | | 0 | | | | | |
| 156 | 5.82 min | 0.1% TFA | 0 | | | | | |
| 157 | 5.42 | | 0 | 184-186 | 73.67 | 5.3 | 72.56 | 4.91 |
| 158 | 5.47 | | 0 | 110-112 | 74.36 | 5.82 | 74.39 | 5.66 |
| 159 | 5.56 min | | | | 63.47 | 5.39 | 62.65 | 5.13 |
| 160 | 5.30 | | 0.3 | 67-70 | 73.45 | 5.32 | 73.08 | 5.37 |

Compound 160:

Potassium hydroxide (10.37 g, 184.8 mmol) was ground to a powder with a mortar and pestle and added to a 250 mL flask containing 75 mL of dimethyl sulfoxide and 2-hydroxy-benzoic acid methyl ester (7.03 g, 46.2 mmol). To this mixture was added benzyl bromide (7.91 g, 46.2 mmol) and allowed to mix for 4 hours with stirring. Water (100 mL) was added and the reaction stirred for an additional 30 minutes. The reaction was then cooled with an external ice bath to 0° C. and acidified with concentrated hydrochloric acid to a pH 1. The mixture was extracted with 3×230 mL ethyl acetate. The organic layers were combined and solvent removed under reduced pressure. The resulting yellow liquid was dissolved in ethyl acetate (50 mL) and washed with 2×30 mL water followed by 2×30 mL brine. The organic layer was dried over sodium sulfate, filtered, and solvent removed under reduced pressure. The resulting yellow liquid was dried under vacuum for several days, and white crystalline solid formed. The solid product was collected and dried further under vacuum. Product (8.04 g, 76%) was isolated as a white crystalline solid, mp 67-70° C. Combustion analysis: Found: C, 73.08; H, 5.37%; $C_{14}H_{12}O_3$ requires C, 73.45; H, 5.32%;

Example 6

Preparation of Compounds 160-167

Compound F was prepared according to the general scheme, wherein a 2-hydroxybenzophenone was alkylated with a bromoalkyl ester in the presence of a base, followed by cleavage of the ester moiety using potassium trimethylsilanoate

Compound 160

6-(2-(2-Hydroxybenzoyl)phenoxy)hexanoic acid

A 250 mL round bottom flask equipped with a magnetic stirrer bar and a reflux condenser was charged with 10.32 g (48.2 mmol) of 2,2'-dihydroxybenzophenone and 100 mL of dimethylsulfoxide (DMSO). Potassium hydroxide (2.91 g, 51.9 mmol) that had been ground to a powder was added to the clear solution. The reaction mixture was heated to 45° C., until most of the solid had dissolved. The resulting red slurry was treated with 8.80 mL (11.04 g, 49.5 mmol) of ethyl 6-bromohexanoate. After stirring for 20 hr at 25° C., the clear reaction mixture was diluted with aqueous 1% hydrochloric acid and methyl t-butyl ether (MTBE). The layers were separated. The organic phase was washed with water (2×50 mL) and brine (1×40 mL), dried over sodium sulfate and concentrated. The residue was taken up in 100 mL of tetrahydrofuran (THF) and treated with potassium trimethylsilanoate (15.09 g, 118 mmol). The orange solution was stirred for 20 hr at 25° C., diluted with aqueous 4% hydrochloric acid to pH 7.5 and washed with MTBE. The organic phase was extracted with aqueous 3% sodium bicarbonate solution. The combined aqueous phases were acidified to pH 2 with aqueous 4% hydrochloric acid and extracted with 60 mL of MTBE. This organic phase was washed with brine (1×40 mL), dried over sodium sulfate and concentrated. The residue was purified by flash chromatography using 80% hexanes/ethyl acetate (spiked with 0.5% acetic acid). The product (4.2 g, 27%) was isolated as an off-white solid, mp 89-91° C. Combustion analysis: Found: C, 69.50; H, 6.04%; $C_{19}H_{20}O_5$ requires C, 69.50; H, 6.14% 1H NMR (d6-DMSO): δ 12.0, bs, 1H (COOH); δ 11.5, bs, 1H (OH); δ 7.5, t, 2H, (aryl H's); δ 7.4, dd, 1H (aryl H); δ 7.3, dd, 1H (aryl H); δ 7.15, d, 1H (aryl H); δ 7.1, t, 1H (aryl H); δ 7.0, d, 1H (aryl H); δ 6.9, t, 1H (aryl H); δ 3.9, t, 2H, (CH₂ α to O); δ 2.05, t, 2H(CH₂ α to COOH); δ 1.4, m, 4H (other two CH₂'s); δ 1.0, p, 2H(CH₂ in middle of chain).

The following compounds were prepared from the appropriate starting materials using the same procedure: Compound 161, Compound 162, Compound 163, Compound 164, Compound 165, Compound 166 and Compound 167.

Compound 161

Sodium 8-(2-(2-Hydroxybenzoyl)phenoxy)octanoate

Starting from 2,2'-dihydroxybenzophenone and ethyl 8-bromooctanoate, the title compound was prepared and then converted into the sodium salt as follows: the free acid (3.56 g, 9.99 mmol) was dissolved in 40 mL of isopropanol, and treated with sodium hydroxide solution (1.7 mL) prepared from of sodium hydroxide (0.90 g, 22.5 mmol) and water (3.7 mL). Isopropanol and MTBE were added causing a solid to precipitate. Heating this mixture caused most of the solid to dissolve. The remaining solids were removed by filtration. The off-white solid that formed upon cooling with dry ice was isolated by filtration and dried under reduced pressure. Combustion analysis: Found: C, 65.02%; H, 6.22%; $C_{21}H_{23}O_5Na$ requires C, 66.00; H, 6.65%; $^1H$ NMR (d6-DMSO): δ 12.6, bs, 1H (OH); δ 7.41, t, 1H, (aryl H); δ 7.31, t, 1H (aryl H); δ 7.27, dd, 1H (aryl H); δ 7.15, dd, 1H (aryl H); δ 7.03, d, 1H (aryl H); δ 6.97, t, 1H (aryl H); δ 6.91, d, 1H (aryl H); δ 6.65, t, 1H (aryl H); δ 3.83, t, 2H, (CH₂ α to O); δ 1.82, t, 2H (CH₂ α to COONa); δ 1.3, m, 4H (other two CH₂'s); δ1.0, m, 6H (CH₂'s in middle of chain). $^{13}C$ NMR (d6-DMSO): 198.59, 177.35, 161.35, 156.10, 134.56, 131.98, 131.78, 129.55, 128.57, 123.57, 120.18, 118.00, 117.09, 112.51, 67.74, 37.87, 28.83, 28.35, 28.27, 25.84, 24.87.

Compound 162

5-(2-(2-Hydroxybenzoyl)-4-methoxyphenoxy)valeric acid (major isomer data reported)

LC-MS analysis: m+1 peak confirmed (345). 1H NMR Analysis: (d6-DMSO): δ 12.4, bs, 1H (COOH); δ 11.9, bs, 1H (OH); δ 7.47, t, 1H, (aryl H); δ 7.26, dd, 1H (aryl H); δ 7.14, d, 1H (aryl H); δ 7.13, d, 1H (aryl H); δ 7.03, t, 1H (aryl H); δ 6.49, d, 1H (aryl H); δ 6.42, dd, 1H (aryl H); δ 3.95, t, 2H, (CH₂ α to O); δ 3.79, s, 3H, (CH₃O); δ 2.07, t, 2H (CH₂ α to COOH); δ1.48, p, 2H (CH₂ in chain); δ1.34, p, 2H (CH₂ in chain). $^{13}C$ NMR (d6-DMSO): 199.60, 174.18, 165.97, 163.34, 155.14, 135.14, 131.77, 128.29, 127.83, 120.46, 114.06, 112.69, 107.41, 100.70, 67.51, 55.76, 33.05, 27.80, 20.77.

Compound 163

5-(2-(2-Hydroxybenzoyl)phenoxy)valeric acid

LC-MS analysis: m+1 peak confirmed (315). 1H NMR Analysis: (d6-DMSO): δ 11.9, bs, 1H (COOH); δ 11.5, bs, 1H (OH); δ 7.50, dt, 1H, (aryl H); δ 7.48, dt, 1H, (aryl H); δ 7.35, dd, 1H (aryl H); δ 7.25, dd, 1H (aryl H); δ 7.14, d, 1H (aryl H); δ 7.06, t, 1H (aryl H); δ 6.96, d, 1H (aryl H); δ 6.85, t, 1H (aryl H); δ 3.93, t, 2H, (CH₂ α to O); δ 2.06, t, 2H (CH₂ α to COOH); δ1.42, p, 2H (CH₂ in chain); δ1.29, p, 2H(CH₂ in chain). $^{13}C$ NMR (d6-DMSO): 200.59, 174.15, 160.43, 155.71, 135.94, 132.69, 132.22, 128.58, 128.02, 121.50, 120.46, 119.06, 117.30, 112.67, 67.50, 33.05, 27.75, 20.70.

Compound 164

5-(2-(2-Hydroxy-5-methoxybenzoyl)-4-methoxyphenoxy)valeric acid

LC-MS analysis: m+1 peak confirmed (375). 1H NMR Analysis: (d6-DMSO): δ 12.4, bs, 1H (COOH); δ 12.0, bs, 1H (OH); δ 7.25, d, 1H, (aryl H); δ 7.21, d, 1H, (aryl H); δ 6.66, d, 1H (aryl H); δ 6.62, dd, 1H (aryl H); δ 6.48, d, 1H (aryl H); δ 6.42, dd, 1H (aryl H); δ 3.96, t, 2H, ($CH_2$ α to O); δ 3.81, s, 3H, ($CH_3O$); δ 3.80, s, 3H, ($CH_3O$); δ 2.08, t, 2H ($CH_2$ α to COOH); δ1.48, p, 2H ($CH_2$ in chain); δ1.34, p, 2H ($CH_2$ in chain). $^{13}$C NMR (d6-DMSO): 198.85, 174.20, 165.62, 164.14, 162.54, 157.11, 135.18, 130.22, 120.60, 114.44, 107.04, 105.51, 100.63, 99.24, 67.55, 55.69, 55.48, 33.06, 27.75, 20.77.

Compound 166

4-(2-(2-Hydroxybenzoyl)phenoxy)butyric acid

LC-MS analysis: m+1 peak confirmed (333). 1H NMR Analysis: (d6-DMSO): δ 12.0, bs, 1H (COOH); δ 7.46, m, 2H (aryl H's); δ 7.33, dt, 1H (aryl H); δ 7.29, d, 1H (aryl H); δ 6.82, t, 1H (aryl H); δ 3.77, t, 2H, ($CH_2$ α to O); δ 1.85, t, 2H ($CH_2$ α to COOH); δ1.35, p, 2H (middle $CH_2$ in chain). $^{13}$C NMR (d6-DMSO): 200.47, 173.92, 160.40, 155.57, 135.97, 132.64, 132.27, 128.64, 128.00, 121.52, 120.56, 119.10, 117.34, 112.62, 66.99, 29.55, 23.92.

Compound 167

4-(2-Chlorobenzoyl-4-methylphenoxy)butyric acid

LC-MS analysis: m+1 peak confirmed (333). 1H NMR Analysis: (d6-DMSO): δ 12.4, bs, 1H (COOH); δ 12.0, bs, 1H (OH); δ 7.23, d, 1H (aryl H, o to O); δ 3.74, t, 2H, ($CH_2$ α to O); δ 2.25, s, 3H, $CH_3$); δ 1.84, t, 2H ($CH_2$ α to COOH); δ1.33, p, 2H (middle $CH_2$ in chain). $^{13}$C NMR (d6-DMSO): 198.76, 173.97, 165.63, 164.10, 162.58, 156.99, 135.11, 130.29, 120.55, 114.45, 107.14, 105.67, 100.67, 99.16, 67.03, 55.69, 55.50, 29.56, 23.85.

Example Preparation of Compounds 168-173

Compound 168

4-(2-Benzoyl-5-methoxyphenoxy)butyric acid

A 100 mL mini-block tube equipped with a magnetic stir bar was charged with 4.56 g (20.0 mmol) of 2-hydroxy-4-methoxybenzophenone, 2.70 mL (3.68 g, 18.9 mmol) of ethyl 4-bromobutyrate and 40 mL of dimethylformainide (DMF). Potassium carbonate (2.96 g, 21.4 mmol) was added to the clear solution. The reaction mixture was heated to 80 C. After stirring for 20 hr at 25 C, the clear reaction mixture was diluted with water. The resulting solid was isolated by filtration. This solid was taken up in 30 mL of tetrahydrofuran (THF) and treated with 3.10 g (24.0 mmol) of potassium trimethylsilanoate. The orange solution was stirred for 20 hr at 25 C, diluted with aqueous 4% hydrochloric acid to pH 7.5 and washed with MTBE. The organic phase was extracted with aqueous 3% sodium bicarbonate solution. The combined aqueous phases were acidified to pH 2 with aqueous 4% hydrochloric acid and extracted with 60 mL of MTBE. This organic phase was washed with brine (1×40 mL), dried over sodium sulfate and concentrated. The resulting solid was purified by trituration using MTBE/hexanes. More of the product was isolated from the mother liquor. LC-MS analysis: m+1 peak confirmed (315). 1H NMR Analysis: (d6-DMSO): δ 12.0, bs, 1H (COOH); δ 7.6, d, 2H, (phenyl H's, o to CO); δ 7.56, t, 1H (phenyl H, p to CO); δ 7.44, t, 2H (phenyl H's, m to CO); δ 7.35, d, 1H (aryl H, o to CO); δ 6.64, m, 2H (aryl H's, m to CO); δ 3.88, t, 2H, ($CH_2$ α to O); δ 3.82, s, 3H, ($CH_3O$); δ 1.84, t, 2H ($CH_2$ α to COOH); δ1.53, p, 2H (middle $CH_2$ in chain). $^{13}$C NMR (d6-DMSO): 195.08, 173.91, 163.17, 158.33, 138.84, 132.37, 131.37, 128.67, 128.24, 120.87, 105.87, 99.02, 66.89, 55.53, 29.45, 23.79.

Other delivery agents were made with the same procedure: Compound 169, Compound 170, Compound 171, Compound 172 and Compound 173.

Compound 169

4-(2-Benzoyl-4-chlorophenoxy)butyric acid

LC-MS analysis: m+1 peak confirmed (319). 1H NMR Analysis: (d6-DMSO): δ 11.9, bs, 1H (COOH); δ 7.64, d, 2H, (phenyl H's, o to CO); δ 7.59, t, 1H (phenyl H, p to CO); δ 7.51, dd, 1H (aryl H, p to CO); δ 7.45, t, 2H (phenyl H's, m to CO); δ 7.36, d, 1H (aryl H, o to CO); δ 7.14, d, 1H (aryl H, m to CO); δ 3.87, t, 2H, ($CH_2$ α to O); δ 1.84, t, 2H ($CH_2$ α to COOH); δ1.53, p, 2H (middle $CH_2$ in chain). $^{13}$C NMR (d6-DMSO): 194.37, 173.82, 154.74, 136.96, 133.42, 131.56, 130.05, 128.97, 128.62, 128.29, 124.48, 114.61, 67.38, 29.37, 23.79.

Compound 170

4-(2-Benzoyl-4-bromophenoxy)butyric acid

LC-MS analysis: m+1 peak confirmed (363). 1H NMR Analysis: (d6-DMSO): δ 11.9, bs, 1H (COOH); δ 7.6, m, 3H, (aryl H's); δ 7.60, t, 1H (phenyl H, p to CO); δ 7.49, dd, 1H (aryl H, o to CO); δ 7.46, t, 2H (phenyl H's, m to CO); δ 7.09, d, 1H (aryl H, m to CO); δ 3.89, t, 2H, ($CH_2$ α to O); δ 1.82, t, 2H ($CH_2$ α to COOH); δ1.53, p, 2H (middle $CH_2$ in chain). $^{13}$C NMR (d6-DMSO): 194.28, 173.81, 155.19, 136.97 134.48, 133.42, 131.06, 130.48, 128.97, 128.62, 115.08, 112.02, 67.33, 29.35, 23.77.

Compound 171

4-(2-(2-Chlorobenzoyl-5-methylphenoxy)butyric acid

LC-MS analysis: m+1 peak confirmed (333). 1H NMR Analysis: (d6-DMSO): δ 12.0, bs, 1H (COOH); δ 7.54, d, 1H, (aryl H); δ 7.4, m, 2H (aryl H's); δ 7.33, dt, 1H (aryl H); δ 7.29, d, 1H (aryl H); δ 6.86, m, 2H (aryl H's, o to O); δ 3.77, t, 2H, ($CH_2$ α to O); δ 2.31, s, 3H, $CH_3$); δ 1.85, t, 2H ($CH_2$ α to COOH); δ 1.35, p, 2H (middle $CH_2$ in chain). $^{13}$C NMR (d6-DMSO): 193.31, 173.81, 158.34, 145.98, 141.38, 130.99, 130.56, 129.48, 129.43, 128.38, 127.00, 123.95, 121.46, 113.43, 66.95, 29.65, 23.70, 21.48.

Compound 172

4-(2-(2-Chlorobenzoyl-4-methylphenoxy)butyric acid

LC-MS analysis: m+1 peak confirmed (333). 1H NMR Analysis: (d6-DMSO): δ 11.95, bs, 1H (COOH); δ 7.43, m, 3H, (aryl H's); δ 7.34, m, 3H (aryl H's); δ 6.92, d, 1H (aryl H, o to O); δ 3.74, t, 2H, (CH$_2$ α to O); δ 2.25, s, 3H, CH$_3$); δ 1.84, t, 2H (CH$_2$ α to COOH); δ1.33, p, 2H (middle CH$_2$ in chain). $^{13}$C NMR (d6-DMSO): 193.92, 173.81, 156.15, 140.95, 135.37, 131.24, 130.40, 129.65, 129.56, 129.49, 128.62, 127.02, 126.45, 112.95, 67.07, 29.65, 23.75, 19.80.

Compound 173

4-(2-Benzoyl-4-chloro-5-methylphenoxy)butyric acid

LC-MS analysis: m+1 peak confirmed (333). 1H NMR Analysis: (d6-DMSO): δ 11.9, bs, 1H (COOH); δ 7.61, d, 2H, (phenyl H's, o to CO); δ 7.57, t, 1H (phenyl H, p to CO); δ 7.44, t, 2H (phenyl H's, m to CO); δ 7.33, s, 1H (aryl H, o to CO); δ 7.14, s, 1H (aryl H, m to CO); δ 3.87, t, 2H, (CH$_2$ α to O); δ 2.33, s, 3H, CH$_3$); δ 1.81, t, 2H(CH$_2$ α to COOH); δ1.49, p, 2H (middle CH$_2$ in chain). $^{13}$C NMR (d6-DMSO): 194.31, 173.83, 154.78, 139.80, 139.80, 137.39, 133.17, 128.91, 128.84, 128.51, 127.55, 124.69, 115.57, 67.32, 29.37, 23.80, 20.03.
Alternative Preparation of Compound F Compound F can alternately be prepared according to Friedel-Crafts acylation of aromatic compounds:

Taking the appropriate substituted phenol, and mixing it with the appropriate Bromoester, using K$_2$CO$_3$ as the base, reacting the product with the appropriate aromatic acid chloride in the presence of AlCl$_3$; or Taking the appropriate substituted salicylic acid, and mixing it with the appropriate Bromoester, using K$_2$CO$_3$ as the base. The product is converted to an acid chloride SOCl$_2$, which is than reacted with the appropriate substituted benzene in the presence of AlCl$_3$.

Example 8

Preparation of Compound 174

Compound 174 was prepared in three steps:
A. O-Acetyl-5-chlorosalicylic acid 10 g (57.9 mmol) 5-chlorosalicylic acid was weighed in a 100-mL round-bottomed flask, followed by the addition of acetic anhydride (12.8 mL, 115.9 mmol). The mixture was stirred for 5 minutes before adding concentrated sulfuric acid (2 drops). The reaction was refluxed for 3 hours. Progress of the reaction was monitored by HPLC. The reaction mixture was cooled to room temperature and poured into a beaker containing 2N HCl (200 mL) to precipitate the product out. The product was collected via vacuum filtration. A purity check by HPLC revealed the presence of impurities. The precipitate was stirred in water (150 mL) overnight in a 200-mL round-bottomed flask. The insoluble solid was collected via vacuum filtration. An impurity check by HPLC revealed that the crude product was free of the impurities. The product was dried overnight in vacuo to yield 12 g of O-acetyl-5-chlorosalicylic acid (56 mmol, 97% yield)
B. O-acetyl-5-chlorosalicoyl chloride Thionyl chloride (~100 mL) was charged to a 250-mL round-bottomed flask and was stirred in an ice bath for 15 minutes. O-acetyl-5-chlorosalicylic acid (6.0 g, 27.9 mmol) was slowly added to the cooled thionyl chloride. DMF (2 drops) was added to the reaction mixture to aid in the dissolution of the acid. The reaction was stirred overnight to yield a homogenous solution. Excess thionyl chloride was distilled off in vacuo. The remaining residue was dried in vacuo overnight.

C. 3-(N-2-hydroxy-5-chlorobenzoyl)aminopropionic acid

β-Alanine (2.5 g, 28.0 mmol) was weighed in a 250-mL round-bottomed flask. Methylene chloride (100 mL) was added into the flask and the mixture was stirred for 5 minutes. Chlorotrimethylsilane (6.06 g, 55.7 mmol) was added dropwise to the flask. The reaction was heated to reflux for 1.5 hours. The mixture was allowed to cool to room temperature and was placed in an ice bath for 15 minutes. Triethylamine (8.5 g, 84.0 mmol) was slowly added to the cooled flask. O-Acetyl-5-chlorosalicoyl chloride (7.6 g, 27.9 mmol) was dissolved in methylene chloride (30 mL) and added to the reaction over 0.5 hours. The reaction was stirred overnight, and allowed to warm to room temperature. Progress of the reaction was confirmed by HPLC. The solvent was evaporated in vacuo. The remaining residue was stirred in 2N NaOH (~100 mL) for 2 hours and was slowly heated to 60° C. The solution was cooled to room temperature and then filtered by gravity filtration. The filtrate was slowly acidified with concentrated HCl until precipitates formed. The crude product was collected when the mixture was at pH 6. The product was recrystallized using MeOH—H$_2$O. Purity check by HPLC revealed the presence of impurities. The product underwent several purification and recrystallization steps until a pure compound was obtained. The final product was stirred overnight in methylene chloride, collected by filtration, and dried under vacuum overnight to yield a pale pink powder (3.98 grams, 16.3 mmol, 58.5% yield); mp 181-183° C.; 1HNMR (DMSO-d6) □ 2.47-2.58 (t, 2H), 3.44-3.54 (q, 2H), 6.93-6.98 (d, 1H), 7.39-7.44 (dd, 1H), 7.91-7.96 (d, 1H), 8.93-9.01 (t, 1H), 12.1-12.3 (s, 1H). KF value=1.615%. Analysis for calculated C10H10NO4Cl*0.2220H$_2$O: C, 48.50; H, 4.25; N, 5.66. Found: C, 48.20; H, 4.03; N, 5.43.

Example 9

Preparation of Compound 175-178

Compound 175

4-(2-Benzyloxy-phenoxy)-butyric acid

To a 250 mL flask, equipped with a reflux condenser, magnetic stirrer, and under inert atmosphere, was added 2-benzyloxy-phenol (8.0 g, 40 mmol), 4-bromobutanoic acid ethyl ester (5.7 mL, 40 mmol), potassium carbonate (7.2 g, 52 mmol), and ethanol (100 mL). The reaction mixture was heated to reflux with stirring for 8 hours. The reaction was cooled to room temperature and the insoluble byproduct was removed by suction filtration. 2N aqueous sodium hydroxide (30 mL) was added to the filtrate. This solution was heated to 50° C. for 2 hours. The solution was cooled to room temperature, the ethanol removed under reduced pressure, and the resulting solution was adjusted to pH 9. The aqueous solution was washed with ethyl acetate (2×30 mL) and residual ethyl acetate was removed under reduced pressure. The solution was cooled to 0° C. with an external ice bath and then acidified to pH 2 with 6N aqueous hydrochloric acid. The precipitated product was collected by suction filtration and dried under vacuum. The product (7.2 g, 63%) was isolated as a white powder. 1H-NMR (400 MHz, DMSO-d6): δ 12.0, s, 1H(COOH); δ 7.4, multiplet, 5H (Benzylic aryl H's); δ 7.0, multiplet, 2H (Aryl H's); δ 6.9, multiplet, 2H (Aryl H's); δ 5.0, s, 2H (Benzylic CH$_2$); δ 4.0, t, 2H (CH2 α to phenoxy); δ 2.4, t, 2H(CH2 α to COOH); δ 1.9, multiplet, 2H (remaining CH$_2$ group).

Compound 176—(4-Benzyloxy-phenoxy)-acetic acid was purchased from Lancaster.

Compound 177

11-(2-Benzyloxyphenoxy)undecanoic acid

To a 250 mL Erlenmeyer flask was added freshly ground potassium hydroxide (4.2 g, 74.91 mmol) and 100 mL dimethyl sulfoxide. 2-benzyloxy-phenol (5 g, 24.97 mmol) and 11-bromoundecanoic acid methyl ester (7 g, 25.07 mmol) was added and the mixture was allowed to stir at room temperature overnight. Water (75 mL) was added and the solution was heated to 85° C., with stirring, for 3 hours. The reaction was cooled to room temperature and acidified with concentrated hydrochloric acid to pH 2. The acidified solution was cooled to 4° C. for 2 hours, and the precipitate then collect by suction filtration. The product was recrystallized form ethanol/water. The product (8.88 g, 93%) was isolated as a light brown solid, mp 62-63° C. Combustion analysis: Found: C, 74.71; H, 8.08%; C24H32O4 requires C, 74.97; H, 8.39%;

Compound 178

5-(4-Benzyloxy-phenoxy)-pentanoic acid

To a 500 mL 3-neck flask equipped with a reflux condenser and under inert atmosphere, was added 4-benzyloxy-phenol (30.64 g, 150 mmol), 5-bromopentanoic acid ethyl ester (31.99 g, 150 mmol), potassium carbonate (22.80 g, 165 mmol), and 270 mL of 2-butanone. The reaction mixture was heated to reflux for 23 hours, cooled, and then diluted with ethyl acetate (150 mL) and extracted against water (500 mL). The organic layer was washed with water (1×250 mL) and brine (1×250 mL) and the solvent removed under reduced pressure. The resulting oil was dried under vacuum for 4 days, during which time a white crystals formed. The white crystals were dissolved in ethyl acetate (100 mL), washed with aqueous 1N sodium hydroxide (3×50 mL), and the solvent removed under reduced pressure. The resulting oil was dried under vacuum overnight to produce white crystals. The product was recrystallized from 1:1 ethanol:water and collected by suction filtration and dried under vacuum. This product was used without further purification.

To a 1 L round bottom flask, equipped with a reflux condenser, was added 5-(4-Benzyloxy-phenoxy)-pentanoic acid ethyl ester (15.13 g, 46 mmol) and 2N aqueous sodium hydroxide (47 mL). The mixture was allowed to stir for 30 minutes. Water (200 mL) was added. The mixture was stirred for 20 minutes then heated to reflux for 2 hours to form a brown solution. The solution was quickly cooled to room temperature by the addition of ice. The cooled solution was acidified with 2N aqueous hydrochloric acid (50 mL) and the resulting white precipitate was collected by suction filtration, washed with water (2×100 mL), hexanes (2×100 mL), and dried under vacuum over night. The powder was finely ground and washed with hexanes (1×250 mL) and diethyl ether (1×250 mL) to yield a white powder. This powder was dissolved in a mixture of ethyl acetate (300 mL) and diethyl ether (200 mL) in a 1 L beaker. The solution was heated for 10 minutes, methanol (5 mL) added, heated an additional 10 minutes, and then filtered through a Celite plug to yield a clear yellow solution. The product was crystallized by slow addition of hexanes. The first crop of crystals was collected by filtration and hexanes (200 mL) was added to the mother liquor. The solution was then concentrated under reduced pressure to a volume of 400 mL and allowed to rest. The second batch of crystals was collected by filtration and combined with the first. The product (8.92 g, 65%) was isolated as a white crystalline material, mp 127-128° C. Combustion analysis: Found: C, 71.01; H, 6.98%; C18H20O4 requires C, 71.98; H, 6.71%;

| Compound Sequence | HPLC Retention Time | KF Value | Melting Point Range Value | CHNC C | CHNC H | CHNF C | CHNF H |
|---|---|---|---|---|---|---|---|
| 175 | 5.93 min | | | | | | |
| 176 | 5.54 | 0 | | 69.76 | 5.46 | | |
| 176 | 5.54 | 0 | | 69.76 | 5.46 | | |
| 177 | 9.19 | 0 | 62-63 | 74.97 | 8.39 | 74.71 | 8.08 |
| 178 | 6.12 | 0 | 127-128 | 71.98 | 6.71 | 71.01 | 6.98 |

Example 10

Solid Oral Delivery of PYY[3-36] in Rats

PYY[3-36] stock solution (80 mg/ml) prepared with deionized water was used (PYY available from Bachem California Inc. of Torrance, Calif.).

About 0.08 mg/tablet (about 0.3 mg/kg) of PYY (about 1 μl) was added and blended with either about 13.5 or 27 mg/tablet (50 or 100 mg/kg) of the free acid or sodium salt of the Delivery Agent Compound, as indicated below. Upper punch, lower punch and die of Carver 4350 manual pellet press with a Caplet shape model sold by Natoli Engineering Company, Inc. (St. Charles, Mo.) were treated with magnesium stearate (0.1%). About 13.58 or about 27.08 mg of mixed powder was fed into the die and a mini bead shape tablet was made at about 1000 psi bar pressure. The resulting solid dosage form is about the size of a standard capsule size 9 (about 2.65 mm diameter and about 8.40 mm length) for the 27.08 mg size and about 2.65 mm diameter and about 4.20 mm length for the 13.58 mg solid.

Male Sprague Dawley rats (about 260 to about 280 g) were fasted overnight and then anesthetized by standard $CO_2$ inhalation technique for about 10 to 30 seconds resulting in an anesthetized state for about less then one minute, preferably about 10 to about 30 seconds.

An oral dosing tube was used. The dosing tube was inserted into the rat's mouth and carefully threaded down the rats pharynx and esophagus about 8 cm to about 15 cm depending on the weight of the rat (typically about 11 cm). The solid dosage form was delivered into the distal esophagus and/or stomach by pressing the plunger of the oral dosing tube.

Blood samples were collected retro-orbitally typically at time=0, 15, 30, 60 and 90 minutes. Serum PYY concentrations were quantified using a PYY[3-36] radioimmunoassay (Catalog #RK-059-02 from Phoenix Pharmaceuticals, Inc., Belmont, Calif.). Results from the animals in each group were averaged for each time point. The maximum of these averages (i.e., the mean peak serum PYY[3-36] concentration ± standard deviation (SD)) is reported below.

TABLE 1

PYY(3-36) Oral administration in rats.

| Delivery Agent Compound | Method of Administration | Compound dose (mg/kg) | PYY(3-36) dose (mg/kg) | Mean serum peak of PYY (pg/ml) ± SD |
|---|---|---|---|---|
| 23 - sodium salt | Oral, solid dose, 1 tablet per animal | 100 | 0.3 | 427.4 ± 258.7 |
| 121 - sodium salt | Oral, solid dose, 1 tablet per animal | 100 | 0.3 | 897.1 ± 257.3 |
| 121 - free acid | Oral, solid dose, 1 tablet per animal | 50 | 0.3 | 161.7 ± 148.5 |
| 174 - sodium salt | Oral, solid dose, 1 tablet per animal | 100 | 0.3 | 675 ± 427.1 |
| 174 - free acid | Oral, solid dose, 1 tablet per animal | 100 | 0.3 | 0 |

Example 11

PYY[3-36] Liquid Oral Delivery in Rats

Oral gavage (PO) dosing solutions of delivery agent compound and Peptide YY residues 3-36 (PYY[3-36]) (available from Bachem California Inc. of Torrance, Calif.) in deionized water were prepared as follows.

PYY [3-36] stock solution (80 mg/ml) was prepared with deionized water. Oral dosing compositions containing 200 mg/kg of delivery agent compound and 0.3 mg/kg of PYY in aqueous solution were prepared. A solution of the compound 23 is made with one equivalent to sodium hydroxide to convert the free acid delivery agent to its sodium salt.

Male Sprague-Dawley rats weighing between 240-320 g were fasted up to a maximum 24 hours before the experiments and administered ketamine (44 mg/kg) and thorazine (1.5 mg/kg) by intramuscular injection before the test article administration. Afterwards, the anesthetized animals were administered the test article by oral gavage. A dosing group of five animals was administered one of the dosing solutions. For oral gavage (PO), an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery, or by cardiac puncture, typically at time=0, 15, 30, 45, 60 and 90 minutes. Serum PYY concentrations were quantified using a PYY[3-36] radioimmunoassay (Catalog #RK-059-02 from Phoenix Pharmaceuticals, Inc., Belmont, Calif.). Results from the animals in each group were averaged for each time point. The maximum of these averages (i.e., the mean peak serum PYY[3-36] concentration ±standard deviation (SD)) is reported below in Table 2. No significant PYY [3-36] was detected in blood when the animals were dosed orally with PYY[3-36] alone.

TABLE 2

PYY(3-36) Oral administration (Liquid) in rats.

| Compound | Method of Administration | Compound dose (mg/kg) | PYY (3-36) dose (mg/kg) | Mean serum peak of PYY (pg/ml) ± SD |
|---|---|---|---|---|
| 23 | Oral (liquid dose) | 200 | 0.3 | 788.198 ± 50.59 |
| 151 | Oral (liquid dose) | 200 | 0.3 | 801.96 ± 290.61 |
| 158 | Oral (liquid dose) | 200 | 0.3 | 1065 ± 75.352 |
| 160 | Oral (liquid dose) | 200 | 0.3 | 370.39 ± 306.29 |
| 160 | Oral (liquid dose) | 200 | 0.3 | 631.96 ± 316.16 |
| 160 | Oral (liquid dose) | 200 | 0.3 | 705.106 ± 75.906 |
| 161 | Oral (liquid dose) | 200 | 0.3 | 340.95 ± 228.946 |
| 174 | Oral (liquid dose) | 200 | 0.3 | 1262.26 ± 313.58 |

Example 12

Human Recombinant Insulin Oral Delivery in Rats

Insulin (human recombinant) was obtained from ICN Biomedicals (Aurora, Ohio) as a bulk powder. To prepare stock solutions, insulin was dissolved in deionized water (pH~6.5) to obtain a concentration of 15 mg/ml. Stock solutions were kept frozen at −20° C. in 1.0-ml aliquots until used. For dosing solutions, the delivery agent compound was dissolved in deionized water to obtain a final concentration of 200 mg/ml. The free acid form of delivery agent was converted to the sodium salt by adding one equivalent of sodium hydroxide. Solutions were vortexed, sonicated, and heated, and if necessary, additional sodium hydroxide was added in μl quantities to achieve uniform solubility. Solutions were adjusted to a pH of 3.5-8.5 by the addition of either hydrochloric acid or sodium hydroxide. Insulin stock (typically 66.7 μl) was then added to the delivery agent solution to obtain a final concentration of 0.5 mg/ml. After solubilization and drug addition, solutions were brought to final volume by the addition of deionized water.

Insulin was administered to male, Sprague-Dawley rats either alone or in combination with an Emisphere delivery agent by oral gavage (PO). Typically, rats were fasted for 18-24 hours prior to dosing. For dosing, a Rusch 8 French catheter was cut to 11 cm in length and adapted to fit a 1-ml syringe. The syringe was filled with dosing solution and the catheter was wiped dry of excess solution. The catheter was inserted into the rat mouth and fed down the esophagus (10.0 cm). The dosing solution was delivered by pressing the syringe plunger while holding the rat in an upright position.
Sample Collection and Handling: Insulin During blood sampling, rats were exposed briefly (~10 sec) to carbon dioxide until prostrate, immediately prior to each sampling time point. For blood sampling, a 77-mm capillary tube was inserted into the retroorbital sinus. Typically, blood samples were collected prior to dosing (time 0) and at 15, 30, 45, and 60 minutes after dosing. Samples were collected into CAPIJECT® tubes (Terumo Corporation, Tokyo, Japan) containing a clot activator (red top, serum separator tubes). Samples were allowed to clot for ~20 min at 4° C. After clotting, samples were centrifuged at 10,000 rpm for 4 minutes at 6° C. in order to separate the serum. Serum was collected into eppendorf tubes and frozen at −20° C. until assayed.
Sample Collection and Handling: Whole Blood Glucose In order to determine the pharmacodynamic response, a hand-held glucometer (OneTouch Ultra, LifeScan® (Johnson & Johnson, New Brunswick, N.J.)) was used to measure whole blood glucose after administration of insulin or insulin and delivery agent. Samples were collected either from the retroorbital sinus (see Sample collection and handling: Insulin) or from the tail artery (i.e. tail clip). For tail clipping, the tip of the tail was severed approximately 5 mm from the tip using a scalpel blade. After discarding the first drop of blood, a small sample (~5-10 µl) was touched to the glucometer test strip (OneTouch Ultra, LifeScan) and a blood glucose reading was generated by the meter. For each subsequent sampling time point, the clot formed at the tip of the tail was broken up and a fresh sample was collected. Typically, samples were collected prior to dosing (time 0) and at 15, 30, 45, and 60 minutes after dosing.

TABLE 3

Insulin Oral (liquid dose) administration to rats.

| Compound | Method of Administration | Delivery Agent Compound dose (mg/kg) | Insulin dose (mg/kg) | Maximum % drop in glucose from control ± SD |
|---|---|---|---|---|
| 24 | Oral (liquid dose) | 200 | 0.5 | −14.73 ± 17.64 |
| 25 | Oral (liquid dose) | 200 | 0.5 | −14.81 ± 12.99 |
| 26 | Oral (liquid dose) | 200 | 0.5 | −25.93 ± 14.86 |
| 27 | Oral (liquid dose) | 200 | 0.5 | −25.40 ± 30.61 |
| 28 | Oral (liquid dose) | 200 | 0.5 | −11.41 ± 18.92 |
| 29 | Oral (liquid dose) | 200 | 0.5 | −29.25 ± 6.97 |
| 140 | Oral (liquid dose) | 100 | 1 | Cmax = 81.16 ± 114.98 µIU/mL |
| 141 | Oral (liquid dose) | 100 | 1 | Cmax = 204.05 ± 60.88 µIU/mL |
| 142 | Oral (liquid dose) | 100 | 1 | Cmax = 118.16 ± 72.75 µIU/mL |
| 145 | Intracolonic | 50 | 0.1 | Cmax = 15.03 ± 7.80 µIU/mL |
| 145 | Oral (liquid dose) | 100 | 1 | Cmax = 3.92 ± 5.62 µIU/mL |
| 160 | Oral (liquid dose) | 200 | 0.5 | Cmax = 74 ± 7.5 µIU/mL |
| 165 | Oral (liquid dose) | 200 | 0.5 | −33.0 |
| 166 | Oral (liquid dose) | 200 | 0.5 | −5.7 |
| 167 | Oral (liquid dose) | 200 | 0.5 | −21.2 |
| 167 | Oral (liquid dose) | 200 | 0.5 | −17.7 |
| 167 | Oral (liquid dose) | 200 | 0.5 | −26.2 |
| 167 | Oral (liquid dose) | 200 | 0.5 | −17.8 |
| 167 | Oral (liquid dose) | 200 | 0.5 | −22.7 |

Example 13

Human Zinc Insulin

Oral Delivery

Oral dosing (PO) compositions of delivery agent compound and human zinc insulin (minimum 26 IU/mg available from Calbiochem—Novabiochem Corp, La Jolla, Calif.) were prepared in deionized water. 500 mg of delivery agent compound was added to 1.5 ml of water. The free acid of the delivery agent compound was converted to the sodium salt by stirring the resultant solution and adding one equivalent of sodium hydroxide. The solution was vortexed, then heated (about 37° C.) and sonicated. The pH was adjusted to about 7 to 8.5 with NaOH or HCl. Additional NaOH was added, if necessary, to achieve uniform solubility, and the pH re-adjusted to about 7 to 8.5. Water was then added to bring the total volume to about 2.4 ml and vortexed. About 1.25 mg insulin from an insulin stock solution (15 mg/ml made from 0.5409 g insulin and 18 ml deionized water, adjusting with HCl and NaOH to pH 8.15 and to obtain a clear solution using 40 ml concentrated HCl, 25 ml 10N NaOH and 50 ml 1N NaOH) was added to the solution and mixed by inverting. The final delivery agent compound dose, insulin dose and dose volume amounts are listed.

Male Sprague-Dawley rats weighing between about 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. For oral dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery, typically at time=15, 30, 60, 120 and 180 minutes. Serum insulin levels were determined with an Insulin ELISA Test Kit (Kit # DSL-10-1600 from Diagnostic Systems Laboratories, Inc., Webster, Tex.), modifying the standard protocol in order to optimize the sensitivity and linear range of the standard curve for the volumes and concentrations of the samples used in the present protocol. Serum human insulin concentrations (µU/ml) were measured for each time point for each of the five animals in each dosing group. The five values for each time point were averaged and the results plotted as serum insulin concentration versus time. (Previous experiments revealed no measurable levels of human insulin following oral dosing with human insulin alone.) The maximum (peak) and the area under the curve (AUC) are reported below in Table 5. For % change from baseline for Blood Glucose the ONE TOUCH® (Life Scan, Johnson & Johnson, New Brunswick, N.J.).

TABLE 4

Insulin - Oral Delivery

| Delivery Agent Compound | Delivery Agent Compound Dose (mg/kg) | Insulin Dose (mg/kg) | Volume dose (ml/kg) | Cmax (glucose) (µU/ml) | AUC | Glucose (% control) |
|---|---|---|---|---|---|---|
| 123 | 200 | 0.50 | | 107.3 | 7440 | |
| 125 | 200 | 0.50 | | 98.3 | 7687.5 | |
| 123 | 200 | 0.50 | | 100.3 | 7447.5 | |
| 115 | 200 | 0.50 | | 83.3 | 3232.5 | |
| 116 | 200 | 0.50 | | 89.5 | 3292.5 | |
| 118 | 200 | 0.50 | | 90.5 | 4327.5 | |
| 124 | 200 | 0.50 | | 87.8 | 1582.5 | |
| 134 | 200 | 0.50 | | 81.5 | 3817.5 | |
| 136 | 200 | 0.50 | | 91.5 | 4507.5 | |
| 138 | 200 | 0.50 | | 93.4 | 6907.5 | |
| 124 | 200 | 0.50 | | 59.9 | 112.5 | |
| 152 | 200 | 0.5 | | | | −29.3% |
| 153 | 200 | 0.5 | | | | −7.1% |
| 154 | 200 | 0.5 | | | | −7.9% |
| 159 | 200 | 0.5 | | | | −6.6% |
| 159 | 200 | 0.5 | | | 9.1 | −36.5% |

Example 14

Insulin

Pulmonary Delivery

Dosing compositions of delivery agent compound and human insulin in water were prepared. Typically, to 1.5 mg of delivery agent compound was added deionized water to bring the volume to 1.0 ml, and the solution was vortexed. Either the sodium salt of the delivery agent compound was used or the free acid was converted to the sodium salt by stirring the resultant solution and adding one equivalent of sodium hydroxide (10 N) and diluting with water. The solution was vortexed, then heated (about 37° C.) and sonicated. The pH was adjusted to between about 7.0 to 8.5 with NaOH or HCl. 75 μl human insulin stock solution (2 mg/ml) was added to the solution. (The stock solution was made as follows. To 0.02 g insulin was added 3 ml pH 3.0 HCl solution in deionized water. The pH of the resulting solution was brought to below 3.0 (about 2.6) with HCl and NaOH until the solution was clear. The pH was then raised to 7.6 using NaOH and HCl. The final volume was brought to 10 ml with pH 7.5 deionized water. Final pH 7.59.) Water was then added to bring the total volume to 2.0 ml, and the solution was inverted gently several times. The solution may be used in the dosing protocol immediately, or alternatively, the solution may be placed into a 37° C. water bath for one hour prior to dosing. The final delivery agent compound dose, insulin dose and volume dose amounts are listed below in Table 4.

The typical dosing and sampling protocols were as follows. Male Sprague-Dawley rats weighing between 200-250 g were fasted for 24 hours and administered ketamine (44 mg/kg) and chlorpromazine (3.0 mg/kg) 15 minutes prior to dosing and again as needed to maintain anesthesia (using the same amount of ketamine and 1.5 mg/kg chlorpromazine). Typically, a dosing group of five animals was administered one of the dosing solutions. A control group of five animals was dosed insulin alone. A tracheal instillator for rodents, equipped with light (available from Penn Century, Inc., Pittsburgh, Pa.) was filled with dosing solution and inserted down the throat until the needle went into the trachea (confirmed visually). The dosing solution was administered by pressing the plunger.

Blood samples from each animal were collected serially from the tail artery, typically at 5, 15, 30, 60 and 120 minutes after dosing. Serum insulin levels were determined with an Insulin ELISA Test Kit (Kit # DSL-10-1600 from Diagnostic Systems Laboratories, Inc., Webster, Tex.), modifying the standard protocol in order to optimize the sensitivity and linear range of the standard curve for the volumes and concentrations of the samples used in the present protocol. Serum insulin concentrations (μU/ml) were measured for each time point for each of the five animals in each dosing group. The five values for each time point were averaged and the results plotted as serum insulin concentration versus time. The ratio of the area under the curve (AUC) for the test group versus that of the control group is reported below. The ratio of the maximum serum insulin concentration (Cmax) for the test group versus that of the control group is also reported below.

TABLE 5

Pulmonary Delivery of Insulin

| Delivery Agent Compound | Volume dose (ml/kg) | Delivery Agent Compound Dose (mg/kg) | Insulin Dose (mg/kg) | Cmax |
|---|---|---|---|---|
| 174 | 0.4 | 16 | 0.03 | 18.36 ± 19.18 |

Example 15

Oral and Intracolonic Heparin Delivery

Oral gavage (PO) and/or intracolonic (IC) dosing solutions containing a delivery agent compound and heparin sodium USP in 25% aqueous propylene glycol were prepared. The sodium salt of the compound was used. Typically, delivery agent compound and heparin (about 166-182 IU/mg) were mixed by vortex as dry powders. This dry mixture was dissolved in 25% v/v aqueous propylene glycol, vortexed and placed in a sonicator (about 37° C.). The pH was adjusted to about 7 (6.5 to 8.5) with aqueous NaOH (2N). The dosing solution was sonicated to produce a clear solution. The final volume was adjusted to 3.0 mL. The final delivery agent compound dose, heparin dose and volume dose amounts are listed below in Table 6.

The typical dosing and sampling protocols were as follows. Male Sprague-Dawley rats weighing between 275-350 g were fasted for 24 hours and were anesthetized with ketamine hydrochloride (88 mg/kg) intramuscularly immediately prior to dosing. A dosing group of five rats was administered one of the dosing solutions. For oral gavage (PO) dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger. For intracolonic (IC) dosing, a 7.5 cm 8 fr Rusch catheter was adapted to a 1 ml syringe with a pipette tip. The dosing catheter was inserted into the colon through the anus until the tube was no longer visible. The dosing solution was injected slowly into the colon.

Citrated blood samples were collected by cardiac puncture following the administration of ketamine (88 mg/kg), typically at time—0.25, 0.5, 1.0 and 1.5 hours. Heparin activity was determined by utilizing the activated partial thromboplastin time (APTT) according to the method of Henry, J. B., Clinical Diagnosis and Management by Laboratory Methods, Philadelphia, Pa., W.B. Saunders (1979). Previous studied indicated baseline values of about 20 sec. Results from the five rats in each group were averaged for each time point. The maximum is reported below in Table 6.

TABLE 6

Oral/Intracolonic Delivery of Heparin

| Delivery Agent Compound | Method of Administration | volume dose (ml/kg) | Compound Dose (mg/kg) | Heparin Dose (mg/kg) | Mean Peak APTT (sec) ± SD | pH |
|---|---|---|---|---|---|---|
| 114 | IC | 1 | 50 | 25 | 42.90 ± 8.70 | 7.61 |
| 140 | IC | 1 | 50 | 25 | 23.49 ± 6.12 | 7.67 |
| 141 | IC | 1 | 50 | 25 | 52.40 ± 21.54 | 7.62 |
| 143 | IC | 1 | 50 | 25 | 114.69 ± 121.62 | 7.18 |
| 145 | IC | 1 | 50 | 25 | 134.42 ± 99.03 | 6.93 |
| 151 | PO | 3 | 300 | 100 | 252.09 ± 107.13 | |

TABLE 6-continued

Oral/Intracolonic Delivery of Heparin

| Delivery Agent Compound | Method of Administration | volume dose (ml/kg) | Compound Dose (mg/kg) | Heparin Dose (mg/kg) | Mean Peak APTT (sec) ± SD | pH |
|---|---|---|---|---|---|---|
| 151 | IC | 1 | 50 | 25 | 2.36 ± 1.27 (antifactor Xa) | 7.06 |
| 151 | IC | 1 | 25 | 25 | 3.39 ± 3.07 (antifactor Xa) | 7.23 |
| 160 | IC | 1 | 50 | 25 | 131 ± 154 (Tmax = 90 min) | |

Example 16

Parathyroid Hormone Delivery (PTH 1-34) Oral/Intracolonic Delivery

Oral gavage (PO) and/or intracolonic (IC) dosing solutions of delivery agent compound and human parathyroid hormone residues 1-34 (PTH) in water were prepared. The sodium salt of the delivery agent compound was used. Typically, a solution of the compound was prepared in water and stirred, adding one equivalent of sodium hydroxide (1.0 N) when making sodium salt. The final dosing solutions were prepared by mixing the compound with a PTH stock solution (PTH obtained from Eli Lilly and Co., Indianapolis, Ind.) (typically having a concentration of 5 mg PTH/ml) and diluting to the desired volume (usually 3.0 ml). The final compound, PTH and volume dose amounts are listed below in Table 7.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing. A dosing group of five rats was administered one of the dosing solutions. For oral gavage (PO) dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger. For intracolonic (IC) dosing, a 7.5 cm Rusch catheter tube (French 8 or 6) was adapted to a syringe with an Eppendorf pipette tip. The syringe was filled with the dosing solution by drawing the solution through the catheter tube. The catheter tube was wiped dry. K-Y jelly was applied to the tip, avoiding contact with the eye of the tube, and the tube was inserted into the colon through the anus until the tube was no longer visible. The solution was injected by pressing the syringe plunger, and the tube was removed.

Blood samples were collected serially from the tail artery, typically at time=0, 15, 30, 45, 60 and 90 minutes for oral and 0, 10, 20, 30, 60 and 90 for IC dosing. Serum PTH concentrations were quantified by an PTH radioimmunoassay kit (Kit # RIK 6101 from Peninsula Laboratories, Inc. San Carlos, Calif.). Previous studies indicated baseline values of about zero. Results from the five rats in each group were averaged for each time point. The maximum is reported below in Table 7.

TABLE 7

Oral/Intracolonic Delivery of PTH in Rats

| Delivery Agent Compound | Method of Administration | volume dose (ml/kg) | Compound Dose (mg/kg) | PTH Dose (ug/kg) | Mean Peak Serum [PTH] (pg/ml) ± SD | pH |
|---|---|---|---|---|---|---|
| 113 | Oral | 1 | 100 | 200 | 780.77 ± 439.92 | 8.18 |
| 113 | Oral | 1 | 100 | 200 | 53.51 ± 39.55 | 8.09 |
| 114 | Oral | 1 | 100 | 200 | 135.78 ± 136.97 | 8.41 |

Example 17

Interferon

Oral Delivery

Dosing solutions of delivery agent compound and interferon alfacon-1 (IFN) (available as Infergen® from InterMune, Inc. of Brisbane, Calif.) were prepared in deionized water. The free acid of the delivery agent compound was converted to the sodium salt with one equivalent of sodium hydroxide. Typically, a solution of the delivery agent compound was prepared in water and stirred, adding one equivalent of sodium hydroxide (1.0 N) when making the sodium salt. This mixture was vortexed and placed in a sonicator (about 37° C.). The pH was adjusted to about 7.0 to 8.5 with aqueous NaOH. The mixture was vortexed to produce a uniform suspension or solution, also using sonication and heat if necessary. Additional NaOH was added, if necessary, to achieve uniform solubility, and the pH re-adjusted to about 7.0 to 8.5. The delivery agent compound solution was mixed with an IFN stock solution (about 22.0 to 27.5 mg/ml in phosphate buffered saline) and diluting to the desired volume (usually 3.0 ml). The final delivery agent compound and IFN doses, and the dose volumes are listed below in Table 8.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery, typically at time=0, 15, 30, 45, 60 and 90 minutes. Serum IFN concentrations were quantified using Cytoscreen Immunoassay Kit for human IFN-alpha (catalog #KHC4012 from Biosource International, Camarillo, Calif.). Previous studies indicated baseline values of about zero. Results from the animals in each group were averaged for each time point. The maximum of these averages (i.e., the mean peak serum IFN concentration) is reported below in Table 8.

TABLE 8

Interferon - Oral Delivery

| Delivery Agent Compound | Delivery Agent Compound Dose (mg/kg) | IFN Dose (mg/kg) | Volume dose (ml/kg) | Mean Peak Serum [IFN] (ng/ml) ± SD | pH |
|---|---|---|---|---|---|
| 141 | 200 | 1 | 1 | 0.73 ± 0.44 | 8.29 |
| 147 | 200 | 1 | 1 | 1.27 ± 0.60 | 8.45 |
| 174 | 200 | 1 | 1 | 0.5 ± 0.57 | |
| 174 | 200 | 1 | 1 | 0.18 ± 0.17 | |
| 174 | 200 | 1 | 1 | 3.96 ± 2.72 | |
| 174 | 200 | 1 | 1 | 17.4 ± 9.12 | |

Example 18

Oral Delivery of Salmon Calcitonin (sCT)

Oral dosing (PO) compositions of delivery agent compound and salmon calcitonin (sCT) in water were prepared. Typically 450 mg of delivery agent compound was added to 2.0 mL of water. Either the sodium salt of the compound was used or the free acid was converted to the sodium salt by stirring the resultant solution and adding one equivalent of sodium hydroxide (1.0 N) and diluting with water. The solution was vortexed, then heated (about 37° C.) and sonicated. The pH was adjusted to about 7 (6.5 to 8.5) with NaOH or HCl. 90 μg sCT from a stock solution was added to the solution. Water was then added to bring the total volume to about 3.0 mL (varies depending on solubility of the delivery agent compound). The final delivery agent compound dose, sCT dose and volume dose amounts are listed below in Table 9.

Male Sprague-Dawley rate weighing between 200-250 g were fasted for 24 hours and administered ketamine (44 mg/kg) and chlorpromazine (1.5 mg/kg) 15 minutes prior to dosing. A dosing group of five rats was administered one of the dosing solutions. For oral dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger.

Blood samples were collected serially from the tail artery, typically at time=0, 10, 20, 30, 60 and 90 minutes. Serum sCT was determined by testing with a EIA kit (Kit # EIAS-6003 from Peninsula Laboratories, Inc., San Carlos, Calif.) modifying the standard protocol from the kit as follows: incubated with 50 μl peptide antibody for 2 hours with shaking in the dark, washed the plate, added serum and biotinylated peptide and diluted with 4 mL buffer, and shook overnight in the dark. Numbers were adjusted according to baseline values obtained at time=0. The results from the five rats in each dosing group were averaged for each time point. The maximum is reported below in Table 9.

TABLE 9

Oral delivery of Salmon Calcitonin (sCT)

| Delivery Agent Compound | Volume Dose (ml/kg) | Compound Dose (mg/kg) | sCT Dose (μg/kg) | Mean Peak Serum Sct (pg/ml ± SD) (SE) |
|---|---|---|---|---|
| 174 | 150 | 30 | 1 | 182.83 + 184.82 |
| 174 | 150 | 30 | 1 | 198.21 + 205.15 |
| 174 | 150 | 30 | 1 | 70.81 + 118.47 |

Example 19

Oral/Intracolonic Delivery of Recombinant Human Growth Hormone (rhGH)

Oral gavage (PO) and/or intracolonic (IC) dosing solutions of delivery agent compound and rhGH in phosphate buffer were prepared (rhHG available from Novartis, Basel, Switzerland). The sodium salt of the delivery agent compound was obtained by reacting the free acid with one equivalent of sodium hydroxide. The final dosing solutions were prepared by mixing the compound with an rhGH stock solution (15 mg rhGH/ml) and diluting to the desired volume (usually 3.0 ml). The compounds and rhGH dose amounts are listed below in Table 10.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing. A dosing group of five rats was administered one of the dosing solutions. For oral gavage (PO) dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger. For intracolonic (IC) dosing, a 7.5 cm Rusch catheter tube (French 8 or 6) was adapted to a syringe with an Eppendorf pipette tip. The syringe was filled with the dosing solution by drawing the solution through the catheter tube. The catheter tube was wiped dry. K-Y jelly was applied to the tip avoiding contact with the eye of the tube, and the tube was inserted into the colon through the anus until the tube was no longer visible. The solution was injected by pressing the syringe plunger, and the tube was removed.

Blood samples were collected serially from the tail artery or retroorbital sinus, typically at time=0, 15, 30, 45, 60 and 90 minutes for oral and 0, 10, 20, 30, 60 and 90 for IC dosing. Samples were collected into CAPIJECT® tubes (Terumo Corporation, Tokyo, Japan) containing a clot activator (red top, serum separator tubes). Samples were allowed to clot for ~20 min at 4° C. Serum rHGH concentrations were quantified by an rHGH immunoassay test kit (Kit #K1F4015 from Genzyme Corporation Inc., Cambridge, Mass.). The five samples from each time period were pooled. Previous studies indicated baseline values of about zero.

The maximum concentration for each group is reported below in Table 10.

TABLE 10

Oral/Intracolonic Delivery of rhGH in Rats

| Delivery Agent Compound | Method of Administration | volume dose (ml/kg) | Compound Dose (mg/kg) | rhGH Dose (mg/kg) | Mean Peak Serum Sct (ng/ml) |
|---|---|---|---|---|---|
| 160 | PO | 1 | 200 | 3 | — |
| 161 | PO | 1 | 200 | 3 | 1.033 (±2.31) (Tmax = 15 min) |
| 174 | PO | 1 | 200 | 3 | 57.42 |

All publications, references, patents, and published patent applications referred to herein are incorporated by reference.

The invention claimed is:

1. A compound selected from:

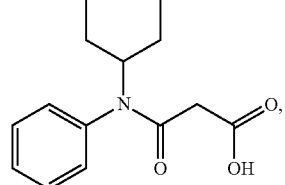
(Compound 3)

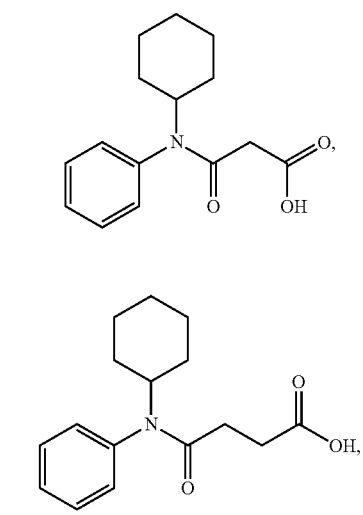
(Compound 4)

(Compound 6)

(Compound 7)

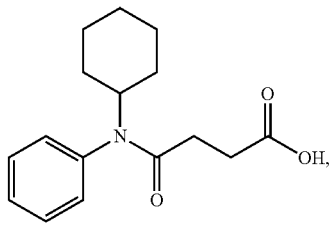

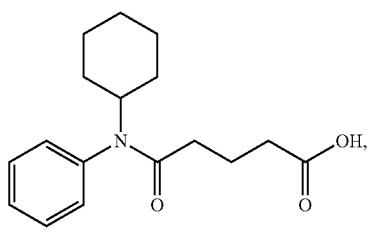

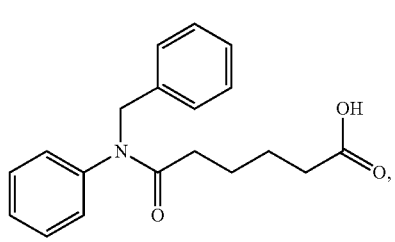

(Compound 8)
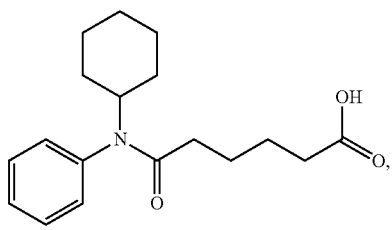

(Compound 10)
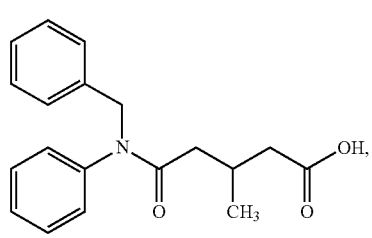

(Compound 11)

(Compound 12)

(Compound 13)

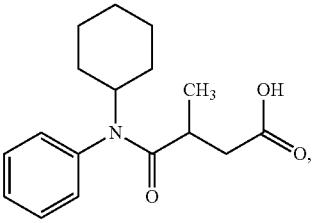

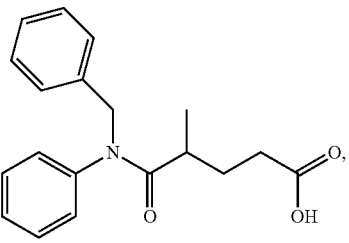

(Compound 14)

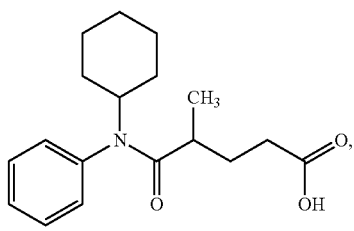

(Compound 15)

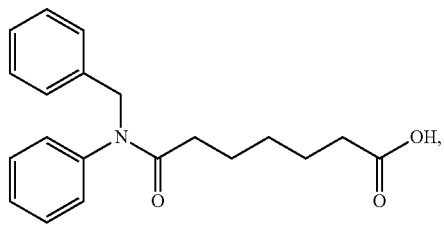

(Compound 16)

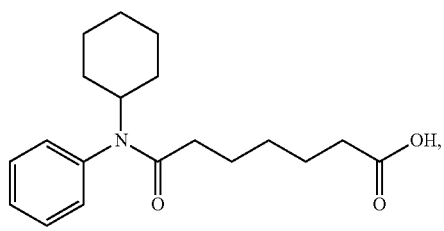

(Compound 18)

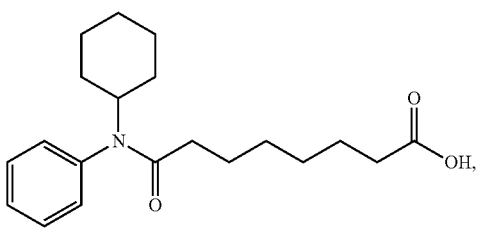

(Compound 19)

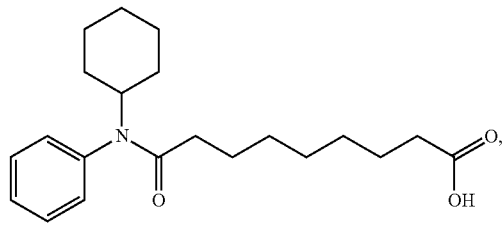

(Compound 20)

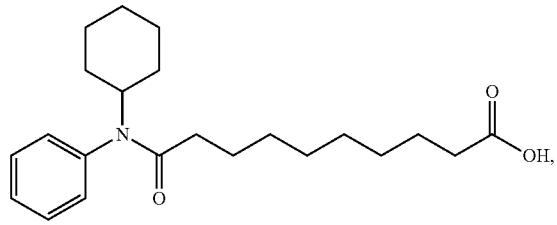

(Compound 21)

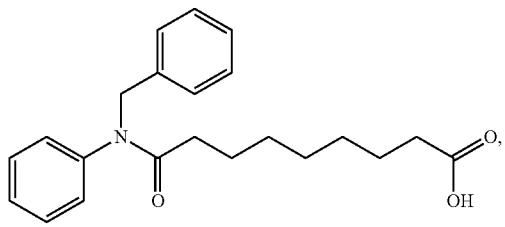

and salts thereof.

2. A pharmaceutical composition comprising:
(A) at least one biologically active agent; and
(B) a compound of claim 1.

3. The pharmaceutical composition of claim 2, wherein said biologically active agent is selected from the group consisting of Amylin, Amylin Agonists, Adrenocorticotropin, Antigens, Antimicrobials, Antibiotics, Anti-Bacteria's, Anti-Fungal Agents, Anti-Migraine Agents, Calcitonin Gene-Related Protein Antagonists, Sumatriptan Succinate, Antivirals, Atrial Naturetic Factor, Bisphosphonates, Salmon Calcitonin, Eel Calcitonin, Porcine Calcitonin, Human Calcitonin, Cholecystokinin (CCK), CCK Agonists; Cromolyn Sodium, Cyclosporine, Desferrioxamine (DFO), Erythropoietin, Exedin, Exedin Agonists, Filgrastim, Follicle Stimulating Hormone, Glucagon-Like Peptide 1 (GLP-1), Glucagon, Glucagon-Like Peptide 2 (GLP-2); Glucocerebrosidase, Gonadotropin Releasing Hormone, Growth Hormone Releasing Factor; Growth Hormone Releasing Hormones, Growth Hormones, Human Growth Hormones (hGH), Recombinant Human Growth Hormones (rhGH), Bovine Growth Hormones, Porcine Growth Hormones; Heparin, Unfractionated Heparin, Heparinoids, Dermatans, Chondroitins, Low Molecular Weight Heparin, Very Low Molecular Weight Heparin, Ultra Low Molecular Weight Heparin, synthetic heparins, Porcine Insulin, Bovine Insulin, Human Insulin, Human Recombinant Insulin; Insulin-Like Growth Factor, IGF-1; Interferons, α Interferons, β Interferons, θ Interferons, γ Interferons; Interleukin-1; Interleukin-2; Interleukin-11; Interleukin-21; Leutinizing Hormone, Leutinizing Hormone Releasing Hormone, Leptin, Monoclonal Antibodies, TNF-alpha soluble receptors, Oxytocin, Parathyroid Hormone (PTH), PTH fragments, PTH 1-34, PTH 1-38, Peptide YY (PYY), PYY Agonists, Prostaglandins; Protease Inhibitors, Somatostatin, Thrombopoietin, Vancomycin, Vasopressin, Vitamins, Vaccines, and combinations thereof.

4. A compound selected from:

Compound 23

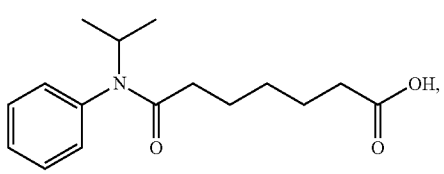

-continued
Compound 24
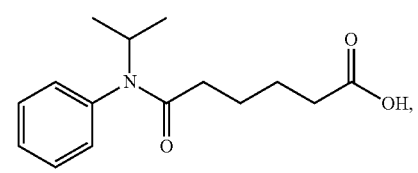
Compound 25
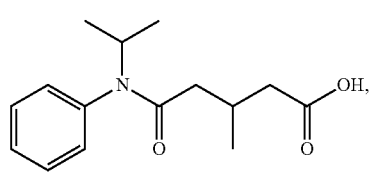
Compound 26
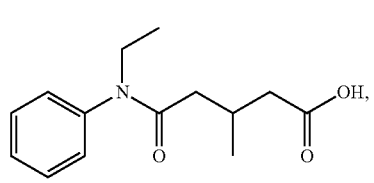
Compound 27
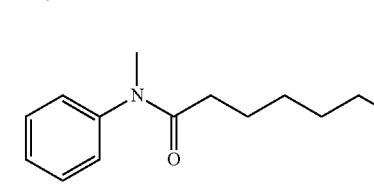
Compound 30
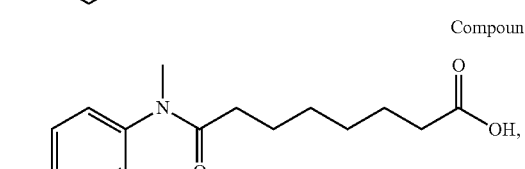
Compound 31
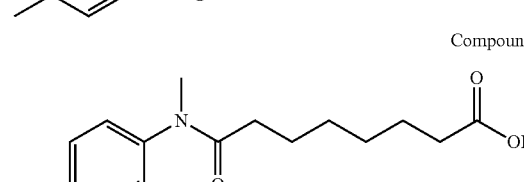
Compound 32
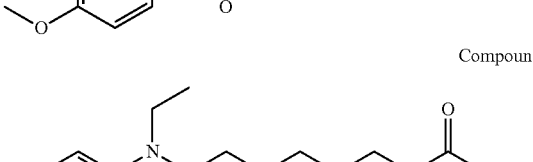
Compound 33
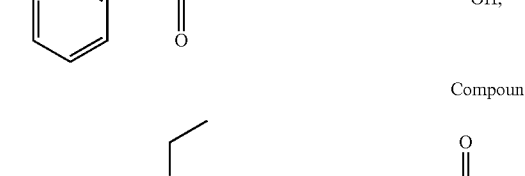
Compound 34
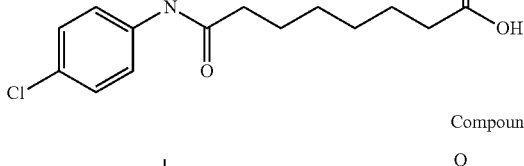
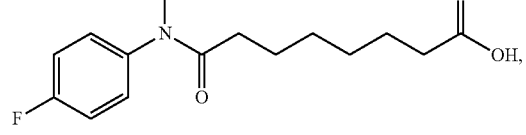
-continued
Compound 35
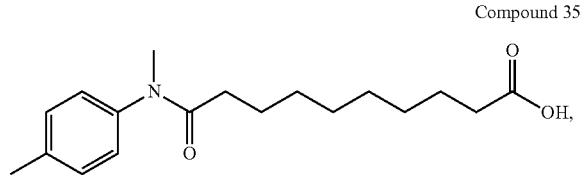
Compound 38
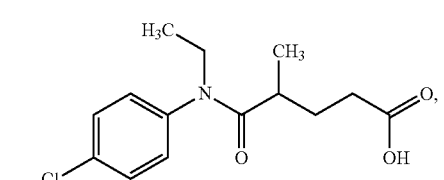
Compound 39
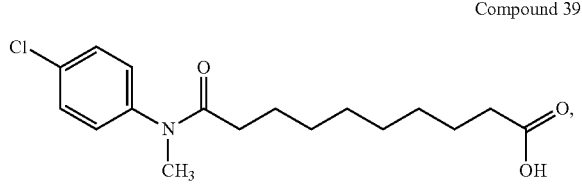
Compound 41
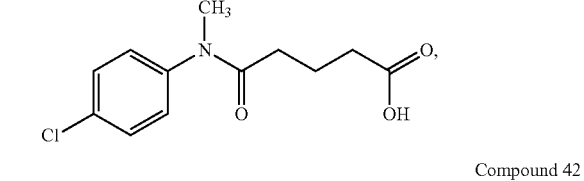
Compound 42
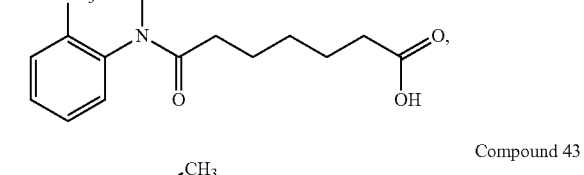
Compound 43
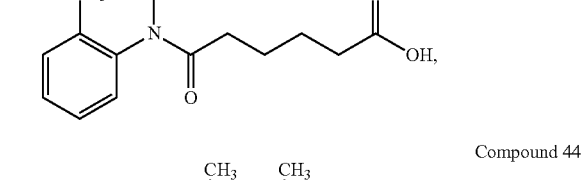
Compound 44
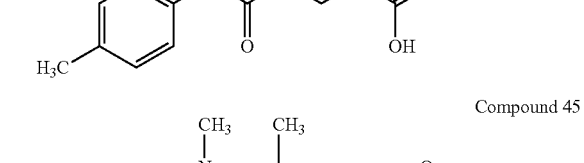
Compound 45
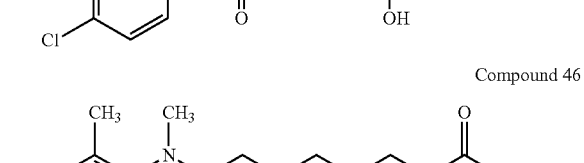
Compound 46

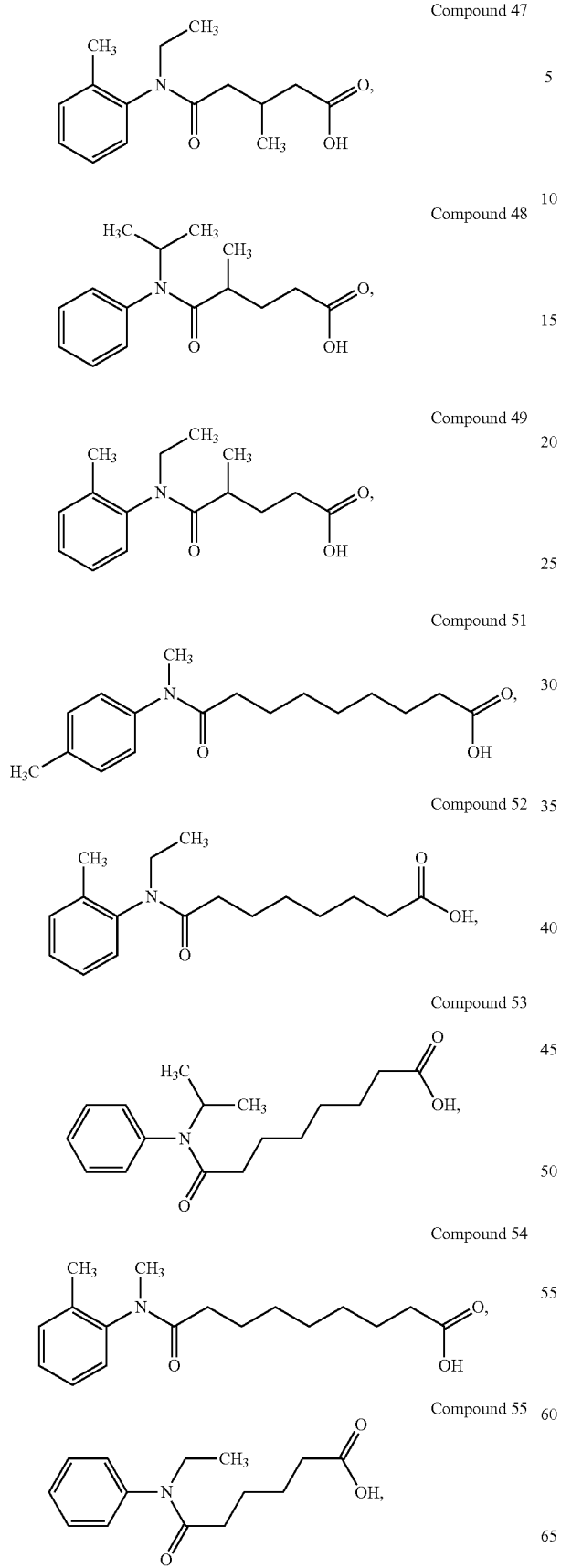
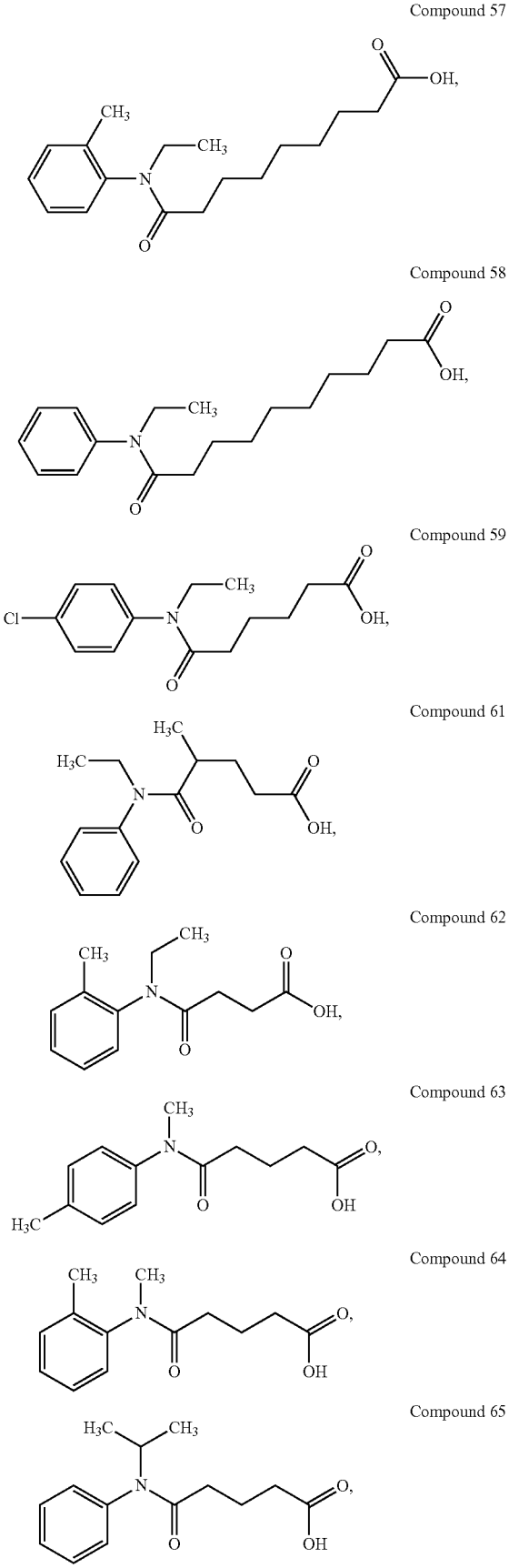

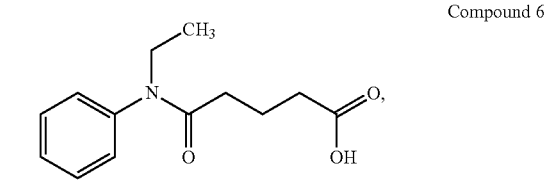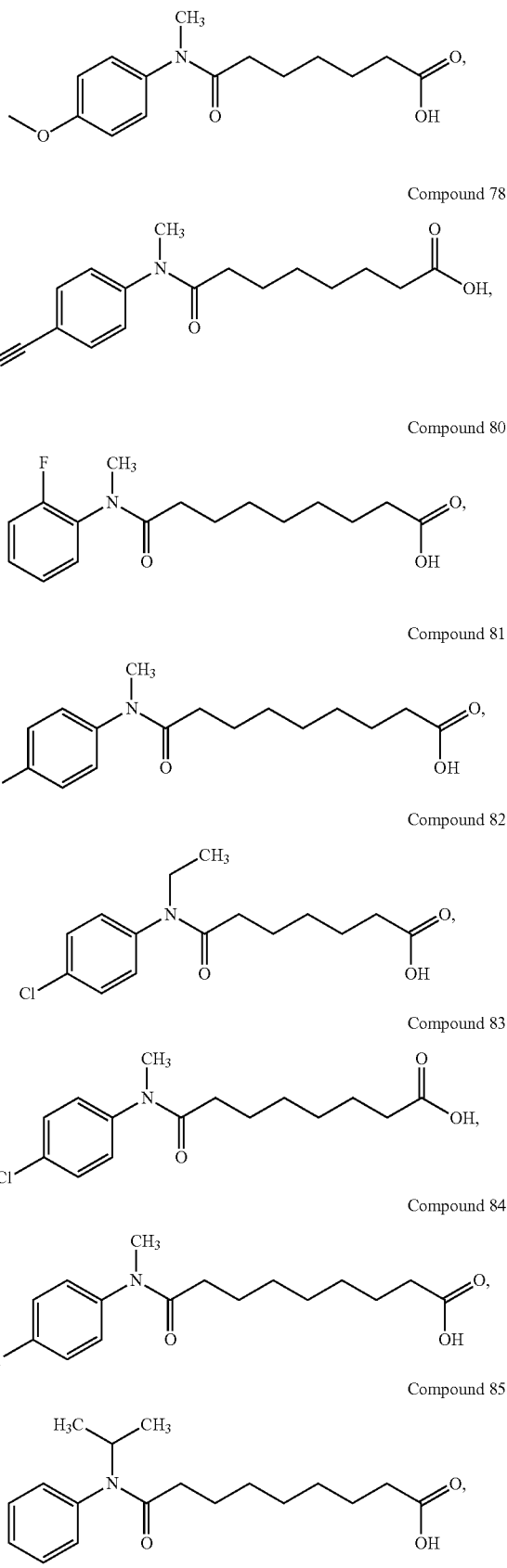

-continued

Compound 87, Compound 88, Compound 90, Compound 91, Compound 92, Compound 93, Compound 94, Compound 95, Compound 96, Compound 98, Compound 99, Compound 100, Compound 101, Compound 102, Compound 103, Compound 104, Compound 106, Compound 107

-continued
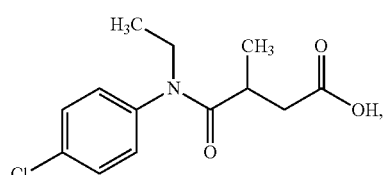
Compound 108
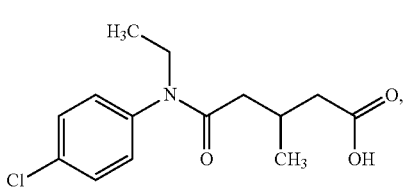
Compound 110
and salts thereof.
5. A pharmaceutical composition comprising:
(A) at least one biologically active agent; and
(B) a compound of claim 4.
6. A pharmaceutical composition comprising:
(A) at least one biologically active agent; and
(B) a compound selected from:
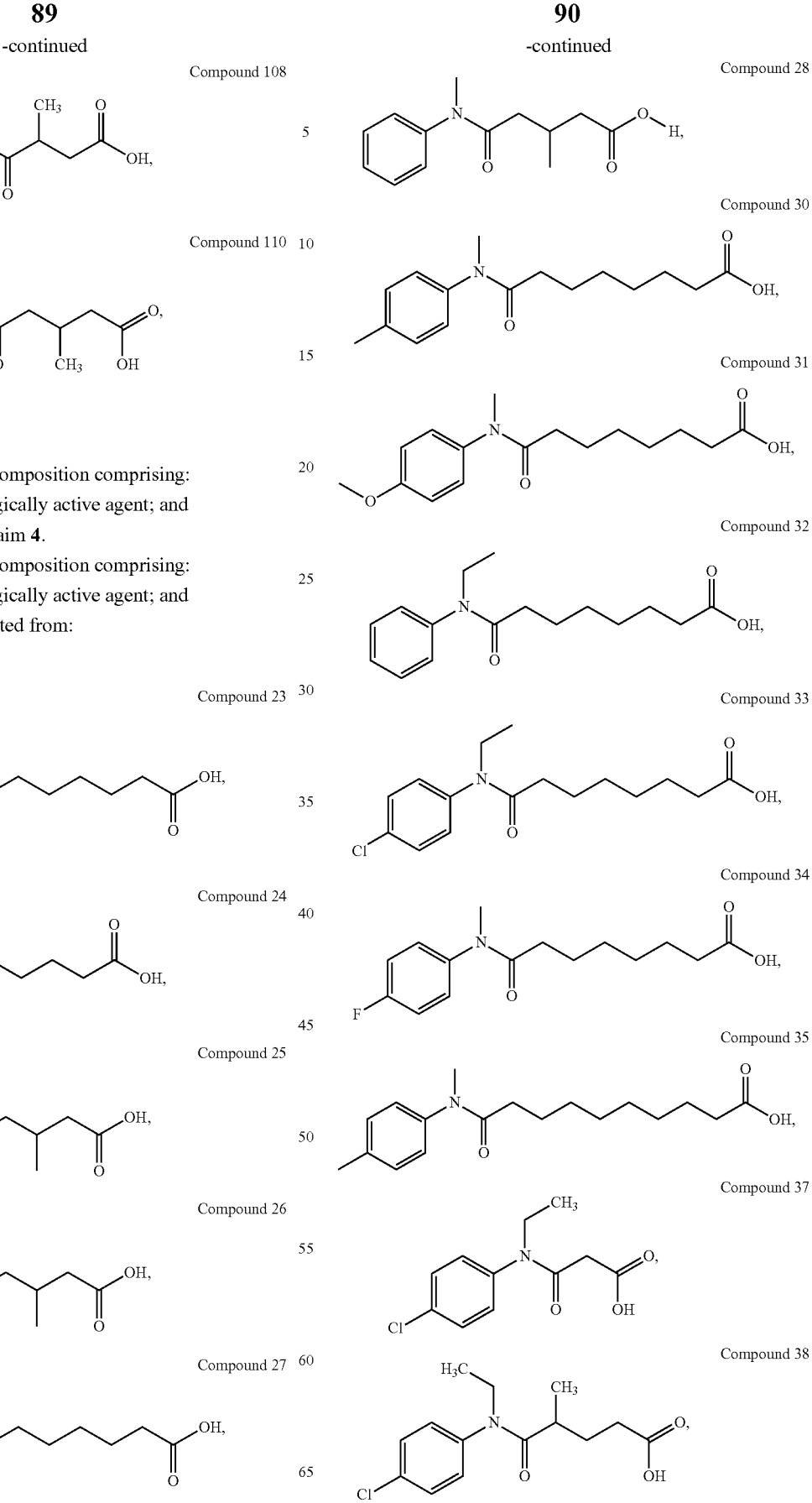

Compound 39
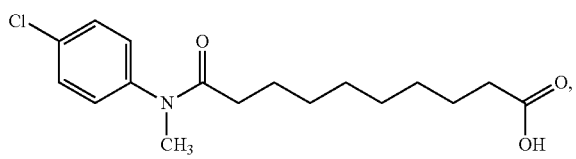
Compound 40
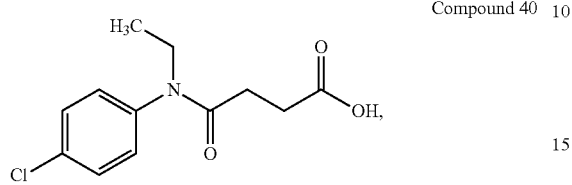
Compound 41
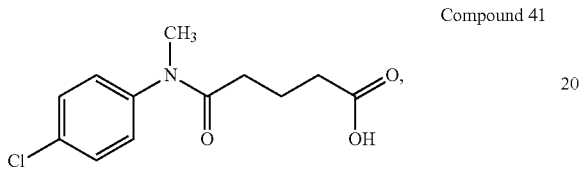
Compound 42
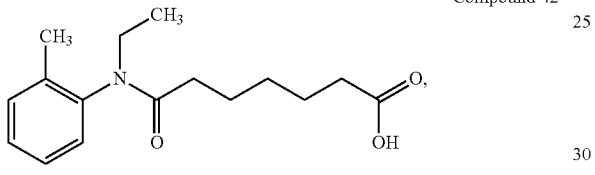
Compound 43
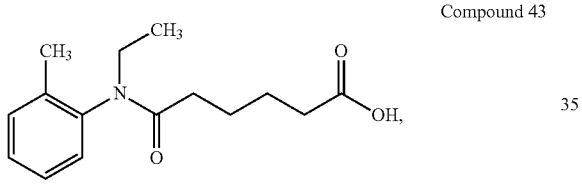
Compound 44
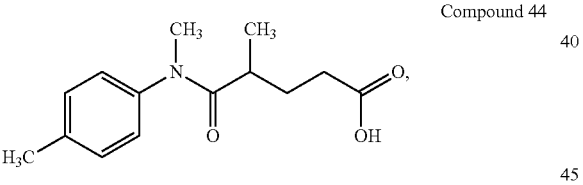
Compound 45
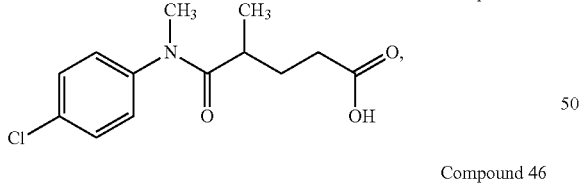
Compound 46
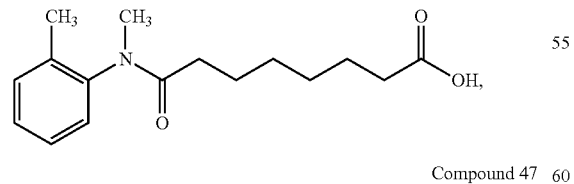
Compound 47
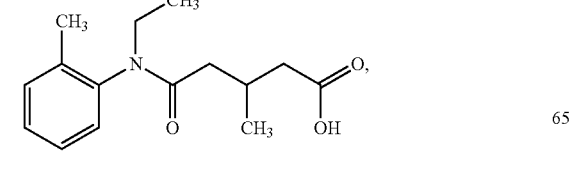
Compound 48
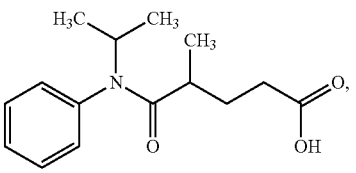
Compound 49
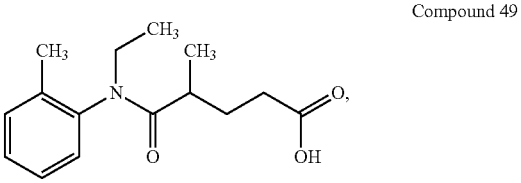
Compound 50
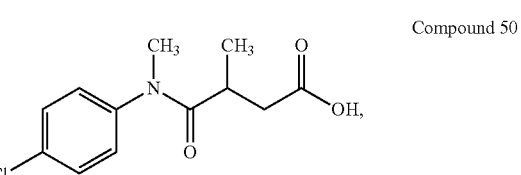
Compound 51
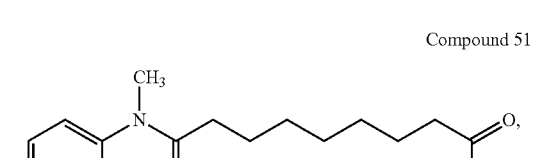
Compound 52
Compound 53
Compound 54
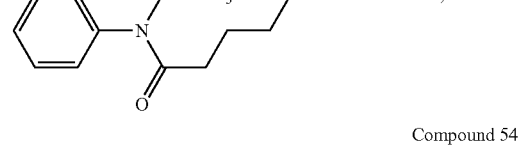
Compound 55
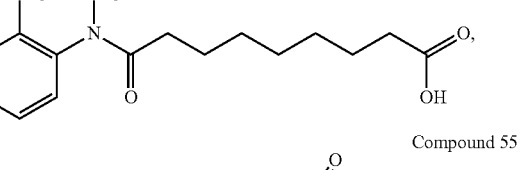

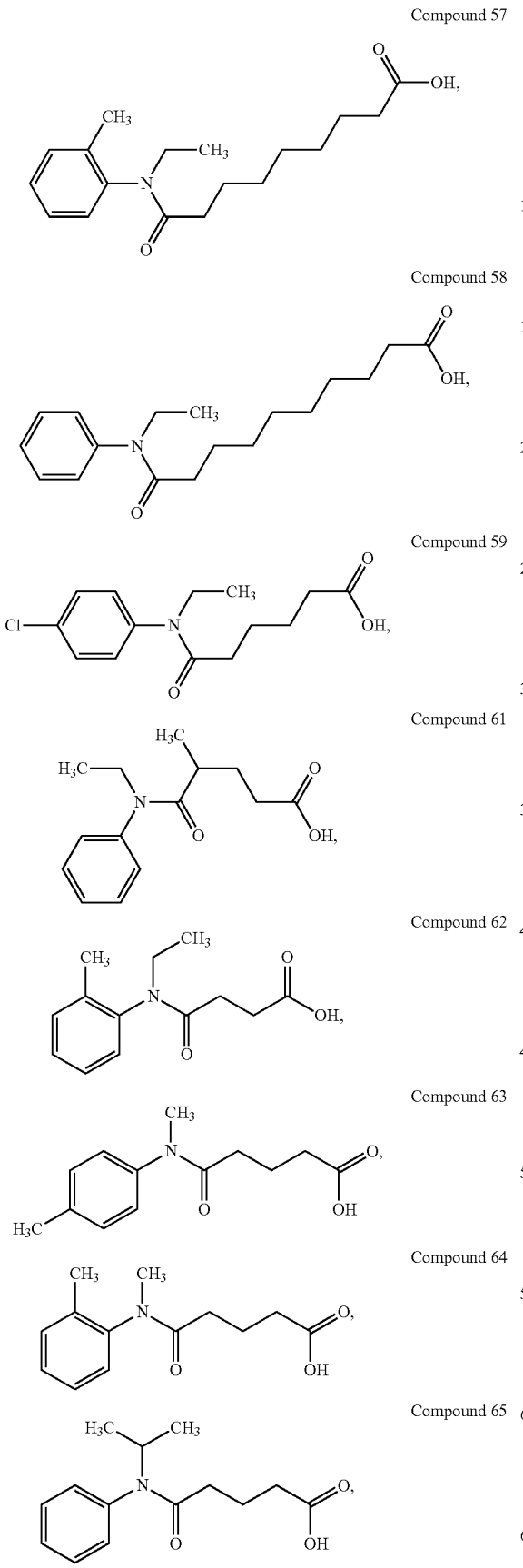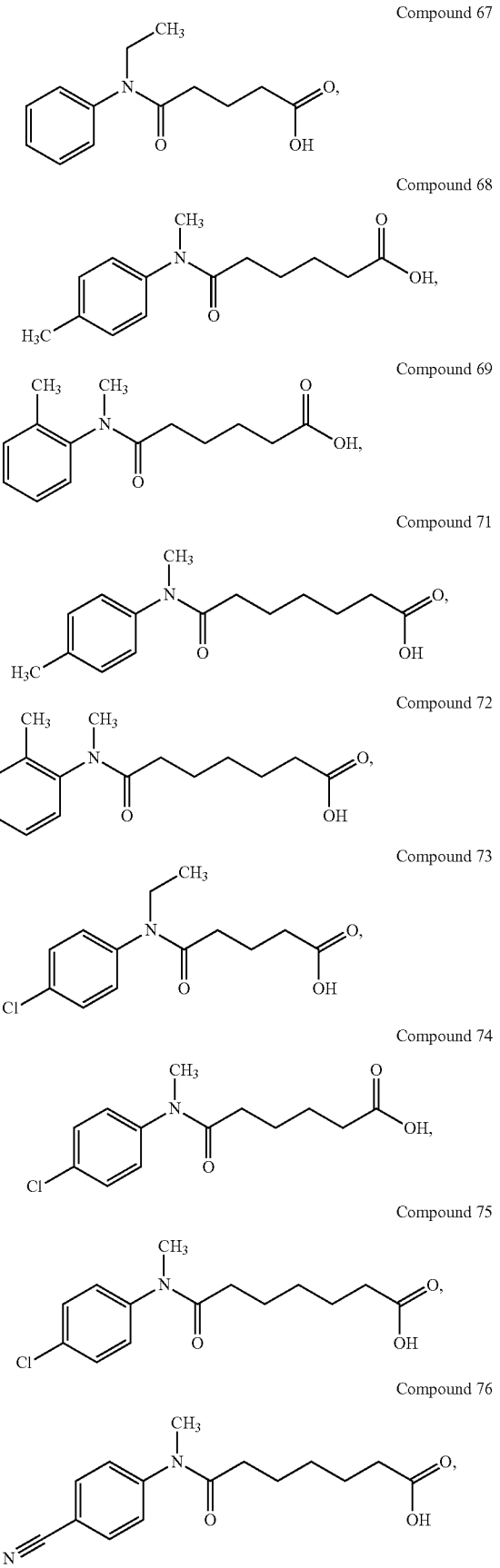

Compound 77
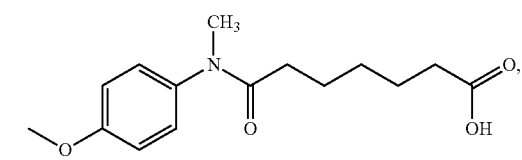
Compound 78
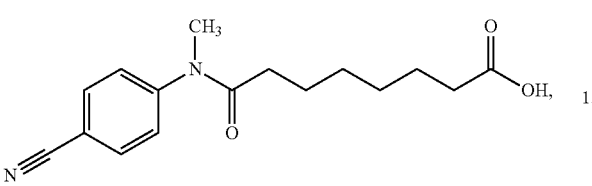
Compound 80
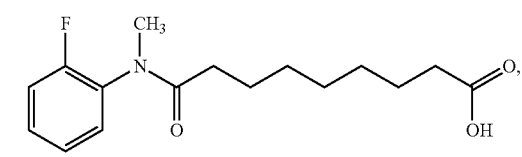
Compound 81
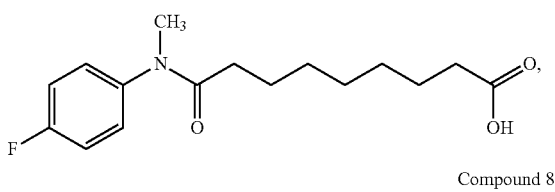
Compound 82
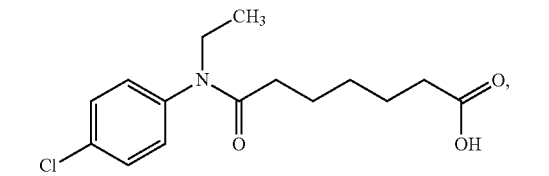
Compound 83
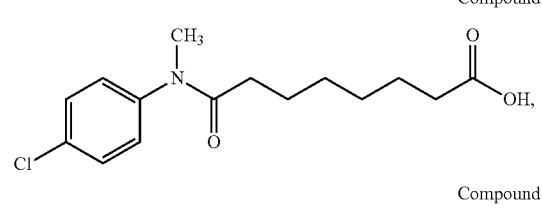
Compound 84
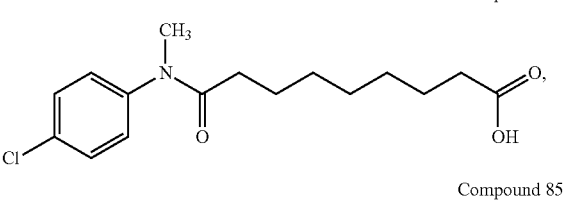
Compound 85
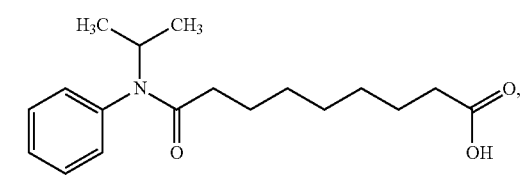
Compound 87
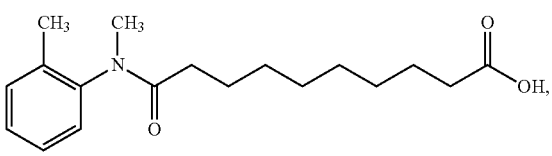
Compound 88
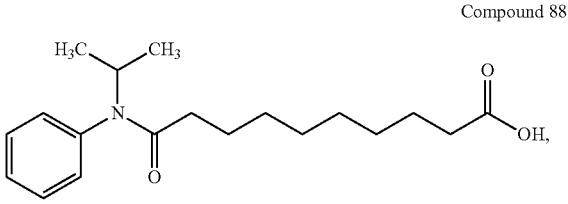
Compound 90
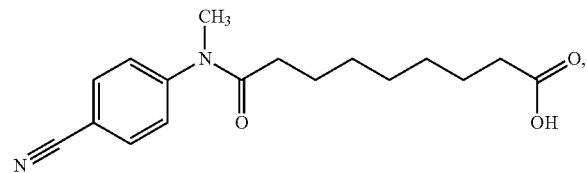
Compound 91
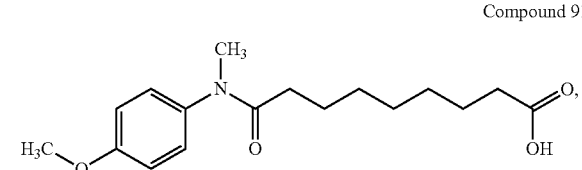
Compound 92
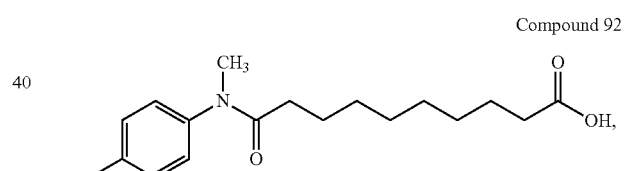
Compound 93
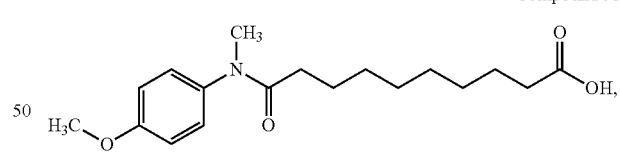
Compound 94
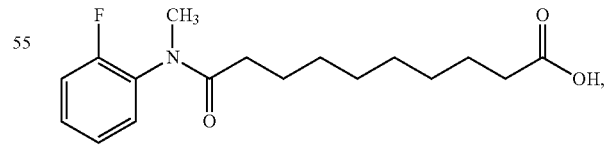
Compound 95
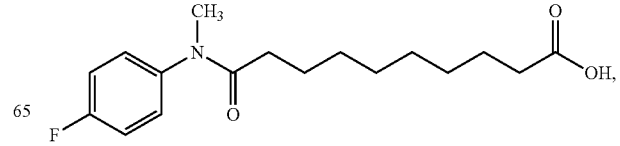

Compound 96
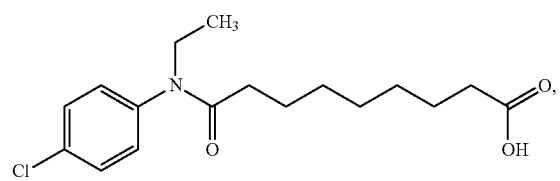

Compound 98
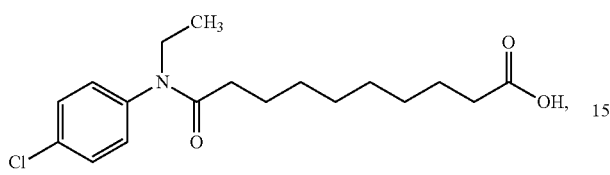

Compound 99
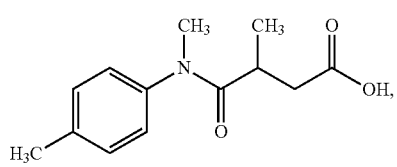

Compound 100
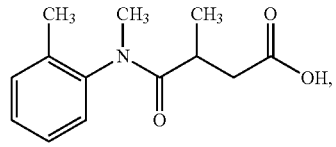

Compound 101
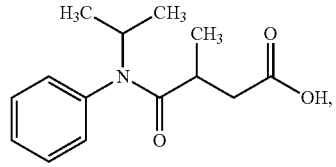

Compound 102
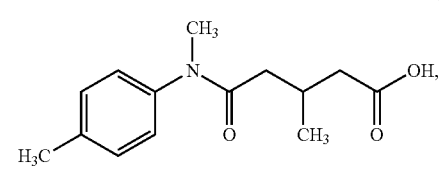

Compound 103
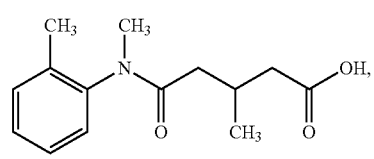

Compound 104
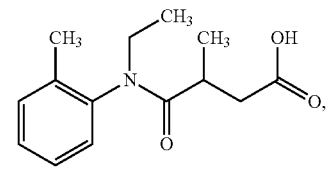

Compound 106
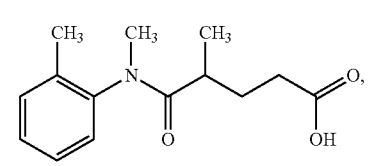

Compound 107
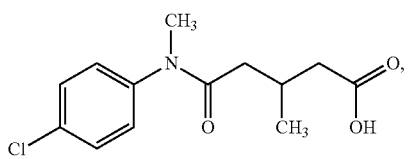

Compound 108
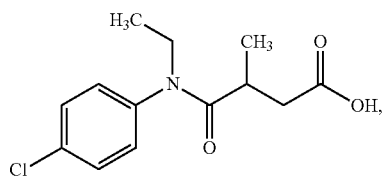

Compound 109
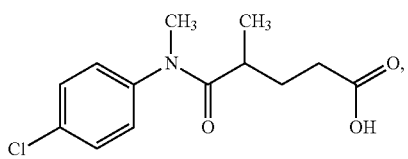

Compound 110
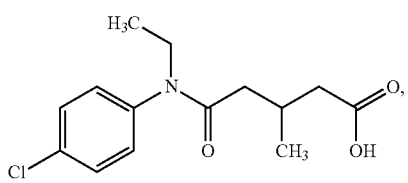

and salts thereof, wherein
said biologically active agent is selected from the group consisting of Amylin, Amylin Agonists, Adrenocorticotropin, Antigens, Antimicrobials, Antibiotics, Anti-Bacterials, Anti-Fungal Agents, Anti-Migraine Agents, Calcitonin Gene-Related Protein Antagonists, Sumatriptan Succinate, Antivirals, Atrial Naturetic Factor, Bisphosphonates, Salmon Calcitonin, Eel Calcitonin, Porcine Calcitonin, Human Calcitonin, Cholecystokinin (CCK), CCK Agonists; Cromolyn Sodium, Cyclosporine, Desferrioxamine (DFO), Erythropoietin, Exedin, Exedin Agonists, Filgrastim, Follicle Stimulating Hormone, Glucagon-Like Peptide 1 (GLP-1), Glucagon, Glucagon-Like Peptide 2 (GLP-2); Glucocerebrosidase, Gonadotropin Releasing Hormone, Growth Hormone Releasing Factor; Growth Hormone Releasing Hormones, Growth Hormones, Human Growth Hormones (hGH), Recombinant Human Growth Hormones (rhGH), Bovine Growth Hormones, Porcine Growth Hormones; Heparin, Unfractionated Heparin, Heparinoids, Dermatans, Chondroitins, Low Molecular Weight Heparin, Very Low Molecular Weight Heparin, Ultra Low Molecular Weight Heparin, synthetic heparins, Porcine Insulin, Bovine Insulin, Human Insulin, Human Recombinant Insulin; Insulin-Like Growth Factor, IGF-1; Interferons, α Interferons, β Interferons, θ Interferons, γ Interferons; Interleukin-1; Interleukin-2; Interleukin-11; Interleukin-21; Leutinizing Hormone, Leutinizing Hormone Releasing Hormone, Leptin, Monoclonal Antibodies, TNF-alpha soluble receptors, Oxytocin, Parathyroid Hormone (PTH), PTH fragments, PTH 1-34, PTH 1-38, Peptide YY (PYY), PYY Agonists, Prostaglandins; Protease Inhibitors, Somatostatin, Thrombopoietin, Vancomycin, Vasopressin, Vitamins, Vaccines, and combinations thereof.

7. A compound selected from:

Compound 141

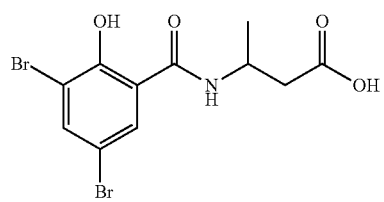

3-(3,5-Dibromo-2-hydroxy-benzoylamino)-butyric acid,

Compound 142

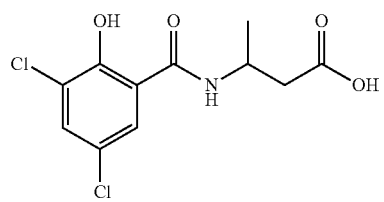

3-(3,5-Dichloro-2-hydroxy-benzoylamino)-butyric acid,

Compound 143

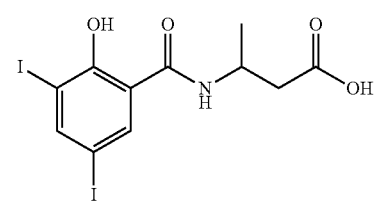

3-(2-Hydroxy-3,5-diiodo-benzoylamino)-butyric acid,

Compound 144

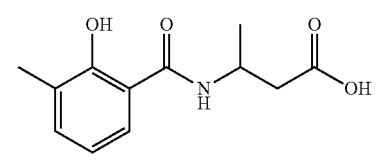

3-(2-Hydroxy-3-methyl-benzoylamino)-butyric acid,

Compound 145

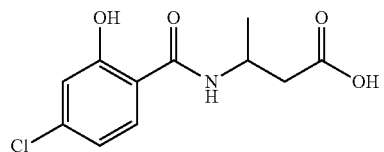

3-(4-Chloro-2-hydroxy-benzoylamino)-butyric acid,

Compound 146

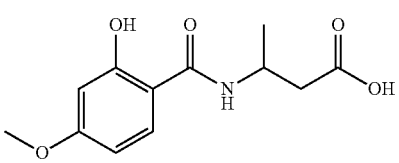

3-(2-Hydroxy-4-methoxy-benzoylamino)-butyric acid,

Compound 147

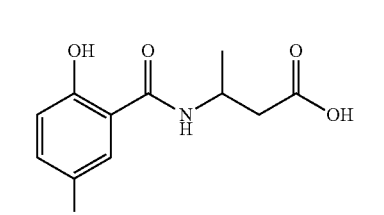

3-(5-Bromo-2-hydroxy-benzoylamino)-butyric acid,

Compound 148

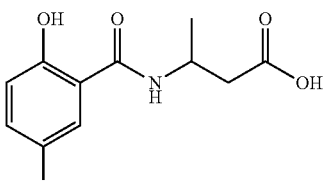

3-(5-Chloro-2-hydroxy-benzoylamino)-butyric acid,

Compound 149

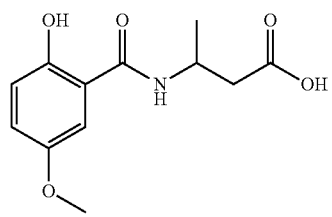

3-(2-Hydroxy-5-methoxy-benzoylamino)-butyric acid,

Compound 150

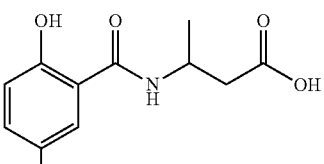

3-(2-Hydroxy-5-methyl-benzoylamino)-butyric acid,

Compound 151

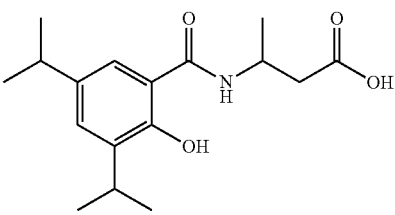

3-(2-hydroxy-3,5-diisopropyl-benzoylamino)-butyric acid, and salts thereof.

8. A pharmaceutical composition comprising:
(A) at least one biologically active agent; and
(B) a compound of claim 7.

9. A pharmaceutical composition comprising:
(A) at least one biologically active agent; and
(B) a compound selected from Compound 152

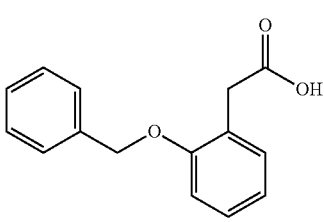

2-Benzyloxyphenyl acetic acid,

Compound 153

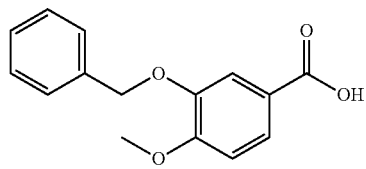

3-Benzyloxy-4-methoxybenzoic acid,

Compound 154

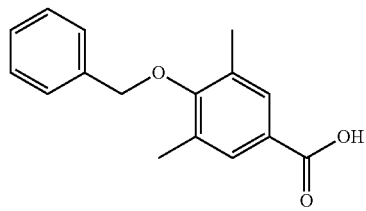

4-Benzyloxy-3,5-dimethylbenzoic acid,

Compound 156

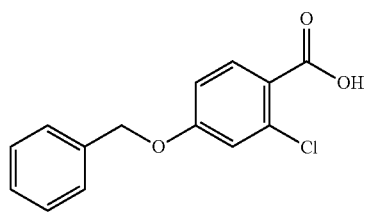

4-(Benzyloxy)-2-chlorobenzoic acid,

Compound 157

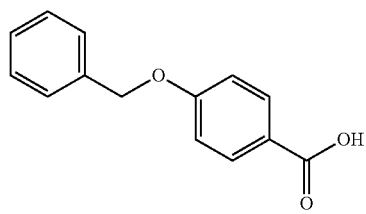

4-Benzyloxy-benzoic acid,

Compound 158

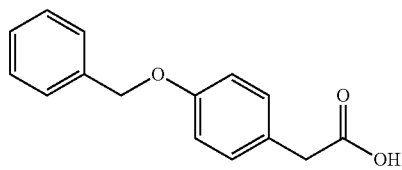

4-(Benzyloxy-phenyl)-acetic acid, and salts thereof.

10. A compound selected from:

Compound 160

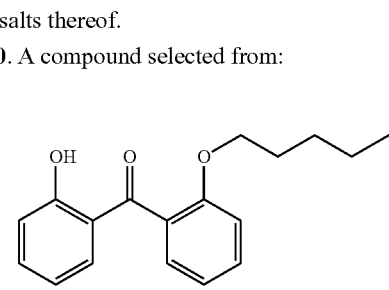

6-(2-(2-Hydroxybenzoyl)phenoxy)hexanoic acid,

Compound 161

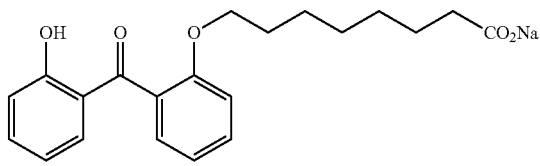

Sodium 8-(2-(2-Hydroxybenzoyl)phenoxy)octanoate,

Compound 162

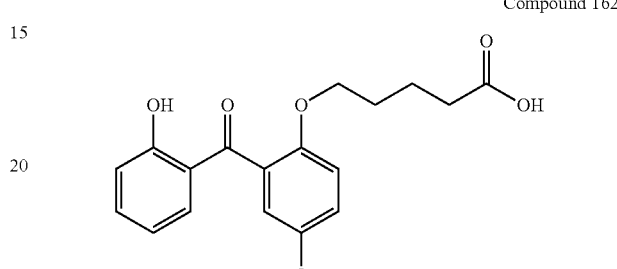

5-(2-(2-Hydroxybenzoyl)-4-methoxyphenoxy)valeric acid,

Compound 163

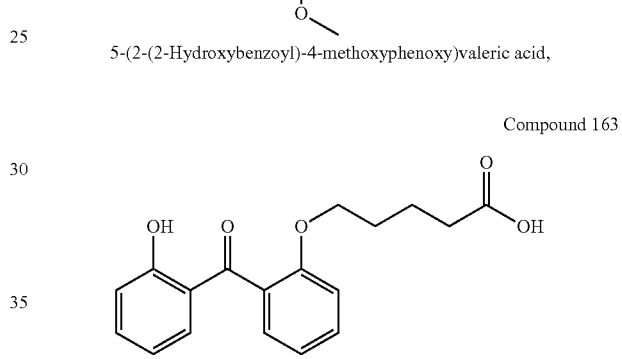

5-(2-(2-Hydroxybenzoyl)phenoxy)valeric acid,

Compound 164

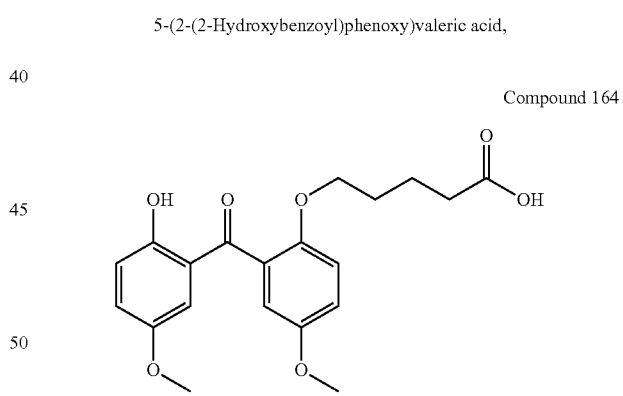

5-(2-(2-Hydroxy-5-methoxybenzoyl)-4-methoxyphenoxy)valeric acid,

Compound 165

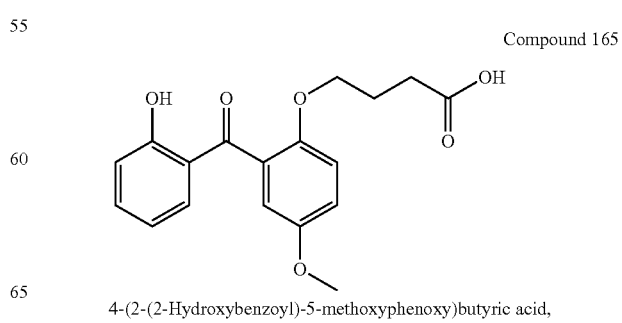

4-(2-(2-Hydroxybenzoyl)-5-methoxyphenoxy)butyric acid,

-continued

Compound 166

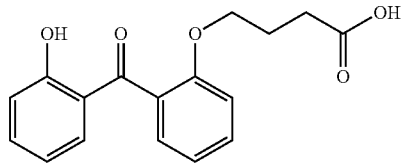

4-(2-(2-Hydroxybenzoyl)phenoxy)butyric acid,

Compound 167

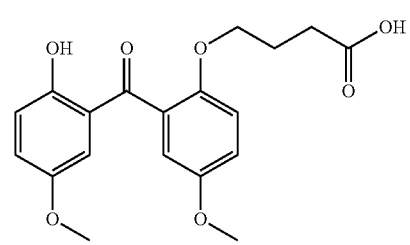

4-(2-(2-Hydroxy-5-methoxybenzoyl)-4-methoxyphenoxy)butyric acid,

Compound 168

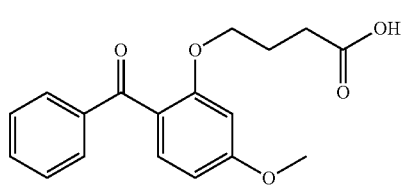

4-(2-Benzoyl-5-methoxyphenoxy)butyric acid,

Compound 169

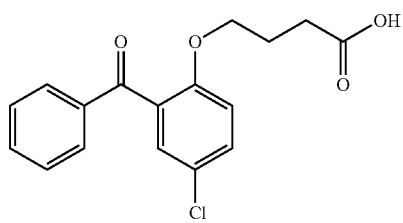

4-(2-Benzoyl-4-chlorophenoxy)butyric acid,

Compound 170

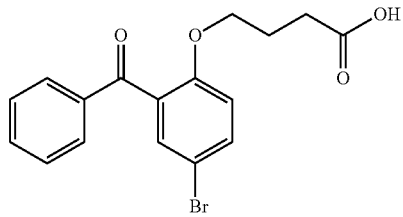

4-(2-Benzoyl-4-bromophenoxy)butyric acid,

Compound 171

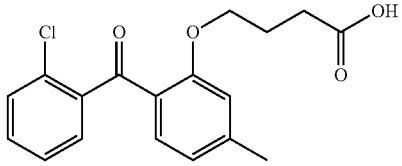

4-(2-(2-Chlorobenzoyl)-5-methylphenoxy)butyric acid,

-continued

Compound 172

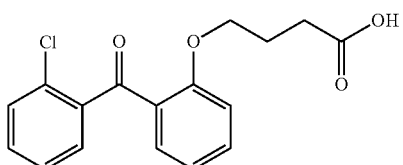

4-(2-(2-Chlorobenzoyl)-4-methylphenoxy)butyric acid,

Compound 173

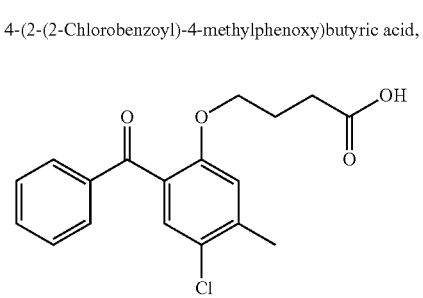

4-(2-Benzoyl-4-chloro-5-methylphenoxy)butyric acid, and salts thereof.

11. A pharmaceutical composition comprising:
(A) at least one biologically active agent; and
(B) a compound of claim 10.

12. A compound selected from:

Compound 177

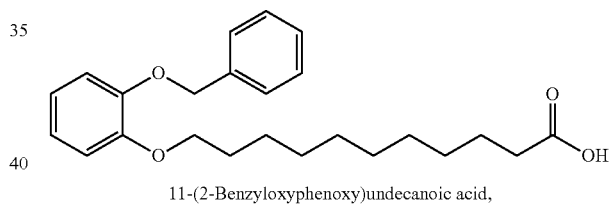

11-(2-Benzyloxyphenoxy)undecanoic acid,

Compound 178

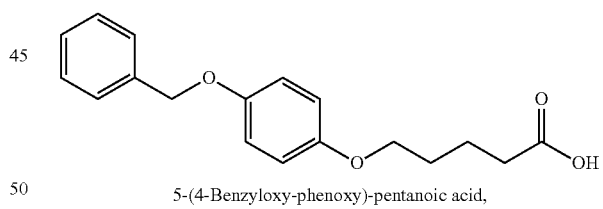

5-(4-Benzyloxy-phenoxy)-pentanoic acid, and salts thereof.

13. A pharmaceutical composition comprising:
(A) at least one biologically active agent; and
(B) a compound of claim 12.

14. The pharmaceutical composition of claim 2, wherein the biologically active agent is recombinant human growth hormone.

15. The pharmaceutical composition of claim 2, wherein the biologically active agent is insulin.

16. The pharmaceutical composition of claim 2, wherein the biologically active agent is heparin.

17. The pharmaceutical composition of claim 2, wherein the biologically active agent is calcitonin.

18. The pharmaceutical composition of claim 2, wherein the biologically active agent is interferon.

19. The pharmaceutical composition of claim 2, wherein the biologically active agent is cromolyn sodium.

20. A compound according to claim 1, selected from Compounds 3, 4, 6, 8, 11, 13, 14, 16, 18, 19, 20, 21, and salts thereof.

21. A pharmaceutical composition comprising (A) at least one biologically active agent and (B) a compound of claim 20.

22. A compound according to claim 4, selected from Compounds 23-27, 30-35, 38, 39, 41-49, 51-55, 57-59, 61-65, 68, 69, 71-78, 80-85, 87, 88, 90-96, 98-104, 106-108, 110, and salts thereof.

23. A pharmaceutical composition comprising (A) at least one biologically active agent and (B) a compound of claim 22.

24. A compound selected from

Compound 141
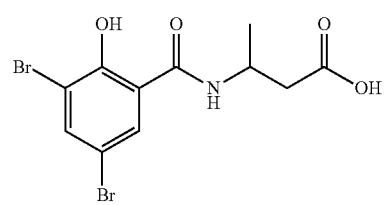
3-(3,5-Dibromo-2-hydroxy-benzoylamino)-butyric acid,

Compound 142
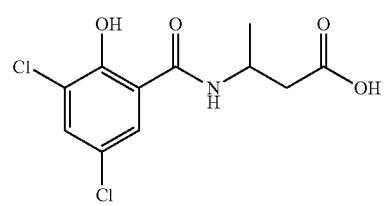
3-(3,5-Dichloro-2-hydroxy-benzoylamino)-butyric acid,

Compound 143
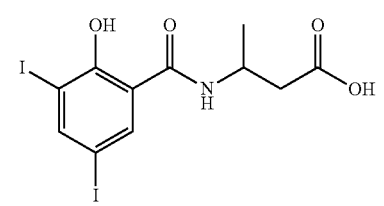
3-(2-Hydroxy-3,5-diiodo-benzoylamino)-butyric acid,

Compound 144
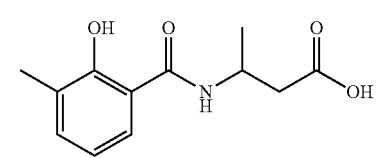
3-(2-Hydroxy-3-methyl-benzoylamino)-butyric acid,

Compound 146
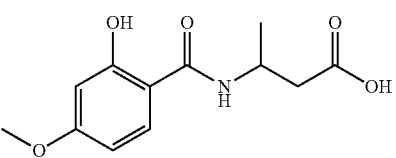
3-(2-Hydroxy-4-methoxy-benzoylamino)-butyric acid,

-continued

Compound 147
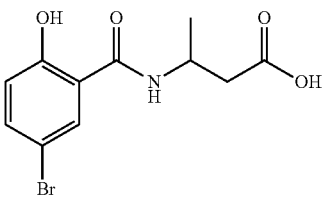
3-(5-Bromo-2-hydroxy-benzoylamino)-butyric acid,

Compound 148
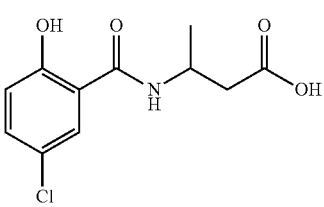
3-(5-Chloro-2-hydroxy-benzoylamino)-butyric acid,

Compound 149
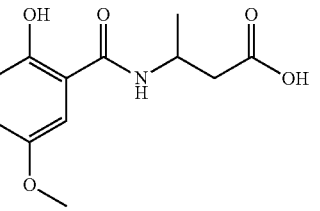
3-(2-Hydroxy-5-methoxy-benzoylamino)-butyric acid,

Compound 150
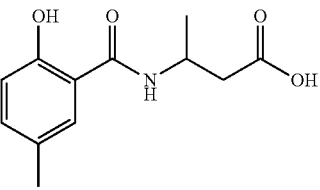
3-(2-Hydroxy-5-methyl-benzoylamino)-butyric acid,

Compound 151
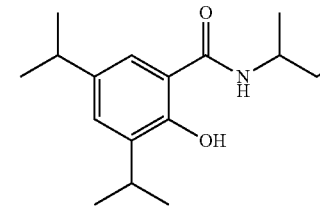
3-(2-hydroxy-3,5-diisopropyl-benzoylamino)-butyric acid, and salts thereof.

25. A pharmaceutical composition comprising (A) at least one biologically active agent and (B) a compound of claim 24.

* * * * *